US012569410B2

(12) United States Patent
Endo et al.

(10) Patent No.: US 12,569,410 B2
(45) Date of Patent: Mar. 10, 2026

(54) PHOTOCURABLE COMPOSITION AND DENTAL PRODUCT

(71) Applicant: MITSUI CHEMICALS, INC., Tokyo (JP)

(72) Inventors: Suguru Endo, Ichikawa (JP); Toshikazu Sakamaki, Tokyo (JP); Mai Kimura, Sodegaura (JP); Hiroki Murai, Ichihara (JP); Takaaki Hayashi, Funabashi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 982 days.

(21) Appl. No.: 17/639,927

(22) PCT Filed: Oct. 28, 2020

(86) PCT No.: PCT/JP2020/040460

§ 371 (c)(1),
(2) Date: Mar. 3, 2022

(87) PCT Pub. No.: WO2021/085481

PCT Pub. Date: May 6, 2021

(65) Prior Publication Data

US 2022/0339077 A1 Oct. 27, 2022

(30) Foreign Application Priority Data

Oct. 28, 2019 (JP) ................................ 2019-195499
Oct. 28, 2019 (JP) ................................ 2019-195500
Apr. 13, 2020 (JP) ................................ 2020-071833

(51) Int. Cl.
*A61K 6/62* (2020.01)
*A61K 6/887* (2020.01)
(Continued)

(52) U.S. Cl.
CPC ................ *A61K 6/62* (2020.01); *A61K 6/887* (2020.01); *C08F 2/50* (2013.01); *C08F 22/02* (2013.01);
(Continued)

(58) Field of Classification Search
CPC ......... A61K 6/62; A61K 6/887; C08F 220/18; C08F 290/067
See application file for complete search history.

(56) References Cited

U.S. PATENT DOCUMENTS 5,177,120 A * 1/1993 Hare .................... C08G 18/672 523/109
2002/0068770 A1* 6/2002 Kashiwame .......... C08F 283/06 522/90
(Continued)

FOREIGN PATENT DOCUMENTS

CN 107847297 A 3/2018
EP 982629 A1 * 3/2000 .............. B41M 1/04
(Continued)

*Primary Examiner* — Kregg T Brooks
*Assistant Examiner* — David R. Foss
(74) *Attorney, Agent, or Firm* — BUCHANAN INGERSOLL & ROONEY PC

(57) ABSTRACT

A photocurable composition includes a (meth)acrylic monomer component and a photopolymerization initiator, wherein an adhesive force of a cured product is less than or equal to 1.5 N, and a rupture elongation of the cured product is greater than or equal to 20%.

18 Claims, 5 Drawing Sheets

(51) Int. Cl.

| | |
|---|---|
| ***C08F 2/50*** | (2006.01) |
| ***C08F 22/02*** | (2006.01) |
| ***C08F 22/38*** | (2006.01) |
| ***C08F 220/18*** | (2006.01) |
| ***C08F 290/06*** | (2006.01) |
| *B33Y 70/00* | (2020.01) |

(52) U.S. Cl.
CPC ............... *C08F 22/38* (2013.01); *B33Y 70/00* (2014.12); *C08F 220/18* (2013.01); *C08F 290/067* (2013.01)

(56) References Cited

U.S. PATENT DOCUMENTS

| | | | |
|---|---|---|---|
| 2003/0088011 | A1 | 5/2003 | Kamohara et al. |
| 2017/0007362 | A1 | 1/2017 | Chen et al. |

FOREIGN PATENT DOCUMENTS

| | | | | |
|---|---|---|---|---|
| EP | 3 925 994 | A1 | 12/2021 | |
| JP | H11-349645 | A | 12/1999 | |
| JP | 2003019240 | A | 1/2003 | |
| JP | 2018-039962 | A | 3/2018 | |
| JP | 2019-026809 | A | 2/2019 | |
| KR | 10-2009-0090866 | A | 8/2009 | |
| WO | WO-2018184847 | A1 * | 10/2018 | ............. B65D 33/18 |

* cited by examiner

PHOTOCURABLE COMPOSITION AND DENTAL PRODUCT

TECHNICAL FIELD

The present disclosure relates to a photocurable composition and a dental product.

BACKGROUND ART

Resins have conventionally been used in various applications, and characteristics that correspond to the applications are needed. For example, a mouthpiece that is a dental product is used in treating temporomandibular joint arthrosis and in orthodontic treatments.

Dental prostheses, appliances that are used within the oral cavity (mouthguards and the like), other dental products (gingiva masks and the like) and the like have become known as dental products in recent years, and various materials are used therefor in accordance with respective applications thereof.

For example, Patent Document 1 discloses a composition for a mouthguard that is characterized by being formed from A) a styrene block copolymer, B) at least one type of thermoplastic resin selected from the group consisting of alicyclic saturated hydrocarbon resins, terpene resins and aliphatic petroleum resins, and C) at least one type of wax selected from the group consisting of mineral waxes, synthetic waxes, vegetable waxes and animal waxes.

Patent Document 1: Japanese Patent Application Laid-Open (JP-A) No. 2003-019240

SUMMARY OF INVENTION

Technical Problem

For example, there are cases in which a dental product such as a mouthpiece for sports or the like deforms due to frequent use of the product. Further, there are cases in which the shape of a product that has deformed after usage is not restored, and cracks, fissures or the like form therein. Therefore, there is the trend that materials that suppress these issues are demanded. Further, in a dental product such as a mouthpiece for sports or the like, because the adhesiveness of the product is high at the time when the product is used, there are cases in which the handleability of the product suffers.

Problem A that a first embodiment of the present disclosure solves is the provision of a photocurable composition from which there can be obtained a cured product in which the formation of cracks and fissures is suppressed and that has excellent handleability, and a dental product having a cured product of this photocurable composition.

Further, at the time of using a dental product such as a mouthpiece or the like, an unpleasant sensation may arise due to some type of force being applied to the contacting surfaces of the teeth and the dental product. Frequently, there are also cases in which the aforementioned unpleasant sensation manifests an unpleasant sensation such as pain or the like.

The aforementioned unpleasant sensation often becomes a problem in using the dental product, and there is a demand for improvement thereof.

Problem B that a second embodiment of the present disclosure solves is the provision of a photocurable composition from which there can be obtained a cured product in which unpleasant sensations are suppressed when used for human bodies and that has excellent handleability, and a dental product having a cured product of this photocurable composition. Solution to Problem Specific means for solving at least one problem among above-described problem A and above-described problem B include the following aspects.

The first embodiment is exemplified by the photocurable composition of following <1>.

The second embodiment is exemplified by the photocurable composition of following <6>.

<1> A photocurable composition comprising a (meth)acrylic monomer component and a photopolymerization initiator,
wherein an adhesive force of a cured product is less than or equal to 1.5 N, and a rupture elongation of the cured product is greater than or equal to 20%.

<2> The photocurable composition of <1>, wherein the rupture elongation of the cured product is greater than or equal to 40%.

<3> A photocurable composition comprising a (meth)acrylic monomer component and a photopolymerization initiator,
wherein an adhesive force of a cured product is less than or equal to 1.5 N, and a shock absorbing ability of the cured product is greater than or equal to 20% and less than or equal to 80%.

<4> The photocurable composition of <3>, wherein the shock absorbing ability of the cured product is greater than or equal to 20% and less than or equal to 70%.

<5> The photocurable composition of <3> or <4>, wherein a rupture elongation of the cured product is greater than or equal to 20%.

<6> A photocurable composition comprising a (meth)acrylic monomer component and a photopolymerization initiator,
wherein an adhesive force of a cured product is less than or equal to 1.5 N, and a shore A hardness of the cured product is less than or equal to 97.

<7> The photocurable composition of any one of <1> to <6>, wherein an aromatic ring concentration in the (meth)acrylic monomer component is greater than or equal to 0.00100 mol/g.

<8> The photocurable composition of any one of <1> to <7>, wherein the (meth)acrylic monomer component contains:
a (meth)acrylic monomer (A) having two (meth)acryloyl groups, and
a (meth)acrylic monomer (B) having one (meth)acryloyl group.

<9> The photocurable composition of <8>, wherein at least one of the (meth)acrylic monomer (A) or the (meth)acrylic monomer (B) has an aromatic group.

<10> A photocurable composition comprising a (meth)acrylic monomer component and a photopolymerization initiator, wherein:
the (meth)acrylic monomer component contains a (meth)acrylic monomer (A) having two (meth)acryloyl groups and contains a (meth)acrylic monomer (B) having one (meth)acryloyl group,
a molecular weight per one (meth)acryloyl group in the (meth)acrylic monomer (A) is greater than or equal to 300 g/mol, and
at least one of the (meth)acrylic monomer (A) or the (meth)acrylic monomer (B) has an aromatic group.

<11> The photocurable composition of any one of <8> to <10>, wherein a content of the (meth)acrylic monomer (A), with respect to a total content of 1000 parts by mass of the (meth)acrylic monomer (A) and the (meth) acrylic monomer (B), is 250 parts by mass to 800 parts by mass.

<12> The photocurable composition of any one of <8> to <11>, wherein the (meth)acrylic monomer (A) includes a compound expressed by the following Formula (1):

[Chemical Formula 1]

Formula (1)

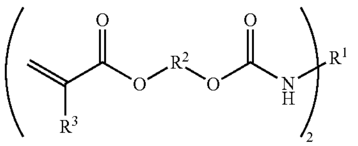

wherein, in Formula (1), each $R^1$ and $R^2$ independently represents a divalent linking group, and each $R^3$ is independently a methyl group or a hydrogen atom.

<13> The photocurable composition of <12>, wherein:

$R^1$ is a divalent chain hydrocarbon group, or is a group formed from a divalent chain hydrocarbon group and at least one group selected from the group consisting of divalent hydrocarbon groups having an alicyclic structure, divalent hydrocarbon groups having an aromatic structure, and divalent groups containing a hetero atom, and the divalent hydrocarbon groups having an aromatic structure are divalent hydrocarbon groups expressed by the following Formula (1-a),

[Chemical Formula 2]

(1-a)

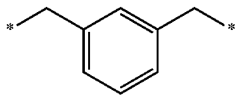

wherein, in Formula (1-a), * represents a bonding site.

<14> The photocurable composition of <12>, wherein $R^1$ is a divalent chain hydrocarbon group, or is a group formed from a divalent chain hydrocarbon group and at least one group selected from the group consisting of divalent hydrocarbon groups having an alicyclic structure and divalent groups containing a hetero atom.

<15> The photocurable composition of <13> or <14>, wherein the divalent groups containing a hetero atom in $R^1$ contain at least one bond selected from the group consisting of urethane bonds and ether bonds.

<16> The photocurable composition of any one of <8> to <15>, wherein at least one of the following (a) or the following (b) is satisfied:

(a) the (meth)acrylic monomer (A) includes a (meth) acrylic monomer (A-1), in which a molecular weight per one (meth)acryloyl group is greater than or equal to 300 g/mol and is less than or equal to 600 g/mol, and contains a (meth)acrylic monomer (A-2), in which a molecular weight per one (meth)acryloyl group is greater than 600 g/mol and is less than or equal to 15000 g/mol, or (b) the (meth)acrylic monomer (B) includes a (meth) acrylic monomer (B-1) having two aromatic rings and contains a (meth)acrylic monomer (B-2) having one aromatic ring.

<17> The photocurable composition of any one of <8> to <16>, wherein an aromatic ring concentration in the (meth)acrylic monomer (A) is less than or equal to 0.0016 mol/g.

<18> The photocurable composition of any one of <8> to <17>, wherein a total content of the (meth)acrylic monomer (A) and the (meth)acrylic monomer (B) in the (meth)acrylic monomer component is greater than or equal to 90% by mass.

<19> The photocurable composition of any one of <7> to <18>, wherein Z1 in the following Formula β is $1\times10^4$ to $100\times10^4$:

$$Z1=X1/Y1 \qquad \text{Formula } \beta$$

wherein X1 (g/mol) is a molecular weight of the (meth)acrylic monomer (A) per one (meth)acryloyl group, and Y1 (mol/g) is an aromatic ring concentration in the (meth)acrylic monomer component.

<20> The photocurable composition of any one of <1> to <19>, wherein a viscosity at 25° C. and 50 rpm measured by an E-type viscometer is 10 mPa·s to 5000 mPa·s.

<21> The photocurable composition of any one of <1> to <20>, which is used for stereolithography.

<22> The photocurable composition of any one of <1> to <21>, which is used in fabricating a dental product by stereolithography.

<23> The photocurable composition of any one of <1> to <22>, which is used in fabricating a mouthpiece, a gingiva mask, or a lining material by stereolithography.

<24> A dental product comprising a cured product of the photocurable composition of any one of <1> to <23>.

<25> The dental product of <24>, which is used as a mouthpiece, a gingiva mask, or a lining material.

<26> A method of preparing three-dimensional image data of a mouthguard, comprising the step of preparing three dimensional data of a mouthguard in which a thickness of an occlusal surface of a central incisor portion is greater than or equal to 1.5 times a thickness of an occlusal surface of a second molar portion.

<27> The method of preparing three-dimensional image data of a mouthguard of <26>, wherein the thickness of the occlusal surface of the central incisor portion is less than or equal to 5 times the thickness of the occlusal surface of the second molar portion.

<28> A method of manufacturing a mouthguard, comprising: a step of preparing three-dimensional image data of a mouthguard by the method of preparing three-dimensional image data of a mouthguard of <26> or <27>; and a step of manufacturing a mouthguard by stereolithography by using the prepared three-dimensional image data of a mouthguard.

Specific means for solving above-described problem A include the following aspects.

<1A> A photocurable composition comprising a (meth) acrylic monomer component and a photopolymerization initiator, wherein adhesive force of a cured product is less than or equal to 1.5 N, and rupture elongation of the cured product is greater than or equal to 20%.

<2A> The photocurable composition of <1A>, wherein the rupture elongation of the cured product is greater than or equal to 40%.

<3A> A photocurable composition comprising a (meth) acrylic monomer component and a photopolymerization initiator, wherein adhesive force of a cured product is less than or equal to 1.5 N, and shock absorbing ability of the cured product is greater than or equal to 20% and less than or equal to 80%.

<4A> The photocurable composition of <3A>, wherein the shock absorbing ability of the cured product is greater than or equal to 20% and less than or equal to 70%.

<5A> The photocurable composition of <3A > or <4A>, wherein rupture elongation of the cured product is greater than or equal to 20%.

<6A> The photocurable composition of any one of <1A> to <5A>, wherein the (meth)acrylic monomer component contains (meth)acrylic monomer (A) having two (meth)acryloyl groups, and (meth)acrylic monomer (B) having one (meth)acryloyl group.

<7A> The photocurable composition of <6A>, wherein at least one of (meth)acrylic monomer (A) and (meth) acrylic monomer (B) has an aromatic group.

<8A> A photocurable composition comprising a (meth) acrylic monomer component and a photopolymerization initiator, wherein the (meth)acrylic monomer component contains (meth)acrylic monomer (A) having two (meth)acryloyl groups, and (meth)acrylic monomer (B) having one (meth)acryloyl group, and the molecular weight per one (meth)acryloyl group in (meth)acrylic monomer (A) is greater than or equal to 300 g/mol, and at least one of (meth)acrylic monomer (A) and (meth)acrylic monomer (B) has an aromatic group.

<9A> The photocurable composition of any one of <6A> to <8A>, wherein content of (meth)acrylic monomer (A), with respect to a total content of 1000 parts by mass of (meth)acrylic monomer (A) and (meth)acrylic monomer (B), is 250 parts by mass ~800 parts by mass.

<10A> The photocurable composition of any one of <6A> to <9A>, wherein a total content of (meth)acrylic monomer (A) and (meth)acrylic monomer (B) in the (meth)acrylic monomer component is greater than or equal to 90% by mass.

<11A> The photocurable composition of any one of <6A> to <10A>, wherein (meth)acrylic monomer (A) includes a urethane bond.

<12A> The photocurable composition of any one of <1A> to <11A>, wherein an aromatic ring concentration in the (meth)acrylic monomer component is greater than or equal to 0.00100 mol/g.

<13A> The photocurable composition of any one of <1A> to <12A>, wherein viscosity at 25° C. and 50 rpm measured by an E-type viscometer is 10 mPa·s 5000 10 mPa·s.

<14A> The photocurable composition of any one of <1A> to <13A> that is used for stereolithography.

<15A> The photocurable composition of any one of <1A> to <14A> that is used in fabricating a dental product by stereolithography.

<16A> The photocurable composition of any one of <1A> to <15A> that is used in fabricating a mouthpiece or a gingiva mask by stereolithography.

<17A> A dental product comprising a cured product of the photocurable composition of any one of <1A> to <16A>.

<18A> The dental product of <17A> that is used as a mouthpiece or as a gingiva mask.

Specific means for solving above-described problem B include the following aspects.

<1B> A photocurable composition comprising a (meth) acrylic monomer component and a photopolymerization initiator, wherein adhesive force of a cured product is less than or equal to 1.5 N, and shore A hardness of the cured product is less than or equal to 97.

<2B> The photocurable composition of <1B>, wherein the (meth)acrylic monomer component contains (meth) acrylic monomer (A) having two (meth)acryloyl groups, and (meth)acrylic monomer (B) having one (meth)acryloyl group.

<3B> The photocurable composition of <2B>, wherein at least one of (meth)acrylic monomer (A) and (meth) acrylic monomer (B) has an aromatic group.

<4B> A photocurable composition comprising a (meth) acrylic monomer component and a photopolymerization initiator, wherein the (meth)acrylic monomer component contains (meth)acrylic monomer (A) having two (meth)acryloyl groups, and (meth)acrylic monomer (B) having one (meth)acryloyl group, and the molecular weight per one (meth)acryloyl group in (meth)acrylic monomer (A) is greater than or equal to 300 g/mol, and at least one of (meth)acrylic monomer (A) and (meth)acrylic monomer (B) has an aromatic group, and the shore A hardness of a cured product is less than or equal to 97.

<5B> The photocurable composition of any one of <2B> to <4B>, wherein content of (meth)acrylic monomer (A), with respect to a total content of 1000 parts by mass of (meth)acrylic monomer (A) and (meth)acrylic monomer (B), is 250 parts by mass ~800 parts by mass.

<6B> The photocurable composition of any one of <2B> to <5B>, wherein a total content of (meth)acrylic monomer (A) and (meth)acrylic monomer (B) in the (meth)acrylic monomer component is greater than or equal to 90% by mass.

<7B> The photocurable composition of any one of <2B> to <6B>, wherein (meth)acrylic monomer (A) includes a urethane bond.

<8B> The photocurable composition of any one of <1B> to <7B>, wherein the shore A hardness of the cured product is greater than or equal to 50.

<9B> The photocurable composition of any one of <1B> to <8B>, wherein an aromatic ring concentration in the (meth)acrylic monomer component is greater than or equal to 0.00100 mol/g.

<10B> The photocurable composition of any one of <1B> to <9B>, wherein viscosity at 25° C. and 50 rpm measured by an E-type viscometer is 10 mPa·s 5000 10 mPa·s.

<11B> The photocurable composition of any one of <1B> to <10B> that is used for stereolithography.

<12B> The photocurable composition of any one of <1B> to <11B> that is used in fabricating a dental product by stereolithography.

<13B> The photocurable composition of any one of <1B> to <12B> that is used in fabricating a mouthpiece or a lining material by stereolithography.

<14B> A dental product comprising a cured product of the photocurable composition of any one of <1B> to <13B>.

<15B> The dental product of <14B> that is a mouthpiece or a lining material.

Advantageous Effects of Invention

In accordance with the first embodiment of the present disclosure, there can be provided a photocurable composition from which is obtained a cured product in which the formation of cracks and fissures is suppressed and that has excellent handleability, and a dental product having a cured product of this photocurable composition.

In accordance with the second embodiment of the present disclosure, there can be provided a photocurable composition from which is obtained a cured product in which unpleasant sensations are suppressed when used for human bodies and that has excellent handleability, and a dental product having a cured product of this photocurable composition.

DESCRIPTION OF EMBODIMENTS

Figure 1:
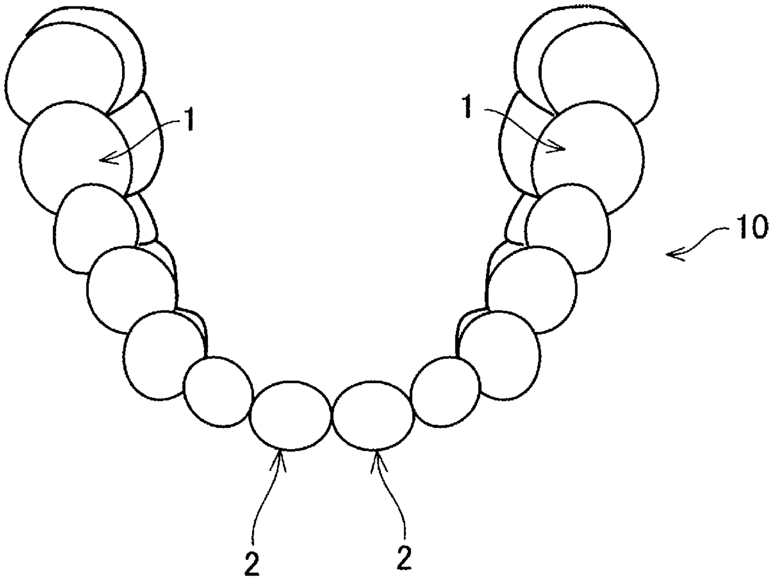
FIG. 1 is a drawing depicting the external appearance of a mouthguard for the upper jaw in an embodiment of the present disclosure.

In the present disclosure, numerical ranges expressed by using "—" mean ranges in which the numerical values listed before and after the "—" are included as the lower limit and the upper limit.

Further, in the present disclosure, "(meth)acrylic monomers" is a concept encompassing both acrylic monomers and methacrylic monomers.

Further, in the present disclosure, "(meth)acryloyloxy group" is a concept encompassing both acryloyloxy group and methacryloyloxy group. When "acryloyloxy group" or "methacryloyloxy group" is written, it refers only to that type of group, respectively.

In the present disclosure, "urethane bond" means an —NHC(=O)O— bond.

In the present disclosure, when stating the amounts of the respective components in a composition, and when plural substances corresponding to a component in a composition are present, "amount" means the total amount of the plural substances that exist in the composition, unless otherwise stated.

The following first embodiment and second embodiment are examples of the photocurable composition of the present disclosure.

Photocurable Composition of First Embodiment

Following Form 1a, Form 1b and Form 1c are examples of the photocurable composition of the first embodiment.

Each aspect (e.g., Form 1a) may satisfy the characteristics of the other forms (e.g., Form 1b and/or Form 1c).

<<Form 1a>>

The photocurable composition relating to Form 1a of the first embodiment contains a (meth)acrylic monomer component and a photopolymerization initiator, and the adhesive force of the cured product is less than or equal to 1.5 N, and the rupture elongation of the cured product is greater than or equal to 20%.

The inventors of the present disclosure focused on the point of increasing the rupture elongation of a cured product obtained by photocuring a photocurable composition (hereinafter also simply called cured product), for the purpose of suppressing the formation of cracks and fissures in a product.

Due to the inventors of the present disclosure studying the above-described point, the inventors arrived at the knowledge that, in a case of increasing the rupture elongation of a cured product obtained by photocuring a photocurable composition (hereinafter also simply called cured product), the adhesive force of the cured product increases, and this is one cause of deteriorating the handleability.

Namely, from the standpoint of obtaining a cured product that exhibits both handleability and a suppression of cracks and fissures, it is important to increase the rupture elongation of the cured product obtained by photocuring a photocurable resin, and to keep down the adhesive force of the cured product.

Due to the photocurable composition of Form 1a containing a (meth)acrylic monomer component and a photopolymerization initiator, and the adhesive force of the cured product being less than or equal to 1.5 N, and the rupture elongation of the cured product being greater than or equal to 20%, in a case in which the photocurable composition of the first embodiment is photocured, a cured product that has excellent rupture elongation and whose adhesive force is kept down can be obtained. Due thereto, a cured product having excellent handleability and suppression of cracks and fissures can be obtained.

<Adhesive Force of Cured Product>

The adhesive force of the cured product that is obtained by photocuring the photocurable composition of Form 1a is less than or equal to 1.5 N.

Due thereto, the handleability of the cured product can be improved.

From standpoints similar to those described above, the aforementioned adhesive force is preferably less than or equal to 1.0 N, and more preferably less than or equal to 0.7 N, and even more preferably less than or equal to 0.35 N.

The lower limit of the adhesive force of the cured product is not particularly limited, and may be greater than 0 N, or may be greater than or equal to 0.01 N.

Note that the method of measuring the adhesive force of the cured product is as follows.

First, by illuminating visible light onto the photocurable composition by using a 3D printer, the photocurable composition is shaped to length 20 mm×width 20 mm×thickness 2 mm, and a shaped product (layered width 50 μm) is obtained. In the aforementioned illuminating of the visible light using the 3D printer, visible light of a wavelength of 405 nm is illuminated onto the respective layers within a range of 5.0 $mJ/cm^2$~10 $mJ/cm^2$ and under the condition of becoming a desired thickness.

By illuminating ultraviolet light of a wavelength of 365 nm under the condition of 10 $J/cm^2$ onto the shaped product that was obtained as described above, and definitively curing the shaped product, a cured product is obtained. The cured product that is obtained is used as the object of measurement of adhesive force.

The cured product that is the object of measurement is placed onto a sample affixing stand. A probe, which is made of aluminum and whose contact surface area is length 10 mm×width 10 mm, and a 20 mm×20 mm surface of the cured product, are made to contact one another, and are left for 1.0±0.1 seconds under a contact load of 0.98±0.01 $N/cm^2$.

Thereafter, by using a tensile testing device, the aforementioned probe is pulled-off from the contact surface in the vertical direction at a speed of 5 mm per second. Then, the maximum load needed at the time of pulling the aforementioned probe off from the contact surface is determined, and is used as the adhesive force (unit: N) of the cured product in the present disclosure.

<Rupture Elongation of Cured Product>

At the photocurable composition of Form 1a, the rupture elongation of the cured product obtained by curing the photocurable composition is greater than or equal to 20%.

Due thereto, at the time when external force is applied to the cured product, the occurrence of breakage (formation of fissures, formation of tears, formation of cracks, and the like) can be suppressed.

Further, due to the rupture elongation of the cured product being within the above-described range, the restorability (an improvement in the restoring speed, a suppression of the amount of deformation at the time of being restored, and the like), which is that the shape of the cured product return to the shape before external force was applied when the external force is cancelled after the external force is once applied to the cured product, can be improved. Further, in a case in which the rupture elongation of the cured product is within the above-described range, and the adhesive force of the cured product is less than or equal to 1.5 N, the above-described restorability can be improved even more. Moreover, in a case in which the rupture elongation of the cured product is within the above-described range, and the adhesive force of the cured product is less than or equal to 1.5 N, the amount of deformation at the time of the above-described restoring can be suppressed better.

From the above-described standpoints, the rupture elongation of the cured product is preferably greater than or equal to 40%, and more preferably greater than or equal to 60%.

The upper limit of the rupture elongation may be less than or equal to 110%, or may be less than or equal to 100%, or may be less than or equal to 90%.

Note that, in the present disclosure, the rupture elongation of the cured product is measured by the following method.

First, by illuminating visible light onto the photocurable composition by using a 3D printer, the photocurable composition is shaped into the shape of a dumbbell-type test piece conforming to ISO 37-2, and a shaped product (layered width 50 μm) is obtained.

In the aforementioned illuminating of the visible light using the 3D printer, visible light of a wavelength of 405 nm is illuminated onto the respective layers within a range of 5.0 $mJ/cm^2$~10 $mJ/cm^2$ and under the condition of becoming a desired thickness.

By illuminating ultraviolet light of a wavelength of 365 nm under the condition of 10 $J/cm^2$ onto the shaped product that was obtained as described above, and definitively curing the shaped product, a cured product is obtained. The cured product that is obtained is used as the object of measurement of rupture elongation.

The rupture elongation of the cured product that is the object of measurement is measured in accordance with ISO 37: 2017 by using a tensile testing device and under the condition of a pulling speed of 500±50 mm/minute.

(Hardness (Shore A Hardness) of Cured Product)

The hardness of the cured product of Form 1a is preferably greater than or equal to 50.

Even though there is the general trend that, the lower the hardness of (i.e., the softer) the cured product, the easier it is for the adhesive force to increase, due to the hardness of the cured product being greater than or equal to 50, the adhesive force of the cured product can be kept down better.

The upper limit of the hardness of the cured product is not particularly limited, and may be less than or equal to 99.

Further, as described above, even though there is the general trend that, the lower the hardness of (i.e., the softer) the cured product, the easier it is for the adhesive force to increase, even if the hardness of the cured product that is obtained is less than or equal to 90, the adhesive force of the cured product can be kept down, and, even if the hardness is less than or equal to 80, the adhesive force of the cured product can be kept down.

Note that, in the present disclosure, the hardness of the cured product is measured by the following method.

First, by illuminating visible light onto the photocurable composition by using a 3D printer, the photocurable composition is shaped to length 25 mm×width 25 mm×thickness 6 mm, and a shaped product (layered width 50 μm) is obtained. In the aforementioned illuminating of the visible light using the 3D printer, visible light of a wavelength of 405 nm is illuminated onto the respective layers within a range of 5.0 $mJ/cm^2$~10 $mJ/cm^2$ and under the condition of becoming a desired thickness.

By illuminating ultraviolet light of a wavelength of 365 nm under the condition of 10 $J/cm^2$ onto the shaped product that was obtained as described above, and definitively curing the shaped product, a cured product is obtained. The cured product that is obtained is used as the object of measurement of hardness.

The hardness of the cured product is measured in accordance with ISO 7619-1: 2010.

(Viscosity)

From the standpoint of suitability to the fabrication of dental products by stereolithography, at the photocurable composition of Form 1a, the viscosity at 25° C. and 50 rpm (revolutions per minute) measured by using an E-type viscometer is preferably 10 mPa·s 5000 mPa·s, and more preferably 20 mPa·s~3000 mPa·s. The lower limit of the aforementioned viscosity is more preferably 50 mPa·s. The upper limit of the aforementioned viscosity is more preferably 2000 mPa·s, and even more preferably 1500 mPa·s, and particularly preferably 1200 mPa·s.

<<Form 1b>>

The photocurable composition relating to Form 1b contains a (meth)acrylic monomer component and a photopolymerization initiator, and the adhesive force of the cured product is less than or equal to 1.5 N, and the shock absorbing ability of the cured product is greater than or equal to 20% and less than or equal to 80%.

The inventors of the present disclosure focused on the shock absorbing ability of a cured product obtained by photocuring a photocurable composition (hereinafter also simply called cured product), from the standpoint of suppressing the formation of cracks and clefts in a product.

Due to the inventors of the present disclosure studying the above-described point, the inventors arrived at the knowledge that, in a case of increasing the shock absorbing ability of a cured product, the adhesive force of the cured product increases, and this is one cause of deteriorating the handleability.

Due to the photocurable composition of Form 1b containing a (meth)acrylic monomer component and a photopolymerization initiator, and the adhesive force of the cured product being less than or equal to 1.5 N, and the shock absorbing ability of the cured product being greater than or equal to 20% and less than or equal to 80%, when the photocurable composition of the first embodiment is photocured, a cured product having excellent handleability and suppression of cracks and clefts can be obtained.

In Form 1b, the adhesive force of the cured product is similar to the above-described case of Form 1a, and preferred aspects also are similar.

<Shock Absorbing Ability>

The shock absorbing ability of the cured product of Form 1b is greater than or equal to 20% and less than or equal to 80%.

By making the shock absorbing ability of the cured product be greater than or equal to 20%, the occurrence of breakage (formation of fissures, formation of tears, formation of cracks, and the like) at the cured product can be suppressed.

From standpoints similar to those described above, the shock absorbing ability of the cured product is preferably greater than or equal to 30%, and more preferably greater than or equal to 40%.

By making the shock absorbing ability of the cured product be less than or equal to 80%, the adhesive force of the cured product becoming excessively large can be prevented, and the handleability can thereby be maintained.

From standpoints similar to those described above, the shock absorbing ability of the cured product is preferably less than or equal to 70%, and more preferably less than or equal to 60%.

Due to the shock absorbing ability of the cured product being in the above-described range, and the adhesive force of the cured product being less than or equal to 1.5 N, in the same way as the case of the above-described rupture elongation, the restorability can be improved, and the amount of deformation at the time of restoring can be kept down better.

A method of adjusting the value of the shock absorbing ability by adjusting the aromatic ring concentration of the (meth)acrylic monomer component, a method of adjusting the value of the shock absorbing ability by adjusting the (meth)acryloyl group concentration (mol/g) of (meth)acrylic monomer (A) that is described later, and the like are examples of methods of adjusting the value of the shock absorbing ability. Details are described hereinafter.

~Method of Measuring Shock Absorbing Ability~

The method of measuring the shock absorbing ability of the cured product in the present disclosure is as follows.

First, by illuminating visible light onto the photocurable composition by using a 3D printer, the photocurable composition is shaped to length 20 mm×width 20 mm×thickness 3 mm, and a shaped product (layered width 50 μm) is obtained. In the aforementioned illuminating of the visible light using the 3D printer, visible light of a wavelength of 405 nm is illuminated onto the respective layers within a range of 5.0 mJ/cm$^2$~10 mJ/cm$^2$ and under the condition of becoming a desired thickness.

By illuminating ultraviolet light of a wavelength of 365 nm under the condition of 10 J/cm$^2$ onto the shaped product that was obtained as described above, and definitively curing the shaped product, a cured product is obtained. The obtained cured product that has been left at 37° C. for 15 minutes is used as the object of measurement of shock absorbing ability.

Shock absorbing ability of the cured product in the present disclosure means the extent of the decrease in the maximum load measured by a load cell, in a case in which an iron ball is dropped freely onto the cured product.

More specifically, the value of A that is derived by the following formula is used as the shock absorbing ability (A, unit: %) of the cured product in the present disclosure.

[Mathematical Formula 1]

$$A = \left(\frac{N_0 - N}{N_0}\right) \times 100$$

In the formula, A(%) represents the shock absorbing ability, $N_0$ represents the maximum load measured by a load cell in a case in which, at 23° C., in a state in which a zirconia plate of a thickness of 1 mm and length 30 mm×width 30 mm is placed on the load cell, an iron ball (diameter 16.7 mm, 18.8 g) is freely dropped onto the center of the zirconia plate from a position of a height of 50 cm from the load cell above the zirconia plate, and N represents the maximum load measured by a load cell in a case in which, at 23° C., in a state in which a zirconia plate of a thickness of 1 mm and length 30 mm×width 30 mm is placed on the load cell, and moreover, the cured product that is the object of measurement and has a thickness of 3 mm, a length of 20 mm and a width of 20 mm is placed on the center of the aforementioned zirconia plate, an iron ball (diameter 16.7 mm, 18.8 g) is freely dropped onto the center of the cured product from a position of a height of 50 cm from the load cell above the cured product.

<<Form 1c>>

The photocurable composition relating to Form 1c of the first embodiment contains a (meth)acrylic monomer component and a photopolymerization initiator, and the (meth)acrylic monomer component contains (meth)acrylic monomer (A) having two (meth)acryloyl groups and (meth)acrylic monomer (B) having one (meth)acryloyl group, and the molecular weight per one (meth)acryloyl group in (meth)acrylic monomer (A) is greater than or equal to 300 g/mol, and at least one of (meth)acrylic monomer (A) and (meth)acrylic monomer (B) has an aromatic group.

The respective components and the like contained in the photocurable compositions of Form 1a, Form 1b and Form 1c in the first embodiment are described in detail hereinafter.

<(Meth)Acrylic Monomer Component>

The photocurable composition of the first embodiment contains a (meth)acrylic monomer component.

Due thereto, the rupture elongation of the cured product that is obtained can be improved.

The (meth)acrylic monomer component is not particularly limited, provided that it contains a (meth)acrylic monomer.

Among the above, from the standpoint of obtaining a cured product having excellent rupture elongation and suppressed adhesive force, it is preferable that the (meth)acrylic monomer component contains (meth)acrylic monomer (A) having two (meth)acryloyl groups and (meth)acrylic monomer (B) having one (meth)acryloyl group.

In the photocurable composition of the first embodiment, the (meth)acrylic monomer component preferably has an aromatic group.

Acryloyl groups are contained in the (meth)acrylic monomer component of the first embodiment. Generally, because acryloyl groups have properties such as hydrophilic property and the like, the adhesive force of a cured product tends to increase in a case in which the cured product is fabricated by using a photocurable composition containing a (meth) acrylic monomer.

However, due to the (meth)acrylic monomer component having an aromatic group, the adhesive force of the cured product that is obtained can be kept down well on the basis of the hydrophobic property of the aromatic groups themselves and the π-π interaction between the aromatic groups.

As a result, the adhesive force of the cured product can be kept down better, even if the photocurable composition of the first embodiment uses a (meth)acrylic monomer that contains an acryloyl group that has the possibility of increasing the adhesive force of the cured product.

Further, generally, in cases in which the hygroscopic property of a cured product is high, it is easy for breakage to occur at the regions of the cured product where moisture has been absorbed.

With regard to the above-described point, because the hydrophobic property of aromatic groups is high, due to the photocurable composition of the first embodiment using a (meth)acrylic monomer having an aromatic group, the hygroscopic property of the cured product that is obtained can be decreased, and the rupture elongation of the cured product can be improved well.

Further, by raising the aromatic ring concentration, the shock absorbing ability can be improved, and, by keeping the aromatic ring concentration low, the shock absorbing ability can be reduced.

From the above-described standpoint, the aromatic ring concentration in the (meth)acrylic monomer component is preferably greater than or equal to 0.00100 mol/g, and more preferably greater than or equal to 0.00250 mol/g, and even more preferably greater than or equal to 0.00450 mol/g.

From the standpoint of suppressing yellowing of the cured product, the upper limit of the aromatic ring concentration in the (meth)acrylic monomer component is preferably less than or equal to 0.010 mol/g, and more preferably less than or equal to 0.008 mol/g.

Examples of the aromatic group are phenyl group, phenylene group, naphthyl group, anthracene group, and the like.

Among the above, phenyl groups and phenylene groups are preferable are the aromatic group.

((Meth)Acrylic Monomer (A) Having Two (Meth)Acryloyl Groups)

It is preferable that the (meth)acrylic monomer component in the first embodiment contains (meth)acrylic monomer (A) that has two (meth)acryloyl groups.

(Meth)acrylic monomer (A) does not have a (meth) acryloyl group other than the two (meth)acryloyl groups.

One type or two or more types of (meth)acrylic monomer (A) may be used provided that the (meth)acrylic monomer (A) has two (meth)acryloyl groups.

It is preferable that (meth)acrylic monomer (A) be a (meth)acrylic monomer that has two (meth)acryloyloxy groups.

It is preferable that (meth)acrylic monomer (A) contain a urethane bond. Due thereto, the rupture elongation of the cured product that is obtained can be improved.

From the standpoints of the rupture elongation and the adhesive force of the cured product that is obtained, the number of urethane bonds contained in (meth)acrylic monomer (A) is preferably 1~5, and more preferably 2~4, and even more preferably 2.

By making large the (meth)acryloyl group equivalent amount of (meth)acrylic monomer (A) (i.e., by making the molecular weight of (meth)acrylic monomer (A) large), the shock absorbing ability can be improved, and, by making the (meth)acryloyl group equivalent amount small, the shock absorbing ability can be reduced.

Namely, by making the (meth)acryloyl group concentration (mol/g) of (meth)acrylic monomer (A) small, the shock absorbing ability can be improved, and, by making the (meth)acryloyl group concentration (mol/g) of (meth)acrylic monomer (A) large, the shock absorbing ability can be reduced.

From the above-described standpoints and the standpoint of improving the hardness of the cured product that is obtained, the (meth)acryloyl group concentration (mol/g) in (meth)acrylic monomer (A) is preferably 0.001 mol/g~0.01 mol/g, and more preferably to 0.001 mol/g~0.005 mol/g.

It is preferable that (meth)acrylic monomer (A) contains the compound expressed by following Formula (1).

Further, it is also preferable that (meth)acrylic monomer (A) is the compound expressed by following Formula (1).

[Chemical Formula 3]

Formula (1)

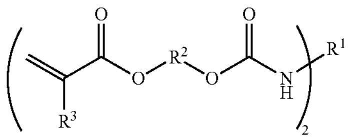

In Formula (1), $R^1$ and $R^2$ each independently represents a divalent linking group, and $R^3$ each independently is a methyl group or a hydrogen atom.

In above Formula (1), $R^1$ is preferably a divalent organic group, and is more preferably a divalent organic group that may have one or more selected from the group consisting of an aromatic structure, an alicyclic structure, an ether bond, an ester bond and a urethane bond.

In $R^1$ in Formula (1), the divalent organic group preferably contains a divalent chain hydrocarbon group, and more preferably contains a divalent chain hydrocarbon group and at least one group selected from the group consisting of divalent hydrocarbon groups having a ring structure and divalent groups containing a hetero atom.

Aromatic structures and alicyclic structures are examples of the aforementioned ring structure.

The divalent chain hydrocarbon group may be saturated or unsaturated, and may have a substituent. The divalent chain hydrocarbon group may be a straight-chain or branched-chain alkylene group.

From the standpoints of keeping down the viscosity of the photocurable composition, improving the rupture elongation of the cured product that is obtained, and keeping down the adhesive force of the cured product that is obtained, $R^1$ in Formula (1) preferably includes an oxyalkylene structure, a polyester structure.

Further, from standpoints similar to those described above, $R^1$ in Formula (1) is preferably a divalent chain hydrocarbon group that does not have a substituent.

In $R^1$ in Formula (1), the carbon number of the divalent organic group may be, for example, within the range of 5~2500, and is preferably within the range of 5~2000.

In $R^1$ in Formula (1), the divalent organic group may include a hetero atom. Examples of the aforementioned hetero atom include an oxygen atom, a nitrogen atom, and the like.

In $R^1$ in Formula (1), examples of the divalent hydrocarbon group having an aromatic structure include arylene group, alkylene arylene group, alkylene arylene alkylene group, arylene alkylene arylene group, and the like.

In $R^1$ in Formula (1), examples of the divalent hydrocarbon group having an alicyclic structure are cyclopropylene group, cyclobutylene group, cyclopentylene group, cyclohexylene group, cyclohexenylene group, cycloheptylene group, cyclooctylene group, cyclononylene group, cyclodecylene group, cycloundecylene group, cyclododecylene group, cyclotridecylene group, cyclotetradecylene group, cyclopentadecylene group, cyclooctadecylene group, cycloicosylene group, bicyclohexylene group, norbornylene group, isobornylene group, and adamantylene group.

$R^1$ in Formula (1) may have a substituent, and examples of the substituent include a direct chain or bifurcated chain alkyl group of a carbon number of 1~6.

In Formula (1), from the standpoints of restorability and shock absorbing ability, $R^1$ is preferably a divalent chain hydrocarbon group, or a group formed from a divalent chain hydrocarbon group and at least one group selected from the group consisting of divalent hydrocarbon groups having an alicyclic structure, divalent hydrocarbon groups having an aromatic structure, and divalent groups containing hetero atoms, and $R^1$ is more preferably a divalent chain hydrocarbon group, or a group formed from a divalent chain hydrocarbon group and at least one group selected from the group consisting of divalent hydrocarbon groups having an alicyclic structure and divalent groups containing hetero atoms.

From the standpoints of restorability and shock absorbing ability, the divalent hydrocarbon group having an aromatic structure is preferably the divalent hydrocarbon group expressed by following formula (1-a).

Further, also from the standpoints of suppressing yellowing of the cured product and improving weather resistance, the divalent hydrocarbon group having an aromatic structure is preferably the divalent hydrocarbon group expressed by following Formula (1-a).

[Chemical Formula 4]

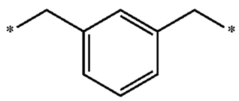

(1-a)

(In Formula (1-a), * represents a binding site.)

From the standpoints of restorability and shock absorbing ability, the aforementioned divalent group containing hetero atoms in $R^1$ preferably includes at least one bond selected from the group consisting of urethane bonds and ether bonds.

In above Formula (1), $R^2$ each independently is preferably a divalent chain hydrocarbon group that may have a substituent.

Divalent chain hydrocarbon groups that are suitable as $R^2$ are the same as the divalent chain hydrocarbon groups that are suitable as $R^1$. However, the divalent chain hydrocarbon groups that are used as $R^2$ preferably have a carbon number of 2~6, and more preferably have a carbon number of 2~3.

Further, from the standpoint of keeping down the viscosity, the divalent chain hydrocarbon groups that are used as $R^2$ preferably are a divalent chain hydrocarbon group having a carbon number of 2~6 and not having a substituent, and it is more preferable that the carbon number is 2~3.

In a case in which $R^2$ has a substituent, examples of the substituent are alkyl groups having a carbon number of 1~6 such as methyl group, ethyl group and the like; aryl groups; cycloalkyl groups having a carbon number of 3~6 such as cyclopentyl group, cyclohexyl group and the like; tolyl groups: xylyl groups: cumyl groups; styryl groups: alkoxyphenyl groups such as methoxyphenyl group, ethoxyphenyl group, propoxyphenyl group, and the like.

As the molecular weight of (meth)acrylic monomer (A), a weight average molecular weight of 600~30000 is preferable, and 800~20000 is more preferable, and 1000~5000 is even more preferable.

From the standpoints of restorability and shock absorbing ability, the aromatic ring concentration in (meth)acrylic monomer (A) is preferably less than or equal to 0.0020 mol/g, and more preferably less than or equal to 0.0016 mol/g.

The aromatic ring concentration in (meth)acrylic monomer (A) may be greater than or equal to 0.0010 mol/g for example.

(Molecular Weight Per One (Meth)Acryloyl Group)

The molecular weight per one (meth)acryloyl group in (meth)acrylic monomer (A) is preferably greater than or equal to 300 g/mol.

Due thereto, the rupture elongation of the cured product can be improved more.

From standpoints similar to those described above, the molecular weight per one (meth)acryloyl group in (meth) acrylic monomer (A) is more preferably greater than or equal to 600 g/mol.

Further, the molecular weight per one (meth)acryloyl group in (meth)acrylic monomer (A) is preferably less than or equal to 15000 g/mol, and more preferably less than or equal to 10000 g/mol, and even more preferably less than or equal to 2000 g/mol.

The molecular weight per one (meth)acryloyl group in (meth)acrylic monomer (A) is preferably 50 g/mol~15000 g/mol, and more preferably 150 g/mol~10000 g/mol, and even more preferably 250 g/mol~2000 g/mol.

Note that, in a case in which plural (meth)acrylic monomers are contained as (meth)acrylic monomer (A), the molecular weight per one (meth)acryloyl group is derived as the mass average value of the molecular weight of each (meth)acrylic monomer.

((Meth)Acrylic Monomer (B) Having One (Meth)Acryloyl Group)

It is preferable that the (meth)acrylic monomer component in the first embodiment contain (meth)acrylic monomer (B) that has one (meth)acryloyl group. (Meth)acrylic monomer (B) does not have a (meth)acryloyl group other than the one (meth)acryloyl group.

For (meth)acrylic monomer (B), one type or two or more types of acrylic monomers may be used provided that they are acrylic monomers having one (meth)acryloyl group.

It is preferable that (meth)acrylic monomer (B) contain a ring structure. Due thereto, the hardness of the cured product that is obtained can be improved, and the adhesive force of the cured product that is obtained can be kept down.

As the ring structure, aromatic structures and alicyclic structures are preferable, and aromatic structures are more preferable.

In a case in which (meth)acrylic monomer (B) contains an aromatic structure, the number of aromatic rings contained in (meth)acrylic monomer (B) is preferably 1~4, and 2 and 3 are more preferable.

It is preferable that (meth)acrylic monomer (B) be the compound expressed by following Formula (2) or (3), and the compound expressed by following Formula (2) is more preferable.

[Chemical Formula 5]

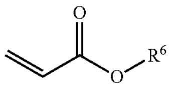

(2)

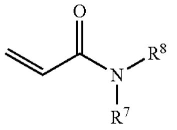

(3)

In Formula (2), $R^6$ is a monovalent organic group that may have a ring structure.

In Formula (3), $R^7$ and $R^8$ each independently is a monovalent organic group that may have a ring structure, or a hydrogen atom, and $R^7$ and $R^8$ may bind together and form a ring.

(Meth)acrylic monomer (B) is preferably the compound expressed by Formula (2), and $R^6$ is preferably a monovalent organic group that has a ring structure (or an aromatic ring structure) and a carbon number of 3~30, and is more preferably a monovalent organic group that has a ring structure (or an aromatic ring structure) and a carbon number of 6~20.

In Formula (2), $R^6$ may be the structure expressed by following Formula (4).

$$*\text{-}L_1\text{-}A \quad (4)$$

In Formula (4), Li is a divalent chain hydrocarbon group of a carbon number of 1~30 that may have a single bond or a hetero atom that is O or N. A is a monovalent alicyclic group of a carbon number of 3~30 that may have a hydrogen atom or a hetero atom that is 0 or N, or is an aryl group of a carbon number of 6~30. * represents a binding site.

The divalent chain hydrocarbon group of a carbon number of 1~30 that may have a hetero atom that is O or N that is represented by $L_1$ in Formula (4) may be a straight-chain form or a branched-chain form.

In $L_1$, the carbon number is preferably 1~20, and is more preferably 1~10, and is even more preferably 1~8.

In a case in which $L_1$ contains a hetero atom, the number of hetero atoms is preferably 1~6, and is more preferably 1 or 2.

$L_1$ may have a substituent. Suitable examples of the substituent of $L_1$ include alkyl groups of a carbon number of 1~3, hydroxy groups, and alkyl groups having a carbon number of 1~3 and in which one or two of the hydrogen atoms is substituted with a hydroxy group.

$L_1$ may contain a urethane bond. In a case in which $L_1$ contains a urethane bond, the number of urethane bonds is 1 or 2.

Examples of the monovalent alicyclic group of a carbon number of 3~20 that may have a hetero atom that is O or N that is represented by A in Formula (4) include cyclopropyl group, cyclobutyl group, cyclopentyl group, cyclohexyl group, cyclohexenyl group, cycloheptyl group, cyclooctyl group, cyclononyl group, cyclodecyl group, cycloundecyl group, cyclododecyl group, cyclotridecyl group, cyclotetradecyl group, cyclopentadecyl group, cyclooctadecyl group, cycloicosyl group, bicyclohexyl group, norbornyl group, isobornyl group, adamantyl group, morpholyl group, piperidino group, piperazino group, and dioxane group. The carbon number of the monovalent alicyclic group is preferably 5~12, and is more preferably 6~10.

Examples of the aromatic structure represented by A in Formula (4) include phenyl structures, biphenyl structures, naphthyl structures, and anthryl structures.

A may have a substituent. Suitable examples of the substituent of A include are alkyl groups having a carbon number of 1~6 such as methyl group, ethyl group and the like; hydroxy groups; alkyl groups having a carbon number of 1~6 and in which one or two of the hydrogen atoms are substituted with a hydroxy group; aryl groups; cycloalkyl groups having a carbon number of 3~6 such as cyclopentyl group, cyclohexyl group and the like; tolyl groups: xylyl groups: cumyl groups; styryl groups: alkoxyphenyl groups such as methoxyphenyl groups, ethoxyphenyl groups, propoxyphenyl groups, and the like.

In Formula (2), the total carbon number of $\text{-}L_1\text{-}A$ is preferably 1~30, and more preferably 1~20.

In Formula (3), $R^7$ and $R^8$ each independently is a monovalent organic group that may have a ring structure, or a hydrogen atom, and $R^7$ and $R^8$ may bind together and form a ring.

Examples of suitable $R^7$ and $R^8$ are monovalent hydrocarbon groups of a carbon number of 1~30 that may have a hetero atom that is O or N. This hydrocarbon group may be a straight-chain form or a branched-chain form, and may be saturated or unsaturated, and may have a substituent.

For $R^7$ and $R^8$, the carbon number is preferably 1~20, and is more preferably 1~10.

Examples of the organic group in $R^7$ and $R^8$ include alkyl groups of a carbon number of 1~30 such as methyl group, ethyl group, propyl group and the like that may have a hetero atom that is O or N. Among these, it is preferable that either one of $R^7$ and $R^8$ is a hydroxyethyl group or a butoxymethyl group, and the other is a hydrogen atom.

In a case in which either one of $R^7$ and $R^8$ is a hydroxyethyl group or a butoxymethyl group, and the other is a hydrogen atom, the following is an example of (meth)acrylic monomer (B).

The following is an example of (meth)acrylic monomer (B) in a case in which $R^7$ and $R^8$ bind together and form a ring.

[Chemical Formula 6]

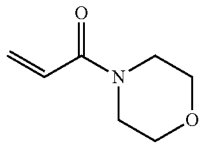

The molecular weight of (meth)acrylic monomer (B) is not particularly limited, but the weight average molecular weight is preferably 80~500, and is more preferably 100~400, and is even more preferably 130~320.

Examples of compounds that are suitable as (meth)acrylic monomer (B) include compounds that are used in the Examples that are described hereafter.

In the photocurable composition of the first embodiment, it is preferable that at least one of (meth)acrylic monomer (A) and (meth)acrylic monomer (B) has a ring structure.

Due thereto, the rupture elongation of the cured product that is obtained can be improved more, and the adhesive force of the cured product that is obtained can be kept down.

Examples of the aforementioned ring structure are aromatic groups and alicyclic groups and the like.

In the photocurable composition of the first embodiment, it is preferable that at least one of (meth)acrylic monomer (A) and (meth)acrylic monomer (B) has an aromatic group.

As described above, due to at least one of (meth)acrylic monomer (A) and (meth)acrylic monomer (B) having an aromatic group, the adhesive force of the cured product that is obtained can be kept down well.

Further, due to the photocurable composition of the first embodiment using a (meth)acrylic monomer that has an aromatic group, the moisture absorbing ability of the cured product that is obtained can be reduced, and the rupture elongation of the cured product can be improved well.

In the photocurable composition of the first embodiment, it is preferable that the content of (meth)acrylic monomer (A), with respect to a total content of 1000 parts by mass of (meth)acrylic monomer (A) and (meth)acrylic monomer (B), be 250 parts by mass~800 parts by mass, and more preferably 350 parts by mass~650 parts by mass, and even more preferably 380 parts by mass~500 parts by mass.

In the photocurable composition of the first embodiment, the total content of (meth)acrylic monomer (A) and (meth) acrylic monomer (B) in the (meth)acrylic monomer component is preferably greater than or equal to 90% by mass, and more preferably greater than or equal to 95% by mass.

The photocurable composition of the first embodiment may contain acrylic rubber particles. In a case in which the photocurable composition of the first embodiment contains acrylic rubber particles, the content of the acrylic rubber particles in the photocurable composition of the first embodiment is preferably 0.1% by mass~30% by mass. Further, in a case in which the photocurable composition of the first embodiment contains acrylic rubber particles, the total content of (meth)acrylic monomer (A), (meth)acrylic monomer (B), and the acrylic rubber particles in the (meth) acrylic monomer component is preferably greater than or equal to 90% by mass, and more preferably greater than or equal to 95% by mass.

Because (meth)acrylic monomer (A) and (meth)acrylic monomer (B) in the first embodiment improve the tensile elongation of the cured product and can lower the adhesive force, Z in following Formula a, which is derived by using the molecular weight (g/mol) of (meth)acrylic monomer (A) per one (meth)acryloyl group [i.e., molecular weight of (meth)acrylic monomer (A)/number of (meth)acryloyl groups in (meth)acrylic monomer (A)] and the aromatic ring concentration (mol/g) in the (meth)acrylic monomer component, is preferably 0.00100~100, and more preferably 0.200~50.

$$Z=X\times Y \qquad \text{Formula } \alpha$$

X (g/mol): (molecular weight of (meth)acrylic monomer (A) per one (meth)acryloyl group)−200

Y (mol/g): (aromatic ring concentration (mol/g) in the (meth)acrylic monomer component)−0.00100

Because (meth)acrylic monomer (A) and (meth)acrylic monomer (B) in the first embodiment improve the tensile elongation of the cured product and can lower the adhesive force, and moreover can improve the restorability, Z1 in following Formula β, which is derived by using the molecular weight (g/mol) of (meth)acrylic monomer (A) per one (meth)acryloyl group and the aromatic ring concentration (mol/g) in the (meth)acrylic monomer component, is preferably $5\times10^3$~$500\times10^4$, and more preferably $1\times10^4$~$100\times10^4$.

Further, the upper limits of the numerical values of these ranges are preferable also from the standpoint of improving the shapeability (e.g., the surface roughness and the like).

The lower limits of the numerical values of these ranges are preferable also from the standpoint of suppressing yellowing.

$$Z1=X1/Y1 \qquad \text{Formula } \beta$$

X1 (g/mol): molecular weight of (meth)acrylic monomer (A) per one (meth)acryloyl group Y1 (mol/g): aromatic ring concentration (mol/g) in the (meth)acrylic monomer component The photocurable composition of the first embodiment preferably satisfies at least one of following (a) and following (b).

(a) (Meth)acrylic monomer (A) contains (meth)acrylic monomer (A-1) in which the molecular weight per one (meth)acryloyl group is greater than or equal to 300 g/mol and is less than or equal to 600 g/mol, and (meth)acrylic monomer (A-2) in which the molecular weight per one (meth)acryloyl group is greater than 600 g/mol and is less than or equal to 15000 g/mol.

(b) (Meth)acrylic monomer (B) contains (meth)acrylic monomer (B-1) having two aromatic rings, and (meth) acrylic monomer (B-2) having one aromatic ring.

Due to the photocurable composition of the first embodiment satisfying at least one of (a) and (b), the balance among the adhesive force, the rupture elongation and the shock resistance is good, and moreover, the restorability improves.

Examples of (meth)acrylic monomer (A-1) in which the molecular weight per one (meth)acryloyl group is greater than or equal to 300 g/mol and is less than or equal to 600 g/mol include AH-600 (manufactured by Kyoeisha Chemical Co., Ltd.), MMD-352 that is described later, and the like.

Examples of (meth)acrylic monomer (A-2) in which the molecular weight per one (meth)acryloyl group is greater than 600 g/mol and is less than or equal to 15000 g/mol include UA-160TM (manufactured by Shin Nakamura Chemical Co. Ltd.), UA-122P (manufactured by Shin Nakamura Chemical Co. Ltd.), UN-2700 (manufactured by Negami Chemical Industrial Co., Ltd.), UN-2600 (manufactured by Negami Chemical Industrial Co., Ltd.), UN-352 (manufactured by Negami Chemical Industrial Co., Ltd.), Ebecryl 8402 (manufactured by Daicell Allnex Ltd.) and Ebecryl 230 (manufactured by Daicell Allnex Ltd.) that are described later, and the like.

The content of (meth)acrylic monomer (A-1), with respect to a total content of 1000 parts by mass of (meth) acrylic monomer (A) and (meth)acrylic monomer (B), is preferably 50 parts by mass~450 parts by mass, and more preferably 80 parts by mass~350 parts by mass, and even more preferably 100 parts by mass~250 parts by mass.

The content of (meth)acrylic monomer (A-2), with respect to a total content of 1000 parts by mass of (meth) acrylic monomer (A) and (meth)acrylic monomer (B), is preferably 200 parts by mass~850 parts by mass, and more preferably 220 parts by mass~650 parts by mass, and even more preferably 250 parts by mass~500 parts by mass.

Note that, in cases in which the photocurable composition of the first embodiment contains only either one of (meth) acrylic monomer (A-1) and (meth)acrylic monomer (A-2), and in cases in which both are contained, it is preferable for the contents of (meth)acrylic monomer (A-1) and (meth) acrylic monomer (A-2) to fall in the above-described ranges.

The proportion of the content of (meth)acrylic monomer (A-1) with respect to the total content of (meth)acrylic monomer (A-1) and (meth)acrylic monomer (A-2) is preferably 10% by mass~70% by mass, and more preferably 15% by mass~50% by mass, and even more preferably 20% by mass~40% by mass.

Examples of (meth)acrylic monomer (B-1) having two aromatic rings are POBA (manufactured by Kyoeisha Chemical Co., Ltd.), HRD01 (manufactured by Nisshoku Techno Fine Chemical Co., Ltd.), M110 (manufactured by Toagosei Co., Ltd.), and the like.

Examples of (meth)acrylic monomer (B-2) having one aromatic ring are PO-A (manufactured by Kyoeisha Chemical Co., Ltd.), M113 (manufactured by Toagosei Co., Ltd.), P2H-A (manufactured by Kyoeisha Chemical Co., Ltd.), BZ (manufactured by Kyoeisha Chemical Co., Ltd.), M-600A (manufactured by Kyoeisha Chemical Co., Ltd.), PO (manufactured by Kyoeisha Chemical Co., Ltd.), M111 (manufactured by Toagosei Co., Ltd.), and the like.

The content of (meth)acrylic monomer (B-1), with respect to a total content of 1000 parts by mass of (meth)acrylic monomer (A) and (meth)acrylic monomer (B), is preferably 100 parts by mass~600 parts by mass, and more preferably 150 parts by mass~500 parts by mass, and even more preferably 200 parts by mass~450 parts by mass.

The content of (meth)acrylic monomer (B-2), with respect to a total content of 1000 parts by mass of (meth)acrylic monomer (A) and (meth)acrylic monomer (B), is preferably 100 parts by mass~600 parts by mass, and more preferably 150 parts by mass~500 parts by mass, and even more preferably 200 parts by mass~450 parts by mass.

Note that, in cases in which the photocurable composition of the first embodiment contains only either one of (meth) acrylic monomer (B-1) and (meth)acrylic monomer (B-2), and in cases in which both are contained, it is preferable for the contents of (meth)acrylic monomer (B-1) and (meth) acrylic monomer (B-2) to fall in the above-described ranges.

The content of (meth)acrylic monomer (B-1) with respect to the total content of (meth)acrylic monomer (B-1) and (meth)acrylic monomer (B-2) is preferably 20% by mass 80% by mass, and more preferably 30% by mass~70% by mass, and even more preferably 40% by mass~60% by mass.

(Other Additives in the (Meth)Acrylic Monomer Component)

The (meth)acrylic monomer component of the first embodiment may contain other additives other than above-described (meth)acrylic monomer (A) and above-described (meth)acrylic monomer (B).

Examples of the other additives include trifunctional (meth)acrylic monomers and the like.

Among the above, trifunctional (meth)acrylic monomers can lower the adhesive force of the cured product. On the other hand, because there is the possibility that trifunctional (meth)acrylic monomers will lower the rupture elongation of the cured product, it is preferable that only a small amount thereof be added within a range that is such that the rupture elongation can be maintained.

(Photopolymerization Initiator)

The photocurable composition of the first embodiment contains a photopolymerization initiator.

The photopolymerization initiator is not particularly limited provided that it generates radicals due to the illumination of light, but is preferably a photopolymerization initiator that generates radicals at the wavelength of the light that is used at the time of stereolithography.

An example of the wavelength of the light that is used at the time of stereolithography is generally 365 nm~500 nm, but, in actual practice, 365 nm~430 nm is preferable, and 365 nm~420 nm is more preferable.

Examples of photopolymerization initiators that generate radicals at the wavelength of the light that is used at the time of stereolithography include alkylphenone compounds, acylphosphine oxide compounds, titanocene compounds, oxime ester compounds, benzoin compounds, acetophenone compounds, benzophenone compounds, thioxanthone compounds, α-acyloxime ester compounds, phenylglyoxylate compounds, benzil compounds, azo compounds, diphenyl sulfide compounds, organic dye compounds, iron—phthalocyanine compounds, benzoin ether compounds, anthraquinone compounds, and the like.

Thereamong, from the standpoints of reactivity and the like, alkylphenone compounds and acylphosphine oxide compounds are preferable.

Examples of alkylphenone compounds include 1-hydroxycyclohexyl phenyl ketone (Omnirad 184: manufactured by IGM Resins).

Examples of acylphosphine oxide compounds include bis(2,4,6-trimethylbenzoyl)phenylphosphine oxide (Omnirad 819: manufactured by IGM Resins), and 2,4,6-trimethylbenzoyl-diphenyl-phosphine oxide (Omnirad TPO: manufactured by IGM Resins).

The photocurable composition of the first embodiment may contain only one type of photopolymerization initiator, or may contain two or more types.

The content (in the case of two or more types, the total content) of the photopolymerization initiator in the photocurable composition of the first embodiment is preferably 0.1% by mass~10% by mass, and more preferably 0.2% by mass~5% by mass, and even more preferably 0.3% by mass~3% by mass.

<Other Components>

The photocurable composition of the first embodiment may contain, as needed, one or more types of other components that are other than (meth)acrylic monomer (A), (meth)acrylic monomer (B), and a photopolymerization initiator.

In a case in which the photocurable composition contains the aforementioned other components, the total mass of (meth)acrylic monomer (A), (meth)acrylic monomer (B) and the photopolymerization initiator, with respect to the total amount of the photocurable composition, is preferably greater than or equal to 30% by mass, and more preferably greater than or equal to 50% by mass, and even more preferably greater than or equal to 70% by mass, and yet more preferably greater than or equal to 80% by mass, and still yet more preferably greater than or equal to 90% by mass, and particularly preferably greater than or equal to 95% by mass.

Examples of the other components include monomers other than (meth)acrylic monomer (A) and (meth)acrylic monomer (B).

In a case in which the photocurable composition contains monomer(s) other than (meth)acrylic monomer (A) and (meth)acrylic monomer (B) as other component(s), the content of the monomer(s) that is/are the other component(s) is, with respect to the total of (meth)acrylic monomer (A) and (meth)acrylic monomer (B), preferably less than or equal to 50% by mass, and more preferably less than or equal to 30% by mass, and even more preferably less than or equal to 20% by mass, and particularly preferably less than or equal to 10% by mass.

Examples of the other components are additives such as coloring materials, coupling agents such as silane coupling agents (e.g., 3-acryloxypropyltrimethoxysilane) and the like, rubber agents, ion trapping agents, ion exchange agents, leveling agents, plasticizers, antifoaming agents and the like, and thermal polymerization initiators.

In a case in which the photocurable composition of the first embodiment contains a thermal polymerization initiator, photocuring and heat curing can be used in combination. Examples of the thermal polymerization initiator include heat radical generators, amine compounds, and the like.

The method of preparing the photocurable composition of the first embodiment is not particularly limited, and an example thereof is a method of mixing-together (meth) acrylic monomer (A) and (meth)acrylic monomer (B), and a photopolymerization initiator (and other components as needed).

The means for mixing the respective components together is not particularly limited, and examples include means such as dissolution by ultrasonic waves, a dual arm type mixer, a roll kneader, a twin-screw extruder, a ball mill kneader, a planetary mixer, and the like.

The photocurable composition of the present embodiment may be prepared by, after the respective components are mixed together, removing impurities by filtering by a filter, and moreover, carrying out a vacuum defoaming treatment.

<<Cured Product>>

The method of carrying out photocuring by using the photocurable composition of the first embodiment is not particularly limited, and all known methods and devices can be used. An example is a method in which by repeating, plural times, a step of forming a thin film that is formed from the photocurable composition of the first embodiment, and a step of illuminating light onto the thin film and obtaining a cured layer, plural cured layers are layered, and a cured product of a desired shape is fabricated. Note that the cured product that is obtained may be used as is, or may be further subjected to post-curing by light illumination, heating or the like, or the like, and used after the physical characteristics, the shape stability and the like thereof have been improved.

<Stereolithography>

The photocurable composition of the first embodiment is preferably used in stereolithography.

Thereamong, the photocurable composition of the first embodiment can be suitably used in shaping methods that use a 3D printer.

In the present disclosure, stereolithography is one type of three-dimensional shaping method using a 3D printer.

<3D Printer>

Examples of stereolithographic techniques include an SLA (Stereo Lithography Apparatus) technique, a DLP (Digital Light Processing) technique, an inkjet technique, and the like.

The photocurable composition of the present embodiment is particularly suited to stereolithography by an SLA technique or a DLP technique.

An example of an SLA technique is a technique in which a three-dimensional shaped product is obtained by illuminating ultraviolet laser light in the form of spots onto a photocurable composition.

In the case of fabricating a dental product or the like by an SLA technique, for example, it suffices to store the photocurable composition of the present embodiment in a container, cure the photocurable composition by selectively illuminating ultraviolet laser light that is in the form of spots such that the desired pattern is obtained on the liquid surface of the photocurable composition, form a cured layer of the desired thickness on a shaping table, and next, repeat a layering operation of lowering the shaping table, supplying the photocurable composition of one layer that is in liquid form onto the cured layer, and carrying out curing in the same way so as to obtain continuous cured layers. Due thereto, a dental product or the like can be fabricated.

An example of a DLP technique is a technique in which a three-dimensional shaped product is obtained by illuminating light in a planar form onto a photocurable composition.

Suitable reference can be made to, for example, Japanese Patent No. 5111880 and Japanese Patent No. 5235056 for methods of obtaining a three-dimensional shaped product by a DLP technique.

In a case in which a dental product or the like is fabricated by a DLP technique, for example, it suffices to use, as the light source, a lamp that illuminates light other than laser light such as a high pressure mercury lamp, an ultrahigh pressure mercury lamp, a low pressure mercury lamp or the like, or LEDs or the like, and place a planar drawing mask, at which plural digital micromirror shutters are disposed in a planar form, between the light source and the shaping surface of the photocurable composition, and illuminate light onto the shaping surface of the photocurable composition via the aforementioned planar drawing mask, and successively layer cured layers having predetermined shape patterns. Due thereto, a dental product or the like can be fabricated.

An example of an inkjet technique is a technique in which a three-dimensional shaped product is obtained by continuously discharging liquid drops of a photocurable composition onto a substrate from an inkjet nozzle, and illuminating light onto the liquid drops that have adhered to the substrate.

In a case of fabricating a dental product or the like by an inkjet technique, for example, it suffices to discharge the photocurable composition out onto the substrate from an inkjet nozzle while a head, which has the inkjet nozzle and a light source, is scanned within a plane, and illuminate light onto the discharged photocurable composition such that a cured layer is formed, and repeat these operations such that cured layers are successively layered. Due thereto, a dental product or the like can be fabricated.

<<Dental Product>>

The photocurable composition of the first embodiment is suitably used in fabricating dental products by stereolithography.

Further, the photocurable composition of the first embodiment is suitably used in fabricating mouthpieces, gingiva masks and lining materials by stereolithography, and is more suitably used in fabricating mouthpieces and gingiva masks.

The dental product of the first embodiment preferably contains a cured product of the photocurable composition of the first embodiment.

The dental product that contains a cured product (i.e., a photoshaped product) of the photocurable composition of the first embodiment is not particularly limited, and can be used as artificial teeth, prostheses, medical appliances that are used within the oral cavity, molds (gingiva masks and the like) and the like, and appliances that are used within the oral cavity or molds are preferable, and usage for mouthpieces (in particular, mouthpieces for sports), for gingiva masks and for lining materials is more preferable, and usage for mouthpieces (in particular, mouthpieces for sports) and for gingiva masks is even more preferable. It is preferable to use a cured product of the photocurable composition of the first embodiment in at least a part of the dental product. Examples of appliances that are used within the oral cavity include mouthpieces for sports, mouthguards, mouthpieces for orthodontics, splints such as splints for occlusal adjustment and splints for temporomandibular joint arthrosis treatments and the like, and mouthpieces used in treatments for sleep apnea syndrome.

By using a cured product of the photocurable composition of the first embodiment, a medical appliance having an excellent usage sensation at the time of use within the oral cavity and sufficient strength and hardness can be manufactured.

<Method of Manufacturing Mouthguard and Mouthguard>

In a case in which the dental product of the first embodiment is a mouthguard, the mouthguard is preferably manufactured by stereolithography.

As a method of manufacturing a mouthguard in the first embodiment, the mouthguard is preferably manufactured by stereolithography having a step of preparing three-dimensional image data of a mouthguard at which the thickness of the occlusal surface of the central incisor portion is greater than or equal to 1.5 times the thickness of the occlusal surface of the second molar portion.

The mouthguard of the first embodiment is a photoshaped product, and the thickness of the occlusal surface of the central incisor portion is preferably greater than or equal to 1.5 times the thickness of the occlusal surface of the second molar portion.

Conventionally, fabrication of a mouthguard is generally carried out by using a suction molding machine by using a commercially available sheet for a mouthguard. In this case, the thickness of the occlusal surface of the mouthguard tends to be uniform, and a long time is needed in order to adjust the occlusal surface. Further, although it is possible to place plural sheets at specific regions and adjust the thicknesses, in fabricating a mouthguard, the setting of conditions is difficult, and skill on the part of the worker and a long time are required.

In the first embodiment, at the time of fabricating a mouthguard by a 3D printer by using a photocurable composition, CAD design is carried out with the thickness of the occlusal surface of the central incisor portion in the three-dimensional image data of the mouthguard being set to be, as compared with the thickness of the occlusal surface of the second molar portion, preferably greater than or equal to 1.5 times and less than or equal to 5 times, and more preferably greater than or equal to 2 times and less than or equal to 4 times, and, by fabricating the mouthguard by stereolithography using a 3D printer, adjustment of the occlusal surface is unnecessary or is simple, and the time for fabricating the mouthguard can be shortened greatly.

The central incisor portions of the mouthguard are the regions on the mouthguard that correspond to the central incisors of the teeth, and are the regions on the mouthguard that contact the central incisors when the mouthguard is worn.

The second molar portions of the mouthguard are the regions on the mouthguard that correspond to the second molars of the teeth, and are the regions on the mouthguard that contact the second molars when the mouthguard is worn.

Further, a central incisor portion and a second molar portion as two parts exist at each of the left and the right at each of the upper jaw and the lower jaw (i.e., there are four parts in total of central incisor portions and second molar portions at each of the upper jaw and the lower jaw).

Among the above-described central incisor portions and second molar portions, at at least one central incisor portion and second molar portion, the thickness of the occlusal surface of the central incisor portion may be greater than or equal to 1.5 times the thickness of the occlusal surface of the second molar portion, or, at all of the central incisor portions and the second molar portions, the thicknesses of the occlusal surfaces of the central incisor portions may be greater than or equal to 1.5 times the thicknesses of the occlusal surfaces of the second molar portions, or the average value of the thicknesses of the occlusal surfaces of all of the central incisor portions may be greater than or equal to 1.5 times the average value of the thicknesses of the occlusal surfaces of all of the second molar portions.

In a case in which the thickness of the occlusal surface of the central incisor portion is greater than or equal to 1.5 times the thickness of the occlusal surface of the second molar portion, at the time of biting, it is easy to make the central incisor contact the mouthguard, and therefore, great adjustment of the bite is unnecessary.

Further, in a case in which the thickness of the occlusal surface of the central incisor portion is less than or equal to 5 times the thickness of the occlusal surface of the second molar portion, it is easy to make the second molar contact the mouthguard, and therefore, great adjustment of the bite is unnecessary.

Further, the thickness of the occlusal surface of the second molar portion is preferably 0.2 mm 5 mm, and more preferably 0.5 mm~4 mm.

In a case in which the thickness of the occlusal surface of the second molar portion is greater than or equal to 0.2 mm, the strength of the mouthguard can be maintained well.

Further, in a case in which the thickness of the occlusal surface of the second molar portion is less than or equal to 5 mm, the extent of opening is suppressed, and the wearer feeling an unpleasant sensation can be suppressed.

The thickness of the occlusal surface means the thickness of the mouthguard at the occlusal surface of a specific tooth at the time when the mouthguard is worn. Specifically, this means the shortest distance among the distance between the surface contacting the distal end portion of the tooth and the opposing surface that opposes the surface that contacts the distal end portion of that tooth, at a tooth portion of the mouthguard that is a portion that contacts a tooth at the time when the mouthguard is being worn.

In other words, the thickness of the occlusal surface means the thickness of the thinnest portion among the portions of the mouthguard that are bit between a tooth and a tooth at the time when the mouthguard is being worn.

Note that opposing surface means the surface, at the mouthguard, that opposes the surface that contacts the distal end portion of the tooth.

FIG. 1 is a drawing showing drawing showing the external appearance of a mouthguard for the upper jaw in an embodiment of the present disclosure.

As shown in FIG. 1, a mouthguard 10 for the upper jaw in an embodiment of the present disclosure has second molar portions 1 that guard the second molars at the upper jaw side, and central incisor portions 2 that guard the central incisors at the upper jaw side.

Figure 2:
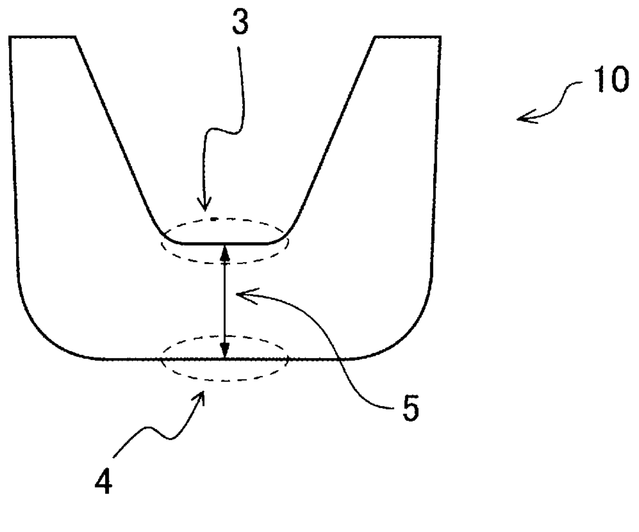
FIG. 2 is a drawing depicting the thickness of the mouthguard for the upper jaw at the occlusal surface (planar type) of a central incisor portion.

FIG. 2 is a drawing showing the thickness of the mouthguard for the upper jaw at the occlusal surface (planar type) of the central incisor portion.

Figure 3:
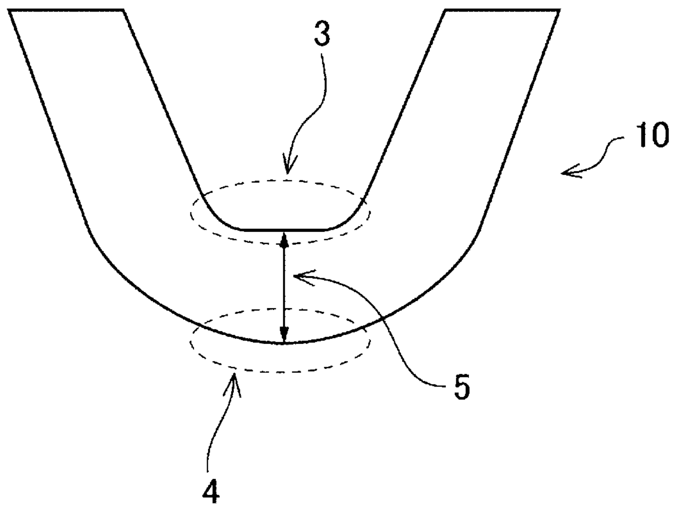
FIG. 3 is a drawing depicting g the thickness of the mouthguard for the upper jaw at the occlusal surface (non-planar type) of the central incisor portion.

FIG. 3 is a drawing showing the thickness of the mouthguard for the upper jaw at the occlusal surface (non-planar type) of the central incisor portion.

Note that the occlusal surface in a case in which the occlusal surface is planar is called occlusal surface (planar type). The occlusal surface in a case in which the occlusal surface is not planar is called occlusal surface (non-planar type).

For example, as shown in FIG. 2 and FIG. 3, thickness 5 of the occlusal surface at the central incisor portion indicates, at a central incisor portion of the mouthguard 10 for the upper jaw that is a portion that contacts a central incisor at the time when the mouthguard 10 for the upper jaw is being worn, the shortest distance among the distances between surface 3 that contacts the distal end portion of the central incisor, and opposing surface 4 that, at the aforementioned central incisor portion, opposes the surface 3 that contacts the distal end portion of the central incisor.

Figure 4:
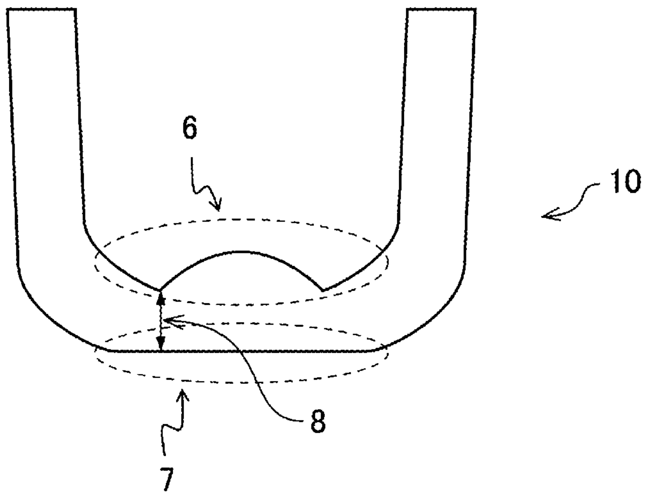
FIG. 4 is a drawing depicting the thickness of the mouthguard for the upper jaw at the occlusal surface (planar type) of a second molar portion.

FIG. 4 is a drawing showing the thickness of the mouthguard for the upper jaw at the occlusal surface (planar type) of a second molar portion.

Figure 5:
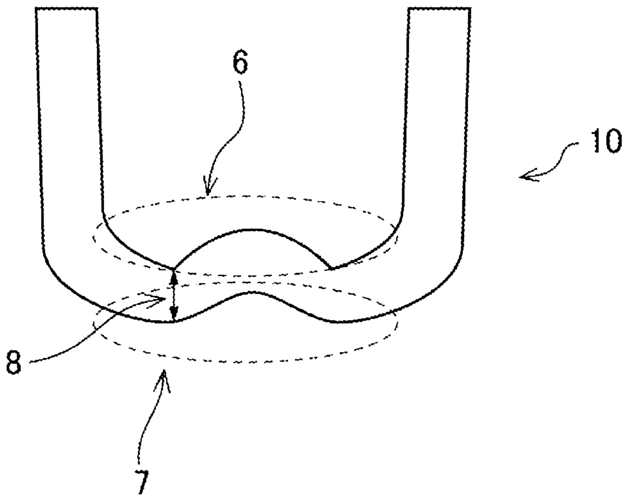
FIG. 5 is a drawing depicting the thickness of the mouthguard for the upper jaw at the occlusal surface (non-planar type) of the second molar portion.

FIG. 5 is a drawing showing the thickness of the mouthguard for the upper jaw at the occlusal surface (non-planar type) of the second molar portion.

For example, as shown in FIG. 4 and FIG. 5, thickness 8 of the occlusal surface at the second molar portion indicates, at a second molar portion of the mouthguard 10 for the upper jaw that is a portion that contacts a second molar at the time when the mouthguard 10 for the upper jaw is being worn, the shortest distance among the distances between surface 6 that contacts the distal end portion of the second molar, and opposing surface 7 that, at the aforementioned second molar portion, opposes the surface 6 that contacts the distal end portion of the second molar.

Moreover, at a mouthguard that is fabricated by a 3D printer by using the method of the first embodiment, the thickness can be freely changed by CAD design. Improvement in the wearing sensation can be devised by carrying out designing such as making only molar portion side surfaces thin, or the like.

The photocurable composition that is used in the present method of manufacturing a mouthguard is not limited to the photocurable composition of the first embodiment, and any photocurable composition can be used provided that it is a composition that can be photoshaped.

A mouthguard that is manufactured by the present method of manufacturing a mouthguard indicates an appliance that is used within the oral cavity and is structured so as to cover teeth and gums. The manufactured mouthguard is not particularly limited, and a mouthguard for the upper jaw is preferable.

Photocurable Composition of Second Embodiment

Following Form 2a and 2b are examples of the photocurable composition of the second embodiment.

<<Form 2a>>

The photocurable composition relating to Form 2a of the second embodiment contains a (meth)acrylic monomer component and a photopolymerization initiator, and the adhesive force of the cured product is less than or equal to 1.5 N, and the shore A hardness of the cured product is less than or equal to 97.

The inventors of the present disclosure thought that a cause of unpleasant sensations arising in cases in which a cured product obtained by photocuring a photocurable composition (hereinafter also simply called cured product) is applied to human bodies is the hardness of the cured product.

For example, in a case in which a cured product is used as a mouthpiece, a strong occlusal force is imparted via the mouthpiece to the contacting surfaces of the mouthpiece and the upper and lower teeth, due to biting of the teeth. It is thought that, at this time, in a case in which the hardness of the cured product is high, it is easier for the aforementioned occlusal force to be transferred to the teeth, and therefore, an unpleasant sensation such as pain or the like arises.

On the other hand, the inventors of the present disclosure discovered that, in a case in which the hardness of a cured product is made to be low, the adhesive force of the cured product is high, and this is a cause of deteriorating the handleability.

Namely, from the standpoint of obtaining a cured product in which unpleasant sensations can be suppressed at the time of application to a human body, and that has excellent handleability, it is important to specify the hardness of the cured product that is obtained by photocuring a photocurable composition to within a range in which unpleasant sensations can be suppressed, and to keep down the adhesive force of the cured product.

Due to the photocurable composition of Form 2a containing a (meth)acrylic monomer component and a photopolymerization initiator, and the adhesive force of the cured product being less than or equal to 1.5 N, and the shore A hardness of the cured product being less than or equal to 97, in a case in which the photocurable composition of the second embodiment is photocured, it is possible to obtain a cured product in which unpleasant sensations at the time of application to human bodies is suppressed and that has excellent handleability.

Details of preferable ranges, definitions, measuring methods and the like of the adhesive force of the cured product of the second embodiment are similar to the details of preferable ranges, definitions, measuring methods and the like that are put forth in the <Adhesive Force of Cured Product> in the above-described first embodiment.

(Hardness (Shore A Hardness) of Cured Product)

The shore A hardness of a cured product of the photocurable composition of Form 2A is less than or equal to 97.

By making the shore A hardness of the cured product be less than or equal to 97, unpleasant sensations at the time of applying the cured product to human bodies are suppressed.

Further, there is the general trend that, the lower the hardness of the cured product, the easier it is for the adhesive force to increase. However, in a case of using the photocurable composition of the second embodiment, the adhesive force of the cured product can be kept down even if the hardness of the cured product that is obtained is less than or equal to 97.

From standpoints that are similar to those described above, the shore A hardness of the cured product is preferably less than or equal to 95, and more preferably less than or equal to 93.

Further, the hardness of a cured product of the photocurable composition of Form 2a is preferably greater than or equal to 50.

There is the general trend that, the lower the hardness of (i.e., the softer) a cured product, the easier it is for the adhesive force to increase. However, by making the hardness of the cured product be greater than or equal to 50, the adhesive force of the cured product can be kept down even better.

From standpoints that are similar to those described above, the hardness of a cured product of the photocurable composition of Form 2a is more preferably greater than or equal to 66, and even more preferably greater than or equal to 80.

Note that, in the present disclosure, the hardness of the cured product is measured by the following method.

First, by illuminating visible light onto the photocurable composition by using a 3D printer, the photocurable composition is shaped to length 25 mm×width 25 mm×thickness 6 mm, and a shaped product (layered width 50 μm) is obtained. In the aforementioned illuminating of the visible light using the 3D printer, visible light of a wavelength of 405 nm is illuminated onto the respective layers within a range of 5.0 $mJ/cm^2$~10 $mJ/cm^2$ and under the condition of becoming a desired thickness.

By illuminating ultraviolet light of a wavelength of 365 nm under the condition of 10 $J/cm^2$ onto the shaped product that was obtained as described above, and definitively curing the shaped product, a cured product is obtained. The cured product that is obtained is used as the object of measurement of hardness.

The hardness of the cured product is measured in accordance with ISO 7619-1: 2010.

<Rupture Elongation of Cured Product>

At the photocurable composition of the second embodiment, the rupture elongation of the cured product obtained by curing the photocurable composition is preferably greater than or equal to 10%.

Due thereto, at the time when external force is applied to the cured product, the occurrence of breakage (formation of fissures, formation of tears, formation of cracks, and the like) can be suppressed.

Further, due to the rupture elongation of the cured product being within the above-described range, the restorability (an improvement in the restoring speed, a suppression of the amount of deformation at the time of being restored, and the like), by which, when, after external force is applied once to the cured product, that external force is cancelled, the shape of the cured product returns to the shape before that external force was applied, can be improved. Further, in a case in which the rupture elongation of the cured product is within the above-described range, and the adhesive force of the cured product is less than or equal to 1.5 N, the above-described restorability can be improved even more. Moreover, in a case in which the rupture elongation of the cured product is within the above-described range, and the adhesive force of the cured product is less than or equal to 1.5 N, the amount of deformation at the time of the above-described restoring can be suppressed better.

From the above-described standpoints, the rupture elongation of the cured product is preferably greater than or equal to 20%, and more preferably greater than or equal to 40%, and even more preferably greater than or equal to 60%.

Note that, in the present disclosure, the rupture elongation of the cured product is measured by the following method.

First, by illuminating visible light onto the photocurable composition by using a 3D printer, the photocurable composition is shaped into the shape of a dumbbell-type test piece conforming to ISO 37-2, and a shaped product (layered width 50 μm) is obtained.

In the aforementioned illuminating of the visible light using the 3D printer, visible light of a wavelength of 405 nm is illuminated onto the respective layers within a range of 5.0 $mJ/cm^2$~10 $mJ/cm^2$ and under the condition of becoming a desired thickness.

By illuminating ultraviolet light of a wavelength of 365 nm under the condition of 10 $J/cm^2$ onto the shaped product that was obtained as described above, and definitively curing the shaped product, a cured product is obtained. The cured product that is obtained is used as the object of measurement of rupture elongation.

The rupture elongation of the cured product that is the object of measurement is measured in accordance with ISO 37: 2017 by using a tensile testing device and under the condition of a pulling speed of 500±50 mm/minute.

Details of preferable ranges, measuring methods and the like of the viscosity of the second embodiment are similar to the details of preferable ranges, measuring methods and the like that are put forth in the (Viscosity) in the above-described first embodiment.

<<Form 2b>>

The photocurable composition relating to Form 2b of the second embodiment contains a (meth)acrylic monomer component and a photopolymerization initiator, and the (meth)acrylic monomer component contains (meth)acrylic monomer (A) having two (meth)acryloyl groups and (meth) acrylic monomer (B) having one (meth)acryloyl group, and the molecular weight per one (meth)acryloyl group in (meth) acrylic monomer (A) is greater than or equal to 300 g/mol, and at least one of (meth)acrylic monomer (A) and (meth) acrylic monomer (B) has an aromatic group, and the shore A hardness of the cured product is less than or equal to 97.

The respective components and the like contained in the photocurable compositions of Form 2a and Form 2b in the second embodiment are described in detail hereinafter.

Details of specific examples, preferable aspects and the like of the (meth)acrylic monomer component of the second embodiments are similar to the details of specific examples, preferable aspects and the like that are put forth in the <(Meth)acrylic monomer component> in the above-described first embodiment.

Specific examples, preferable aspects and the like of (meth)acrylic monomer (A) having two (meth)acryloyl groups of the second embodiment are similar to the specific examples, preferable aspects and the like that are put forth in the ((Meth)acrylic monomer (A) having two (meth) acryloyl groups) in the above-described first embodiment.

Details of preferable ranges, deriving methods and the like of the molecular weight per one (meth)acryloyl group of the second embodiment are similar to the details of preferable ranges, deriving methods and the like that are put forth in the (Molecular weight per one (meth)acryloyl group) in the above-described first embodiment.

Details of specific examples, preferable aspects and the like of (meth)acrylic monomer (B) having one (meth)acryloyl group of the second embodiment are similar to the details of specific examples, preferable aspects and the like that are put forth in the ((Meth)acrylic monomer (B) having one (meth)acryloyl group) in the above-described first embodiment.

In the photocurable composition of the second embodiment, it is preferable that at least one of (meth)acrylic monomer (A) and (meth)acrylic monomer (B) has a ring structure.

Details of specific examples, preferable aspects and the like of the ring structure in the second embodiment are similar to the details of specific examples, preferable aspects and the like of the ring structure that at least one of (meth)acrylic monomer (A) and (meth)acrylic monomer (B) in the first embodiment can have.

In the photocurable composition of the second embodiment, it is preferable that at least one of (meth)acrylic monomer (A) and (meth)acrylic monomer (B) has an aromatic group.

Details of specific examples, preferable aspects and the like of the aromatic group in the second embodiment are similar to the details of specific examples, preferable aspects and the like of the aromatic group that at least one of (meth)acrylic monomer (A) and (meth)acrylic monomer (B) in the first embodiment can have.

In the photocurable composition of the second embodiment, it is preferable that the content of (meth)acrylic monomer (A), with respect to a total content of 1000 parts by mass of (meth)acrylic monomer (A) and (meth)acrylic monomer (B), be 250 parts by mass~800 parts by mass, and more preferably 350 parts by mass~650 parts by mass.

In the photocurable composition of the second embodiment, the total content of (meth)acrylic monomer (A) and (meth)acrylic monomer (B) in the (meth)acrylic monomer component is preferably greater than or equal to 90% by mass, and more preferably greater than or equal to 95% by mass.

The photocurable composition of the second embodiment may contain acrylic rubber particles.

Details of specific examples, preferable aspects and the like of the acrylic rubber particles in the second embodiment are similar to the details of specific examples, preferable aspects and the like of acrylic rubber particles that may be contained in the photocurable composition in the first embodiment.

In (meth)acrylic monomer (A) and (meth)acrylic monomer (B) in the second embodiment, Z in Formula $\alpha$ that is put forth in the above-described first embodiment is preferably within the range shown for the term of Formula $\alpha$ that is put forth in the above-described first embodiment.

In (meth)acrylic monomer (A) and (meth)acrylic monomer (B) in the second embodiment, Z1 in Formula $\beta$ that is put forth in the above-described first embodiment is preferably within the range shown for the term of Formula $\beta$ that is put forth in the above-described first embodiment.

The photocurable composition of the second embodiment preferably satisfies at least one of (a) and (b) that are put forth in the above-described first embodiment section.

Further, details of (a) and (b) such as specific examples, preferable aspects, definitions, contents, and the like of (meth)acrylic monomer (A-1), (meth)acrylic monomer (A-2), (meth)acrylic monomer (B-1) and (meth)acrylic monomer (B-2) are similar to the details of (a) and (b) such as specific examples, preferable aspects, definitions, contents, and the like of (meth)acrylic monomer (A-1), (meth) acrylic monomer (A-2), (meth)acrylic monomer (B-1) and (meth)acrylic monomer (B-2) in the above-described first embodiment.

(Other Additives in the (Meth)Acrylic Monomer Component)

The (meth)acrylic monomer component of the second embodiment may include other additives other than above-described (meth)acrylic monomer (A) and above-described (meth)acrylic monomer (B).

Details of specific examples, preferable aspects and the like of the other additives in the second embodiment are similar to the details of specific examples, preferable aspects and the like of the other additives that are put forth in the section (Other Additives in the (meth)acrylic monomer Component) in the above-described first embodiment.

(Photopolymerization Initiator)

The photocurable composition of the second embodiment contains a photopolymerization initiator.

Details of specific examples, preferable aspects and the like of the photopolymerization initiator in the second embodiment are similar to the details of specific examples, preferable aspects and the like of the photopolymerization initiator in the above-described first embodiment.

<Other Components>

The photocurable composition of the second embodiment may include, as needed, one or more types of other components that are other than (meth)acrylic monomer (A), (meth)acrylic monomer (B), and a photopolymerization initiator.

Details of specific examples, preferable aspects and the like of the other components in the second embodiment are similar to the details of specific examples, preferable aspects and the like of the other components in the above-described first embodiment.

The method of preparing the photocurable composition of the second embodiment is not particularly limited, and an example thereof is a method of mixing-together (meth) acrylic monomer (A) and (meth)acrylic monomer (B), and a photopolymerization initiator (and other components as needed).

Details are as put forth in the above-described first embodiment section.

<<Cured Product>>

Details of specific examples, preferable aspects and the like of the cured product of the second embodiment are similar to the details of specific examples, preferable aspects and the like of the cured product that are put forth in the <<Cured Product>> of the above-described first embodiment.

<Stereolithography>

The photocurable composition of the second embodiment is preferably used for stereolithography.

Details of preferable aspects, definitions and the like of the photocurable composition of the second embodiment being used for stereolithography are similar to the details of preferable aspects, definitions and the like that are put forth in the <Stereolithography> of the above-described first embodiment.

<3D Printer>

Details of specific examples, preferable aspects and the like of the 3D printer in the second embodiment are similar to the details of specific examples, preferable aspects and the like that are put forth in the <3D Printer> of the above-described first embodiment.

<<Dental Product>>

The photocurable composition of the second embodiment is suitably used in fabricating dental products by stereolithography.

Further, the photocurable composition of the second embodiment is suitably used in fabricating mouthpieces, gingiva masks and lining materials by stereolithography, and is more suitably used in fabricating mouthpieces and gingiva masks.

<Method of Manufacturing Mouthguard and Mouthguard>

In a case in which the dental product of the second embodiment is a mouthguard, the mouthguard is preferably manufactured by stereolithography.

Details of specific methods of manufacturing, preferable aspects and the like are similar to the details of methods of manufacturing, preferable aspects and the like that are put forth in the <Method of Manufacturing Mouthguard and Mouthguard> of the above-described first embodiment.

EXAMPLES

An embodiment of the present disclosure is described more specifically by way of Examples, but the present disclosure is not limited to these Examples.

Examples A

Examples A are Examples for more specifically describing the first embodiment of the present disclosure.

<Preparation of Photocurable Composition>

Examples 1A~43A, Comparative Examples 2A 3A

The respective components listed in following Table 1~Table 3 were mixed-together, and photocurable compositions were obtained. The viscosities of the respective photocurable compositions are shown in Table 1.

Note that the aforementioned viscosity was measured by a method similar to the above-described method.

Comparative Example 1A

A gingiva mask (manufactured by NextDent B.V.) was used as the photocurable composition.

<Evaluation>

The following measurements and evaluations were carried out on the test pieces that were obtained. The results are shown in Table 1~Table 3.

(Rupture Elongation)

The obtained photocurable composition was shaped into the shape of a dumbbell-type test piece conforming to ISO 37-2 by using a 3D printer (Kulzer LLC, CaraPrint 4.0) under the conditions of the wavelength of the visible light being 405 nm and the illuminance of the visible light being 8.0 mJ/cm$^2$, and a shaped product (layered width 50 μm) was obtained. By illuminating ultraviolet light of a wavelength of 365 nm under the condition of 10 J/cm$^2$ onto the shaped product that was obtained, and definitively curing the shaped product, a photoshaped product (i.e., a cured product) was obtained.

The rupture elongation of the photoshaped product that was obtained (hereinafter called "test piece") was measured in accordance with ISO 37: 2017. These measurements were carried out by using a tensile testing device (manufactured by Shimadzu Corporation) and under the condition of a pulling speed of 500±50 mm/minute.

(Shore A Hardness)

The obtained photocurable composition was shaped to length 25 mm×width 25 mm×thickness 6 mm, by using a 3D printer (Kulzer LLC, CaraPrint 4.0) and under the conditions of the wavelength of the visible light being 405 nm and the illuminance of the visible light being 8.0 mJ/cm$^2$, and a shaped product (layered width 50 μm) was obtained. By illuminating ultraviolet light of a wavelength of 365 nm under the condition of 10 J/cm$^2$ onto the shaped product that was obtained, and definitively curing the shaped product, a photoshaped product (i.e., a cured product) was obtained.

The shore A hardness of the photoshaped product that was obtained (hereinafter called "test piece") was measured in accordance with ISO 7619-1: 2010. In measuring the hardness, a durometer-type hardness tester (manufactured by Mitutoyo Corporation) was used, and the numerical value after 15 seconds after needle insertion was used as the value of the shore A hardness.

(Adhesive Force)

The obtained photocurable composition was shaped to length 20 mm×width 20 mm×thickness 2 mm, by using a 3D printer (Kulzer LLC, CaraPrint 4.0) and under the conditions of the wavelength of the visible light being 405 nm and the illuminance of the visible light being 8.0 mJ/cm$^2$, and a shaped product (layered width 50 μm) was obtained. By illuminating ultraviolet light of a wavelength of 365 nm under the condition of 10 J/cm$^2$ onto the shaped product that was obtained, and definitively curing the shaped product, a photoshaped product was obtained.

The photoshaped product that was obtained (hereinafter called "test piece") was affixed to a sample stand such that there was no slack therein. Next, a probe, which was made of aluminum and whose contact surface area was length 10 mm×width 10 mm, and a 20 mm long×20 mm wide surface of the test piece, were made to contact one another, and were left for 1.0±0.1 seconds at a contact load of 0.98±0.01 N/cm$^2$.

Thereafter, by using a tensile testing device (manufactured by Shimadzu Corporation), the aforementioned probe was pulled-off from the contact surface in the vertical direction at a speed of 5±0.5 mm per second. Then, the maximum load needed at the time of pulling the aforementioned probe off from the contact surface was determined, and was used as the adhesive force (unit: N) of the cured product.

(Shock Absorbing Ability)

The obtained photocurable composition was shaped to length 20 mm×width 20 mm×thickness 3 mm, by using a 3D printer (Kulzer LLC, CaraPrint 4.0) and under the conditions of the wavelength of the visible light being 405 nm and the illuminance of the visible light being 8.0 mJ/cm$^2$, and a shaped product (layered width 50 μm) was obtained.

By illuminating ultraviolet light of a wavelength of 365 nm under the condition of 10 J/cm$^2$ onto the shaped product that was obtained, and definitively curing the shaped product, a photoshaped product was obtained.

The shock absorbing ability (A (%)) of the photoshaped product that was obtained (hereinafter called "test piece") was measured by the above-described method.

The maximum load was measured by using a compact load cell for compression/tension dual use (LMU-200N, manufactured by Imada Co., Ltd.) that was connected to a load output device (ZT Digital Force Gauge, manufactured by Imada Co., Ltd.).

The measurement of the maximum load was carried out under the condition of a temperature of 23° C. on the test piece within the 30 seconds after the test piece had been left for 15 minutes at 37° C.

The free dropping of the iron ball was carried out in the atmosphere.

(Shape Restoring Test)

The obtained photocurable composition was shaped to length 8 mm×width 39 mm×thickness 4 mm, by using a 3D printer (Kulzer LLC, CaraPrint 4.0) and under the conditions of the wavelength of the visible light being 405 nm and the illuminance of the visible light being 8.0 mJ/cm$^2$, and a shaped product (layered width 50 μm) was obtained.

By illuminating ultraviolet light of a wavelength of 365 nm under the condition of 10 J/cm$^2$ onto the shaped product that was obtained, and definitively curing the shaped product, a photoshaped product was obtained.

Stress was applied to the photoshaped product that was obtained (hereinafter called "test piece"), and the test piece was curved such that the both ends in the long axis direction (lateral axis direction) of the test piece contacted one another, and was maintained for 10 seconds. Thereafter, the stress was released, and the change in the shape of the test piece was observed and was evaluated in accordance with the following standards.

S: After the stress was released, the test piece returned to its original shape in greater than or equal to 0 seconds and less than 1 second.

A: After the stress was released, the test piece returned to its original shape in greater than or equal to 1 second and less than 3 seconds.

B: After the stress was released, the test piece returned to its original shape in greater than or equal to 3 seconds and less than 10 seconds.

C: After the stress was released, the test piece had not returned to its original shape at the point in time of 10 seconds, but breakage and fissures did not occur.

D: During the time when the stress was being applied for the 10 seconds, fissures arose in the test piece, and the test piece broke in the time period up until the time when the stress was released.

TABLE 1

| | component | name | Mw | molecular weight (g/mol) per (meth)-acrylic functional group | number of aromatic rings in monomer | CoEx1A | CoEx2A | CoEx3A | Ex1A | Ex2A | Ex3A |
|---|---|---|---|---|---|---|---|---|---|---|---|
| composition | (meth)-acrylic monomer (A) | UA-160TM | 1600 | 800 | 0 | — | | | 30 | 40 | 40 |
| | | UA-122P | 1100 | 550 | 0 | — | | | | | |
| | | UN-6305 | 27000 | 13500 | 0 | — | | | | | |
| | | UN-2700 | 2000 | 1000 | 0 | — | | | | | |
| | | UN-2600 | 2500 | 1250 | 0 | — | | | | | |
| | | UN-352 | 3000 | 1500 | 0 | — | | | | | |
| | | UN-333 | 3000 | 1500 | 0 | — | | | | | |
| | | SUA-01 | 1680 | 840 | 0 | — | | | | | |
| | | SUA-02 | 1680 | 840 | 0 | — | | | | | |
| | | SUA-03 | 1734 | 867 | 0 | — | | | | | |
| | | SUA-04 | 1734 | 867 | 0 | — | | | | | |
| | | SUA-05 | 1734 | 867 | 0 | — | | | | | |
| | | AH-600 | 612.68 | 306.34 | 2 | — | | | | | |
| | | MMD-352 | 632.67 | 316.335 | 3 | — | | | | | |
| | | Ebecryl8402 | 1000 | 500 | 0 | — | | | | | |
| | | Ebecryl230 | 5000 | 2500 | 0 | — | | | | | |
| composition | other (meth)-acrylic monomers | 4EG | 330.38 | 165.19 | 0 | — | 40 | 40 | | | |
| | (meth)-acrylic monomer (B) | PO-A | 192.21 | 192.21 | 1 | — | | | | | |
| | | P2H-A | 236.27 | 236.27 | 1 | — | 60 | | 70 | 60 | 60 |
| | | POBA | 254.29 | 254.29 | 2 | — | | | | | |
| | | M-600A | 222.24 | 222.24 | 1 | — | | | | | |
| | | M110 | 319.2 | 319.2 | 2 | — | | | | | |
| | | M111 | 318.46 | 318.46 | 1 | — | | | | | |
| | | M113 | 450.62 | 450.62 | 1 | — | | | | | |
| | | HRD01 | 268.31 | 268.31 | 2 | — | | | | | |
| | | BZ | 176.22 | 176.22 | 1 | — | | | | | |
| | | PO | 206.24 | 206.24 | 1 | — | | | | | |
| | | L-A | 240.39 | 240.39 | 0 | — | | | | | |
| | | THF-A | 156.18 | 156.18 | 0 | — | | 60 | | | |
| composition | photo-polymerization initiator | OmniradTPO | 348.38 | — | — | — | 2 | 2 | 2 | 2 | |
| | | Omnirad819 | 418.47 | — | — | — | | | | | 2 |
| total | | | | | — | — | 102 | 102 | 102 | 102 | 102 |
| viscosity (mPa · s) of composition | | | | | — | 1450 | 135 | 92 | 357 | 470 | 481 |
| shore A hardness | | | | | — | 65 | 96 | 85 | 52 | 55 | 58 |
| rupture elongation (%) | | | | | — | 30 | 3 | 7 | 66 | 51 | 47 |
| adhesive force (N) | | | | | — | 1.72 | 0.11 | 0.84 | 0.64 | 0.52 | 0.27 |
| shock absorbing ability (%) | | | | | — | 27 | 7 | 6 | 31 | 37 | 40 |
| shape restoring test | | | | | — | D | D | D | B | B | A |
| structural proportion (%) of (meth)acrylic monomer (A) | | | | | — | — | 40 | 40 | 30 | 40 | 40 |
| (meth)acryloyl group concentration (mol/g) of (meth)acrylic monomer (A) | | | | | — | — | 0.0061 | 0.006 | 0.001 | 0.001 | 0.001 |
| molecular weight (g/mol) per (meth)acryloyl group of (meth)acrylic monomer (A) | | | | | — | — | 165.19 | 165.2 | 800 | 800 | 800 |
| aromatic ring concentration (mol/g) in total monomers | | | | | — | — | 0.0025 | 0 | 0.003 | 0.002 | 0.002 |
| X1 [molecular weight of (meth)acrylic monomer (A) per (meth)acryloyl group]/Y [aromatic ring concentration (mol/g) in (meth)acrylic monomer component] ($\times 10^4$ $g^2/mol^2$) | | | | | — | — | 7 | ∞ | 28 | 32 | 32 |
| aromatic ring concentration (mol/g) in (meth)acrylic monomer (A) | | | | | | | 0 | 0 | 0 | 0 | 0 |

TABLE 1-continued

| | component | name | Mw | molecular weight (g/mol) per (meth)acrylic functional group | Ex4A | Ex5A | Ex6A | Ex7A | Ex8A | Ex9A | Ex10A |
|---|---|---|---|---|---|---|---|---|---|---|---|
| composition | (meth)acrylic monomer (A) | UA-160TM | 1600 | 800 | 50 | 60 | 70 | 40 | 40 | 40 | 30 |
| | | UA-122P | 1100 | 550 | | | | | | | |
| | | UN-6305 | 27000 | 13500 | | | | | | | |
| | | UN-2700 | 2000 | 1000 | | | | | | | |
| | | UN-2600 | 2500 | 1250 | | | | | | | |
| | | UN-352 | 3000 | 1500 | | | | | | | |
| | | UN-333 | 3000 | 1500 | | | | | | | |
| | | SUA-01 | 1680 | 840 | | | | | | | |
| | | SUA-02 | 1680 | 840 | | | | | | | |
| | | SUA-03 | 1734 | 867 | | | | | | | |
| | | SUA-04 | 1734 | 867 | | | | | | | |
| | | SUA-05 | 1734 | 867 | | | | | | | |
| | | AH-600 | 612.68 | 306.34 | | | | | | | |
| | | MMD-352 | 632.67 | 316.335 | | | | | | | |
| | | Ebecryl8402 | 1000 | 500 | | | | | | | |
| | | Ebecryl230 | 5000 | 2500 | | | | | | | |
| composition | other (meth)acrylic monomers | 4EG | 330.38 | 165.19 | | | | | | | |
| | (meth)acrylic monomer (B) | PO-A | 192.21 | 192.21 | | | | | | | |
| | | P2H-A | 236.27 | 236.27 | 50 | | | 30 | | | |
| | | POBA | 254.29 | 254.29 | | 40 | | 30 | 60 | | 70 |
| | | M-600A | 222.24 | 222.24 | | | | | | | |
| | | M110 | 319.2 | 319.2 | | | | | | 30 | |
| | | M111 | 318.46 | 318.46 | | | | | | | |
| | | M113 | 450.62 | 450.62 | | | | | | | |
| | | HRD01 | 268.31 | 268.31 | | | 30 | | | | |
| | | BZ | 176.22 | 176.22 | | | | | | | |
| | | PO | 206.24 | 206.24 | | | | | | | |
| | | L-A | 240.39 | 240.39 | | | | | | 30 | |
| | | THF-A | 156.18 | 156.18 | | | | | | | |
| composition | photopolymerization initiator | OmniradTPO | 348.38 | — | 2 | 2 | 2 | 2 | 2 | 2 | 2 |
| | | Omnirad819 | 418.47 | — | | | | | | | |
| total | | | | | 102 | 102 | 102 | 102 | 102 | 102 | 102 |
| viscosity (mPa · s) of composition | | | | | 1228 | 2350 | 3560 | 425 | 468 | 311 | 326 |
| shore A hardness | | | | | 58 | 63 | 65 | 60 | 83 | 54 | 76 |
| rupture elongation (%) | | | | | 53 | 55 | 48 | 65 | 88 | 31 | 103 |
| adhesive force (N) | | | | | 0.32 | 0.08 | 0.07 | 0.14 | 0.44 | 0.55 | 0.77 |
| shock absorbing ability (%) | | | | | 39 | 43 | 36 | 41 | 42 | 35 | 40 |
| shape restoring test | | | | | B | A | B | S | A | B | A |
| structural proportion (%) of (meth)acrylic monomer (A) | | | | | 50 | 60 | 70 | 40 | 40 | 40 | 30 |
| (meth)acryloyl group concentration (mol/g) of (meth)acrylic monomer (A) | | | | | 0.001 | 0.001 | 0.001 | 0.001 | 0.001 | 0.001 | 0.001 |
| molecular weight (g/mol) per (meth)acryloyl group of (meth)acrylic monomer (A) | | | | | 800 | 800 | 800 | 800 | 800 | 800 | 800 |
| aromatic ring concentration (mol/g) in total monomers | | | | | 0.002 | 0.003 | 0.002 | 0.004 | 0.005 | 0.002 | 0.005 |
| X1 [molecular weight of (meth)acrylic monomer (A) per (meth)acryloyl group]/Y [aromatic ring concentration (mol/g) in (meth)acrylic monomer component] ($\times10^4$ $g^2/mol^2$) | | | | | 39 | 26 | 36 | 22 | 17 | 43 | 15 |
| aromatic ring concentration (mol/g) in (meth)acrylic monomer (A) | | | | | 0 | 0 | 0 | 0 | 0 | 0 | 0 |

TABLE 2

| | component | name | Mw | molecular weight (g/mol) per (meth)-acrylic functional group | number of aromatic rings in monomer | Ex11A | Ex12A | Ex13A | Ex14A | Ex15A | Ex16A |
|---|---|---|---|---|---|---|---|---|---|---|---|
| composition | (meth)-acrylic monomer (A) | UA-160TM | 1600 | 800 | 0 | 40 | 40 | 40 | 40 | 40 | 40 |
| | | UA-122P | 1100 | 550 | 0 | | | | | | |
| | | UN-6305 | 27000 | 13500 | 0 | | | | | | |
| | | UN-2700 | 2000 | 1000 | 0 | | | | | | |
| | | UN-2600 | 2500 | 1250 | 0 | | | | | | |
| | | UN-352 | 3000 | 1500 | 0 | | | | | | |
| | | UN-333 | 3000 | 1500 | 0 | | | | | | |
| | | SUA-01 | 1680 | 840 | 0 | | | | | | |
| | | SUA-02 | 1680 | 840 | 0 | | | | | | |
| | | SUA-03 | 1734 | 867 | 0 | | | | | | |
| | | SUA-04 | 1734 | 867 | 0 | | | | | | |
| | | SUA-05 | 1734 | 867 | 0 | | | | | | |
| | | AH-600 | 612.7 | 306.34 | 2 | | | | | | |
| | | MMD-352 | 632.7 | 316.335 | 3 | | | | | | |
| | | Ebecryl8402 | 1000 | 500 | 0 | | | | | | |
| | | Ebecryl230 | 5000 | 2500 | 0 | | | | | | |
| composition | other (meth)-acrylic monomers | 4EG | 330.4 | 165.19 | 0 | | | | | | |
| | (meth)-acrylic monomer (B) | PO-A | 192.2 | 192.21 | 1 | | | | | | |
| | | P2H-A | 236.3 | 236.27 | 1 | 30 | 30 | 30 | | 30 | 30 |
| | | POBA | 254.3 | 254.29 | 2 | | | | 30 | | |
| | | M-600A | 222.2 | 222.24 | 1 | 30 | | | | | |
| | | M110 | 319.2 | 319.2 | 2 | | 30 | | | | |
| | | M111 | 318.5 | 318.46 | 1 | | | 30 | | | |
| | | M113 | 450.6 | 450.62 | 1 | | | | 30 | | |
| | | HRD01 | 268.3 | 268.31 | 2 | | | | | 30 | |
| | | BZ | 176.2 | 176.22 | 1 | | | | | | 30 |
| | | PO | 206.2 | 206.24 | 1 | | | | | | |
| | | L-A | 240.4 | 240.39 | 0 | | | | | | |
| | | THF-A | 156.2 | 156.18 | 0 | | | | | | |
| composition | photo-polymerization initiator | OmniradTPO | 348.4 | — | — | 2 | 2 | 2 | 2 | 2 | 2 |
| | | Omnirad819 | 418.5 | — | — | | | | | | |
| total | | | | | — | 102 | 102 | 102 | 102 | 102 | 102 |
| viscosity (mPa · s) of composition | | | | | — | 721 | 632 | 354 | 562 | 670 | 467 |
| shore A hardness | | | | | — | 53 | 62 | 64 | 76 | 65 | 89 |
| rupture elongation (%) | | | | | — | 75 | 85 | 51 | 34 | 75 | 37 |
| adhesive force (N) | | | | | — | 0.45 | 0.62 | 0.39 | 0.32 | 0.21 | 0.15 |
| shock absorbing ability (%) | | | | | — | 38 | 41 | 43 | 40 | 47 | 26 |
| shape restoring test | | | | | — | B | S | A | S | S | B |
| structural proportion (%) of (meth)acrylic monomer (A) | | | | | — | 40 | 40 | 40 | 40 | 40 | 40 |
| (meth)acryloyl group concentration (mol/g) of (meth)acrylic monomer (A) | | | | | — | 0.001 | 0.001 | 0.001 | 0.001 | 0.001 | 0.001 |
| molecular weight (g/mol) per (meth)acryloyl group of (meth)acrylic monomer (A) | | | | | — | 800 | 800 | 800 | 800 | 800 | 800 |
| aromatic ring concentration (mol/g) in total monomers | | | | | — | 0.003 | 0.003 | 0.002 | 0.003 | 0.003 | 0.003 |
| X1 [molecular weight of (meth)acrylic monomer (A) per (meth)acryloyl group]/Y [aromatic ring concentration (mol/g) in (meth)acrylic monomer component] ($\times 10^4$ $g^2/mol^2$) | | | | | — | 31 | 26 | 37 | 27 | 23 | 27 |
| aromatic ring concentration (mol/g) in (meth)acrylic monomer (A) | | | | | — | 0 | 0 | 0 | 0 | 0 | 0 |

TABLE 2-continued

| | component | name | Mw | molecular weight (g/mol) per (meth)-acrylic functional group | Ex17A | Ex18A | Ex19A | Ex20A | Ex21A |
|---|---|---|---|---|---|---|---|---|---|
| composition | (meth)-acrylic monomer (A) | UA-160TM | 1600 | 800 | 40 | 40 | | | |
| | | UA-122P | 1100 | 550 | | | 40 | | |
| | | UN-6305 | 27000 | 13500 | | | | 40 | 40 |
| | | UN-2700 | 2000 | 1000 | | | | | |
| | | UN-2600 | 2500 | 1250 | | | | | |
| | | UN-352 | 3000 | 1500 | | | | | |
| | | UN-333 | 3000 | 1500 | | | | | |
| | | SUA-01 | 1680 | 840 | | | | | |
| | | SUA-02 | 1680 | 840 | | | | | |
| | | SUA-03 | 1734 | 867 | | | | | |
| | | SUA-04 | 1734 | 867 | | | | | |
| | | SUA-05 | 1734 | 867 | | | | | |
| | | AH-600 | 612.7 | 306.34 | | | | | |
| | | MMD-352 | 632.7 | 316.335 | | | | | |
| | | Ebecryl8402 | 1000 | 500 | | | | | |
| | | Ebecryl230 | 5000 | 2500 | | | | | |
| composition | other (meth)-acrylic monomers | 4EG | 330.4 | 165.19 | | | | | |
| | (meth)-acrylic monomer (B) | PO-A | 192.2 | 192.21 | | 30 | | | 60 |
| | | P2H-A | 236.3 | 236.27 | 30 | | 60 | | |
| | | POBA | 254.3 | 254.29 | | | | | |
| | | M-600A | 222.2 | 222.24 | | | | | |
| | | M110 | 319.2 | 319.2 | | | | | |
| | | M111 | 318.5 | 318.46 | | | | | |
| | | M113 | 450.6 | 450.62 | | | | | |
| | | HRD01 | 268.3 | 268.31 | | 30 | | 60 | |
| | | BZ | 176.2 | 176.22 | | | | | |
| | | PO | 206.2 | 206.24 | 30 | | | | |
| | | L-A | 240.4 | 240.39 | | | | | |
| | | THF-A | 156.2 | 156.18 | | | | | |
| composition | photo-polymerization initiator | OmniradTPO | 348.4 | — | 2 | 2 | 2 | 2 | 2 |
| | | Omnirad819 | 418.5 | — | | | | | |
| total | | | | | 102 | 102 | 102 | 102 | 102 |
| viscosity (mPa · s) of composition | | | | | 696 | 571 | 241 | 2890 | 2460 |
| shore A hardness | | | | | 87 | 73 | 76 | 57 | 53 |
| rupture elongation (%) | | | | | 35 | 51 | 44 | 82 | 69 |
| adhesive force (N) | | | | | 0.2 | 0.11 | 0.14 | 0.75 | 1.43 |
| shock absorbing ability (%) | | | | | 27 | 46 | 36 | 59 | 49 |
| shape restoring test | | | | | B | S | B | A | C |
| structural proportion (%) of (meth)acrylic monomer (A) | | | | | 40 | 40 | 40 | 40 | 40 |
| (meth)acryloyl group concentration (mol/g) of (meth)acrylic monomer (A) | | | | | 0.001 | 0.001 | 0.002 | 0.000074 | 0.000074 |
| molecular weight (g/mol) per (meth)acryloyl group of (meth)acrylic monomer (A) | | | | | 800 | 800 | 550 | 13500 | 13500 |
| aromatic ring concentration (mol/g) in total monomers | | | | | 0.003 | 0.004 | 0.002 | 0.004385 | 0.00306038 |
| X1 [molecular weight of (meth)acrylic monomer (A) per (meth)acryloyl group]/Y [aromatic ring concentration (mol/g) in (meth)acrylic monomer component] ($\times 10^4$ $g^2/mol^2$) | | | | | 30 | 21 | 22 | 308 | 441 |
| aromatic ring concentration (mol/g) in (meth)acrylic monomer (A) | | | | | 0 | 0 | 0 | 0 | 0 |

TABLE 3

| | component | name | Mw | molecular weight (g/mol) per (meth)-acrylic functional group | number of aromatic rings in monomer | Ex 22 A | Ex 23 A | Ex 24 A | Ex 25 A | Ex 26 A | Ex 27 A |
|---|---|---|---|---|---|---|---|---|---|---|---|
| composition | (meth)-acrylic monomer (A) | UA-160TM | 1600 | 800 | 0 | | | | | | |
| | | UA-122P | 1100 | 550 | 0 | | | | | | |
| | | UN-6305 | 27000 | 13500 | 0 | | | | | | |
| | | UN-2700 | 2000 | 1000 | 0 | 40 | | | | | |
| | | UN-2600 | 2500 | 1250 | 0 | | 40 | | | | |
| | | UN-352 | 3000 | 1500 | 0 | | | 40 | | | |
| | | UN-333 | 3000 | 1500 | 0 | | | | 40 | | |
| | | SUA-01 | 1680 | 840 | 0 | | | | | 40 | |
| | | SUA-02 | 1680 | 840 | 0 | | | | | | 40 |
| | | SUA-03 | 1734 | 867 | 0 | | | | | | |
| | | SUA-04 | 1734 | 867 | 0 | | | | | | |
| | | SUA-05 | 1734 | 867 | 0 | | | | | | |
| | | AH-600 | 612.68 | 306.34 | 2 | | | | | | |
| | | MMD-352 | 632.67 | 316.335 | 3 | | | | | | |
| | | Ebecryl8402 | 1000 | 500 | 0 | | | | | | |
| | | Ebecryl230 | 5000 | 2500 | 0 | | | | | | |
| composition | other (meth)-acrylic monomers | 4EG | 330.38 | 165.19 | 0 | | | | | | |
| | (meth)-acrylic monomer (B) | PO-A | 192.21 | 192.21 | 1 | | | | | | |
| | | P2H-A | 236.27 | 236.27 | 1 | 60 | 60 | 60 | 60 | 60 | 60 |
| | | POBA | 254.29 | 254.29 | 2 | | | | | | |
| | | M-600A | 222.24 | 222.24 | 1 | | | | | | |
| | | M110 | 319.2 | 319.2 | 2 | | | | | | |
| | | M111 | 318.46 | 318.46 | 1 | | | | | | |
| | | M113 | 450.62 | 450.62 | 1 | | | | | | |
| | | HRD01 | 268.31 | 268.31 | 2 | | | | | | |
| | | BZ | 176.22 | 176.22 | 1 | | | | | | |
| | | PO | 206.24 | 206.24 | 1 | | | | | | |
| | | L-A | 240.39 | 240.39 | 0 | | | | | | |
| | | THF-A | 156.18 | 156.18 | 0 | | | | | | |
| composition | photo-polymerization initiator | OmniradTPO | 348.38 | — | — | 2 | 2 | 2 | 2 | 2 | 2 |
| | | Omnirad819 | 418.47 | — | — | | | | | | |
| total | | | | | — | 102 | 102 | 102 | 102 | 102 | 102 |
| viscosity (mPa · s) of composition | | | | | — | 722 | 802 | 886 | 1083 | 515 | 485 |
| shore A hardness | | | | | — | 78 | 65 | 89 | 76 | 58 | 61 |
| rupture elongation (%) | | | | | — | 47.62 | 62 | 42 | 34 | 49 | 41 |
| adhesive force (N) | | | | | — | 0.64 | 0.72 | 0.54 | 0.51 | 0.75 | 0.21 |
| shock absorbing ability (%) | | | | | — | 47 | 48 | 52 | 23 | 41 | 41 |
| shape restoring test | | | | | — | A | A | A | C | A | A |
| structural proportion (%) of (meth)acrylic monomer (A) | | | | | — | 40 | 40 | 40 | 40 | 40 | 40 |
| (meth)acryloyl group concentration (mol/g) of (meth)acrylic monomer (A) | | | | | — | 0.001 | 8E−04 | 7E−04 | 7E−04 | 0.001 | 0.001 |
| molecular weight (g/mol) per (meth)acryloyl group of (meth)acrylic monomer (A) | | | | | — | 1000 | 1250 | 1500 | 1500 | 840 | 840 |
| aromatic ring concentration (mol/g) in total monomers | | | | | — | 0.002 | 0.002 | 0.002 | 0.002 | 0.002 | 0.002 |
| X1 [molecular weight of (meth)acrylic monomer (A) per (meth)acryloyl group]/Y [aromatic ring concentration (mol/g) in (meth)acrylic monomer component] (×$10^4$ $g^2/mol^2$) | | | | | — | 40 | 50 | 60 | 60 | 34 | 34 |
| aromatic ring concentration (mol/g) in (meth)acrylic monomer (A) | | | | | — | 0 | 0 | 0 | 0 | 0 | 0 |

TABLE 3-continued

| | component | name | Mw | molecular weight (g/mol) per (meth)-acrylic functional group | Ex 28 A | Ex 29 A | Ex 30 A | Ex 31 A | Ex 32 A | Ex 33 A |
|---|---|---|---|---|---|---|---|---|---|---|
| composition | (meth)-acrylic monomer (A) | UA-160TM | 1600 | 800 | | | | | | |
| | | UA-122P | 1100 | 550 | | | | | | |
| | | UN-6305 | 27000 | 13500 | | | | | | |
| | | UN-2700 | 2000 | 1000 | | | | | | |
| | | UN-2600 | 2500 | 1250 | | | | | | |
| | | UN-352 | 3000 | 1500 | | | | | | |
| | | UN-333 | 3000 | 1500 | | | | | | |
| | | SUA-01 | 1680 | 840 | | | | | | |
| | | SUA-02 | 1680 | 840 | | | | | | |
| | | SUA-03 | 1734 | 867 | 40 | | | | | |
| | | SUA-04 | 1734 | 867 | | 40 | | | | |
| | | SUA-05 | 1734 | 867 | | | 40 | | | |
| | | AH-600 | 612.68 | 306.34 | | | | 30 | | |
| | | MMD-352 | 632.67 | 316.335 | | | | | 30 | 30 |
| | | Ebecryl8402 | 1000 | 500 | | | | | | |
| | | Ebecryl230 | 5000 | 2500 | | | | | | |
| composition | other (meth)-acrylic monomers | 4EG | 330.38 | 165.19 | | | | | | |
| | (meth)-acrylic monomer (B) | PO-A | 192.21 | 192.21 | | | | | | |
| | | P2H-A | 236.27 | 236.27 | 60 | 60 | 60 | | | |
| | | POBA | 254.29 | 254.29 | | | | | | |
| | | M-600A | 222.24 | 222.24 | | | | 70 | 70 | |
| | | M110 | 319.2 | 319.2 | | | | | | 70 |
| | | M111 | 318.46 | 318.46 | | | | | | |
| | | M113 | 450.62 | 450.62 | | | | | | |
| | | HRD01 | 268.31 | 268.31 | | | | | | |
| | | BZ | 176.22 | 176.22 | | | | | | |
| | | PO | 206.24 | 206.24 | | | | | | |
| | | L-A | 240.39 | 240.39 | | | | | | |
| | | THF-A | 156.18 | 156.18 | | | | | | |
| composition | photopolymerization initiator | OmniradTPO | 348.38 | — | 2 | 2 | 2 | 2 | 2 | 2 |
| | | Omnirad819 | 418.47 | — | | | | | | |
| total | | | | | 102 | 102 | 102 | 102 | 102 | 102 |
| viscosity (mPa · s) of composition | | | | | 620 | 598 | 568 | 854 | 1248 | 1336 |
| shore A hardness | | | | | 55 | 63 | 50 | 93 | 95 | 93 |
| rupture elongation (%) | | | | | 52 | 44 | 59 | 24 | 25 | 30 |
| adhesive force (N) | | | | | 0.61 | 0.81 | 0.31 | 0.19 | 0.13 | 0.09 |
| shock absorbing ability (%) | | | | | 46 | 44 | 42 | 32 | 36 | 32 |
| shape restoring test | | | | | A | A | A | B | B | B |
| structural proportion (%) of (meth)acrylic monomer (A) | | | | | 40 | 40 | 40 | 30 | 30 | 30 |
| (meth)acryloyl group concentration (mol/g) of (meth)acrylic monomer (A) | | | | | 0.001 | 0.001 | 0.001 | 0.003 | 0.003 | 0.003 |
| molecular weight (g/mol) per (meth)acryloyl group of (meth)acrylic monomer (A) | | | | | 867 | 867 | 867 | 306.3 | 316.3 | 316.3 |
| aromatic ring concentration (mol/g) in total monomers | | | | | 0.002 | 0.002 | 0.002 | 0.004 | 0.004 | 0.006 |
| X1 [molecular weight of (meth)acrylic monomer (A) per (meth)acryloyl group]/Y [aromatic ring concentration (mol/g) in (meth)acrylic monomer component] (×$10^4$ $g^2/mol^2$) | | | | | 35 | 35 | 35 | 8 | 7 | 6 |
| aromatic ring concentration (mol/g) in (meth)acrylic monomer (A) | | | | | 0 | 0 | 0 | 1E−03 | 0.001 | 0.001 |

TABLE 3-continued

| | component | name | Mw | molecular weight (g/mol) per (meth)-acrylic functional group | Ex 34 A | Ex 35 A | Ex 36 A | Ex 37 A | Ex 38 A |
|---|---|---|---|---|---|---|---|---|---|
| composition | (meth)-acrylic monomer (A) | UA-160TM | 1600 | 800 | 40 | | | 40 | 40 |
| | | UA-122P | 1100 | 550 | | | | | |
| | | UN-6305 | 27000 | 13500 | | | | | |
| | | UN-2700 | 2000 | 1000 | | | | | |
| | | UN-2600 | 2500 | 1250 | | | | | |
| | | UN-352 | 3000 | 1500 | | | | | |
| | | UN-333 | 3000 | 1500 | | | | | |
| | | SUA-01 | 1680 | 840 | | | | | |
| | | SUA-02 | 1680 | 840 | | | | | |
| | | SUA-03 | 1734 | 867 | | | | | |
| | | SUA-04 | 1734 | 867 | | | | | |
| | | SUA-05 | 1734 | 867 | | | | | |
| | | AH-600 | 612.68 | 306.34 | 20 | | | | 20 |
| | | MMD-352 | 632.67 | 316.335 | | | | | |
| | | Ebecryl8402 | 1000 | 500 | | 40 | | | |
| | | Ebecryl230 | 5000 | 2500 | | | 40 | 20 | |
| composition | other (meth)-acrylic monomers | 4EG | 330.38 | 165.19 | | | | | |
| | (meth)-acrylic monomer (B) | PO-A | 192.21 | 192.21 | | | | | |
| | | P2H-A | 236.27 | 236.27 | | 60 | 60 | | 20 |
| | | POBA | 254.29 | 254.29 | | | | | |
| | | M-600A | 222.24 | 222.24 | | | | | |
| | | M110 | 319.2 | 319.2 | | | | 40 | |
| | | M111 | 318.46 | 318.46 | | | | | |
| | | M113 | 450.62 | 450.62 | | | | | |
| | | HRD01 | 268.31 | 268.31 | 40 | | | | 20 |
| | | BZ | 176.22 | 176.22 | | | | | |
| | | PO | 206.24 | 206.24 | | | | | |
| | | L-A | 240.39 | 240.39 | | | | | |
| | | THF-A | 156.18 | 156.18 | | | | | |
| composition | photo-polymer-ization initiator | OmniradTPO | 348.38 | — | 2 | 2 | 2 | 2 | 2 |
| | | Omnirad819 | 418.47 | — | | | | | |
| total | | | | | 102 | 102 | 102 | 102 | 102 |
| viscosity (mPa · s) of composition | | | | | 1920 | 349 | 862 | 1543 | 1354 |
| shore A hardness | | | | | 93 | 91 | 71 | 91 | 94 |
| rupture elongation (%) | | | | | 61 | 35 | 42 | 47 | 52 |
| adhesive force (N) | | | | | 0.18 | 0.19 | 0.78 | 0.52 | 0.12 |
| shock absorbing ability (%) | | | | | 48 | 28 | 47 | 41 | 51 |
| shape restoring test | | | | | A | B | A | A | S |
| structural proportion (%) of (meth)acrylic monomer (A) | | | | | 60 | 40 | 40 | 60 | 60 |
| (meth)acryloyl group concentration (mol/g) of (meth)acrylic monomer (A) | | | | | 0.002 | 0.002 | 4E−04 | 1E−03 | 0.002 |
| molecular weight (g/mol) per (meth)acryloyl group of (meth)acrylic monomer (A) | | | | | 635.4 | 500 | 2500 | 1367 | 635.4 |
| aromatic ring concentration (mol/g) in total monomers | | | | | 0.004 | 0.002 | 0.002 | 0.002 | 0.003 |
| X1 [molecular weight of (meth)acrylic monomer (A) per (meth)acryloyl group]/Y [aromatic ring concentration (mol/g) in (meth)acrylic monomer component] ($\times 10^4$ $g^2/mol^2$) | | | | | 18 | 20 | 100 | 56 | 22 |
| aromatic ring concentration (mol/g) in (meth)acrylic monomer (A) | | | | | 6E−04 | 0 | 0 | 0 | 6E−04 |

TABLE 3-continued

| | component | name | Mw | molecular weight (g/mol) per (meth)-acrylic functional group | Ex 39 A | Ex 40 A | Ex 41 A | Ex 42 A | Ex 43 A |
|---|---|---|---|---|---|---|---|---|---|
| composition | (meth)-acrylic monomer (A) | UA-160TM | 1600 | 800 | 40 | 40 | 40 | 30 | |
| | | UA-122P | 1100 | 550 | | | | | |
| | | UN-6305 | 27000 | 13500 | | | | | |
| | | UN-2700 | 2000 | 1000 | | | | | |
| | | UN-2600 | 2500 | 1250 | | | | | |
| | | UN-352 | 3000 | 1500 | | | | | |
| | | UN-333 | 3000 | 1500 | | | | | |
| | | SUA-01 | 1680 | 840 | | | | | |
| | | SUA-02 | 1680 | 840 | | | | | |
| | | SUA-03 | 1734 | 867 | | | | | |
| | | SUA-04 | 1734 | 867 | | | | | |
| | | SUA-05 | 1734 | 867 | | | | | |
| | | AH-600 | 612.68 | 306.34 | | | | | |
| | | MMD-352 | 632.67 | 316.335 | 20 | 20 | 15 | | 40 |
| | | Ebecryl8402 | 1000 | 500 | | | | | |
| | | Ebecryl230 | 5000 | 2500 | | | | | |
| composition | other (meth)-acrylic monomers | 4EG | 330.38 | 165.19 | | | | | |
| | (meth)-acrylic monomer (B) | PO-A | 192.21 | 192.21 | | | | | |
| | | P2H-A | 236.27 | 236.27 | 20 | | | | |
| | | POBA | 254.29 | 254.29 | 20 | 40 | 45 | | 60 |
| | | M-600A | 222.24 | 222.24 | | | | | |
| | | M110 | 319.2 | 319.2 | | | | 70 | |
| | | M111 | 318.46 | 318.46 | | | | | |
| | | M113 | 450.62 | 450.62 | | | | | |
| | | HRD01 | 268.31 | 268.31 | | | | | |
| | | BZ | 176.22 | 176.22 | | | | | |
| | | PO | 206.24 | 206.24 | | | | | |
| | | L-A | 240.39 | 240.39 | | | | | |
| | | THF-A | 156.18 | 156.18 | | | | | |
| composition | photo-polymerization initiator | OmniradTPO | 348.38 | — | 2 | 2 | 2 | 2 | 2 |
| | | Omnirad819 | 418.47 | — | | | | | |
| total | | | | | 102 | 102 | 102 | 102 | 102 |
| viscosity (mPa · s) of composition | | | | | 2320 | 988 | 1670 | 1253 | 620 |
| shore A hardness | | | | | 89 | 92 | 91 | 32 | 96 |
| rupture elongation (%) | | | | | 37 | 47 | 61 | 56 | 24 |
| adhesive force (N) | | | | | 0.17 | 0.07 | 0.1 | 0.76 | 0.08 |
| shock absorbing ability (%) | | | | | 50 | 43 | 49 | 55 | 75 |
| shape restoring test | | | | | S | S | S | A | C |
| structural proportion (%) of (meth)acrylic monomer (A) | | | | | 60 | 60 | 55 | 30 | 40 |
| (meth)acryloyl group concentration (mol/g) of (meth)acrylic monomer (A) | | | | | 0.002 | 0.002 | 0.002 | 0.001 | 0.0032 |
| molecular weight (g/mol) per (meth)acryloyl group of (meth)acrylic monomer (A) | | | | | 638.8 | 638.8 | 668.1 | 800 | 316.34 |
| aromatic ring concentration (mol/g) in total monomers | | | | | 0.003 | 0.004 | 0.004 | 0.004 | 0.0065 |
| X1 [molecular weight of (meth)acrylic monomer (A) per (meth)acryloyl group]/Y [aromatic ring concentration (mol/g) in (meth)acrylic monomer component] ($\times 10^4$ $g^2/mol^2$) | | | | | 19 | 16 | 16 | 19 | 5 |
| aromatic ring concentration (mol/g) in (meth)acrylic monomer (A) | | | | | 9E−04 | 9E−04 | 7E−04 | 0 | 0.0019 |

In Table 1~Table 3, the numbers in the "composition" rows in the respective Examples and the respective Comparative Examples are expressed in parts by mass.

The heading "AE+B (A and B are arbitrary numbers)" in Table 1~Table 3 means A×$10^B$.

Details of the respective components in Table 1~Table 3 are as follows.

<(Meth)Acrylic Monomer (A) Having 2 (Meth)Acryloyloxy Groups and 2 Urethane Bonds>

The respective structures of (meth)acrylic monomers (A) having 2 (meth)acryloyloxy groups and 2 urethane bonds in Table 1~Table 3 are as follows.

In Table 1~Table 3, the numbers in the "composition" rows in the respective Examples and the respective Comparative Examples are expressed in parts by mass.

The heading "AE+B (A and B are arbitrary numbers)" in Table 1~Table 3 means A×$10^B$.

Details of the respective components in Table 1~Table 3 are as follows.

<(Meth)Acrylic Monomer (A) Having 2 (Meth)Acryloyloxy Groups and 2 Urethane Bonds>

The respective structures of (meth)acrylic monomers (A) having 2 (meth)acryloyloxy groups and 2 urethane bonds in Table 1~Table 3 are as follows.

[Chemical Formula 7]

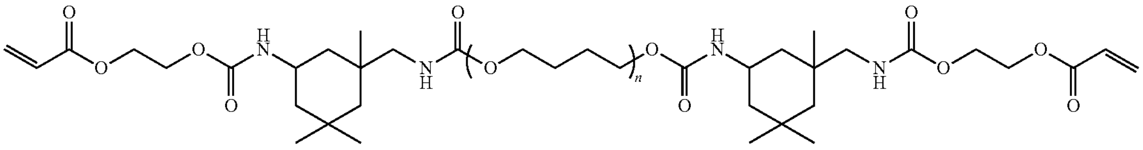

UA-160TM

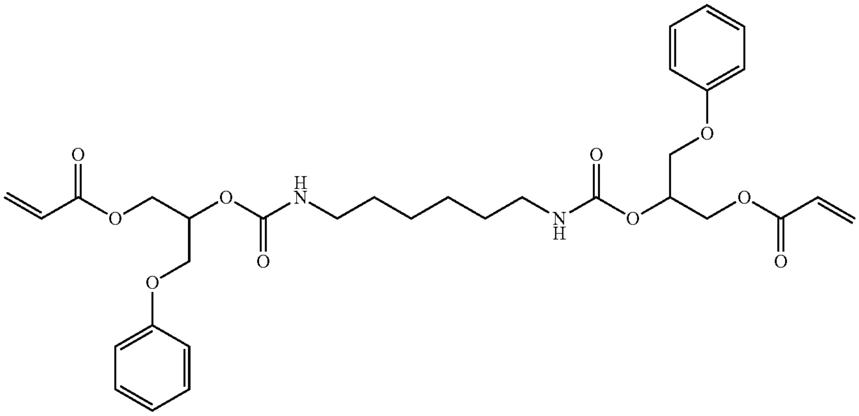

AH-600

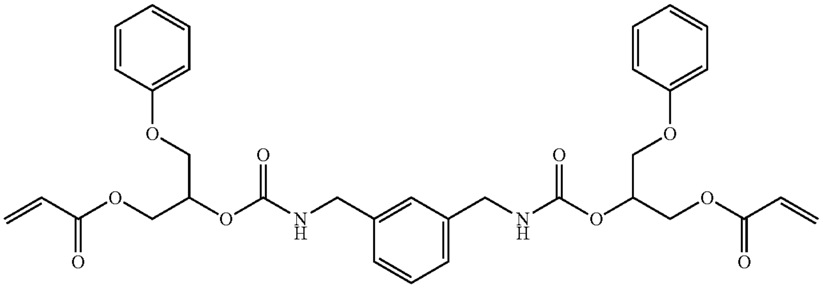

MMD-352

[Chemical Formula 8]

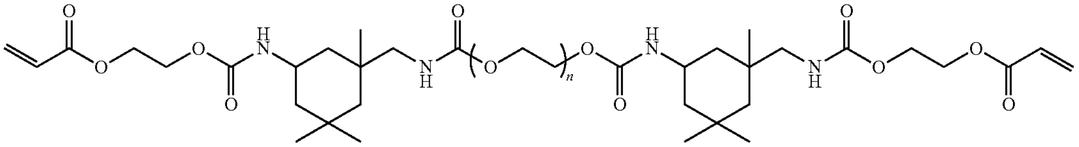

SUA-01

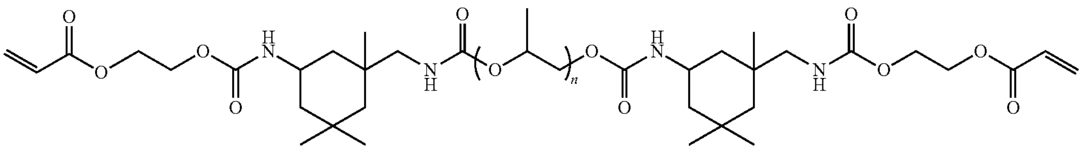

SUA-02

-continued

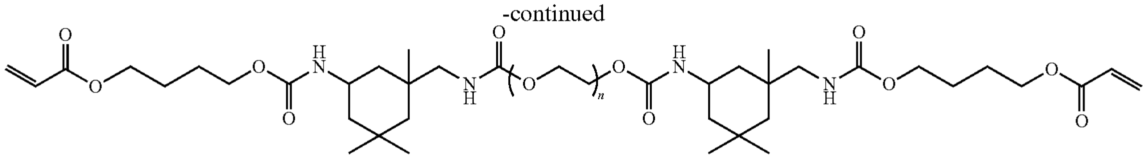

SUA-03

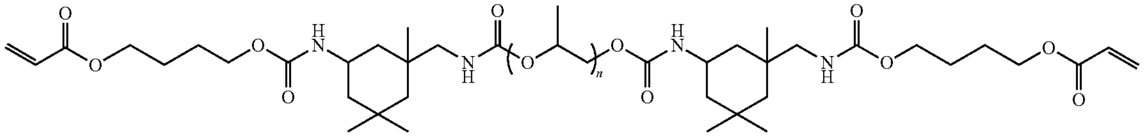

SUA-04

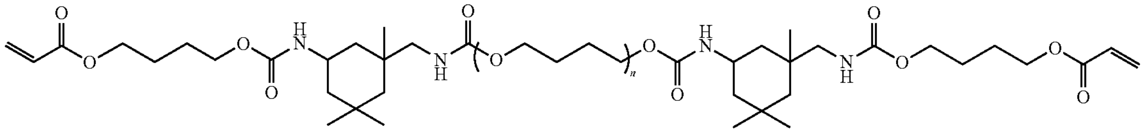

SUA-05

UA-160TM manufactured by Shin Nakamura Chemical Co. Ltd., a urethane diacrylate monomer having a polyether backbone UA-122P manufactured by Shin Nakamura Chemical Co. Ltd., a urethane diacrylate monomer having a polyether backbone UN-6305 manufactured by Negami Chemical Industrial Co., Ltd., a urethane diacrylate monomer having a polyether backbone UN-2700 manufactured by Negami Chemical Industrial Co., Ltd., a urethane diacrylate monomer UN-2600 manufactured by Negami Chemical Industrial Co., Ltd., a urethane diacrylate monomer UN-352 manufactured by Negami Chemical Industrial Co., Ltd., a urethane diacrylate monomer UN-333 manufactured by Negami Chemical Industrial Co., Ltd., a urethane diacrylate monomer having a polyester backbone SUA-01 a compound manufactured by the method put forth in following Manufacturing Example 1A, a urethane diacrylate monomer SUA-02 a compound manufactured by the method put forth in following Manufacturing Example 2A, a urethane diacrylate monomer SUA-03 a compound manufactured by the method put forth in following Manufacturing Example 3A, a urethane diacrylate monomer SUA-04 a compound manufactured by the method put forth in following Manufacturing Example 4A, a urethane diacrylate monomer SUA-05 a compound manufactured by the method put forth in following Manufacturing Example 5A, a urethane diacrylate monomer AH-600 manufactured by Kyoeisha Chemical Co., Ltd., a urethane diacrylate monomer MMD-352 a compound manufactured by the method put forth in following Manufacturing Example 6A, a urethane diacrylate monomer Ebecryl 8402 and Ebecryl 230 manufactured by Daicell Allnex Ltd., urethane diacrylate monomers

Manufacturing Example 1A: Manufacturing of SUA-01

IPDI (isophoron diisocyanate) in an amount of 222 g (1.00 mol), DBTDL (dibutyltin dilaurate) in an amount of 0.84 g (0.1% by weight with respect to the total weight of IPDI, PEG-1000 and HEA), and MEHQ (4-methoxyphenol) in amount of 0.42 g (0.05% by weight with respect to the total weight of IPDI, PEG-1000 and HEA) were added into a 1-liter 4-necked flask equipped with stirring blades that were sufficiently dried and a thermometer, and, after stirring until uniform, the temperature was raised to 60° C. Next, PEG-1000 (molecular weight 1000, manufactured by Toho Chemical Industry Co., Ltd.) in an amount of 500 g (0.50 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

Next, the internal temperature of the flask was maintained at 60° C., and 116 g (1.00 mol) of HEA (2-hydroxyethylacrylate), which had been added to another dropping funnel, was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

At this time, the progression of the reaction was tracked by HPLC analysis, and the end point of the reaction was confirmed. By discharging the products from the reaction vessel, 820 g of urethane acrylate (SUA-01) was obtained. The viscosity at 40° C. was 31000 mPa·s.

Manufacturing Example 2A: Manufacturing of SUA-02

IPDI (isophoron diisocyanate) in an amount of 222 g (1.00 mol), DBTDL (dibutyltin dilaurate) in an amount of 0.84 g (0.1% by weight with respect to the total weight of IPDI, EXCENOL 1020 and HEA), and MEHQ (4-methoxyphenol) in amount of 0.42 g (0.05% by weight with respect to the total weight of IPDI, EXCENOL 1020 and HEA) were added into a 1-liter 4-necked flask equipped with stirring blades that were sufficiently dried and a thermometer, and, after stirring until uniform, the temperature was raised to 60° C. Next, EXCENOL 1020 (molecular weight 1000, manufactured by AGC Chemicals) in an amount of 500 g (0.50 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

Next, the internal temperature of the flask was maintained at 60° C., and 116 g (1.00 mol) of HEA (2-hydroxyethylacrylate), which had been added to another dropping funnel, was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

At this time, the progression of the reaction was tracked by HPLC analysis, and the end point of the reaction was confirmed. By discharging the products from the reaction vessel, 820 g of urethane acrylate (SUA-02) expressed by the above-described formula was obtained. The viscosity at 40° C. was 27000 mPa·s.

Manufacturing Example 3A: Manufacturing of SUA-03

IPDI (isophoron diisocyanate) in an amount of 222 g (1.00 mol), DBTDL (dibutyltin dilaurate) in an amount of 0.87 g (0.1% by weight with respect to the total weight of IPDI, PEG-1000 and 4HBA), and MEHQ (4-methoxyphenol) in amount of 0.43 g (0.05% by weight with respect to the total weight of IPDI, PEG-1000 and 4HBA) were added into a 1-liter 4-necked flask equipped with stirring blades that were sufficiently dried and a thermometer, and, after stirring until uniform, the temperature was raised to 60° C. Next, PEG-1000 (molecular weight 1000, manufactured by Toho Chemical Industry Co., Ltd.) in an amount of 500 g (0.50 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

Next, the internal temperature of the flask was maintained at 60° C., and 144 g (1.00 mol) of 4HBA (4-hydroxybutylacrylate), which had been added to another dropping funnel, was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

At this time, the progression of the reaction was tracked by HPLC analysis, and the end point of the reaction was confirmed. By discharging the products from the reaction vessel, 840 g of urethane acrylate (SUA-03) expressed by the above-described formula was obtained. The viscosity at 40° C. was 45000 mPa·s.

Manufacturing Example 4A: Manufacturing of SUA-04

IPDI (isophoron diisocyanate) in an amount of 222 g (1.00 mol), DBTDL (dibutyltin dilaurate) in an amount of 0.87 g (0.1% by weight with respect to the total weight of IPDI, EXCENOL 1020 and 4HBA), and MEHQ in amount of 0.43 g (0.05% by weight with respect to the total weight of IPDI, EXCENOL 1020 and 4HBA) were added into a 1-liter 4-necked flask equipped with stirring blades that were sufficiently dried and a thermometer, and, after stirring until uniform, the temperature was raised to 60° C. Next, EXCENOL 1020 (molecular weight 1000, manufactured by AGC Chemicals) in an amount of 500 g (0.50 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

Next, the internal temperature of the flask was maintained at 60° C., and 144 g (1.00 mol) of 4HBA (4-hydroxybutylacrylate), which had been added to another dropping funnel, was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

At this time, the progression of the reaction was tracked by HPLC analysis, and the end point of the reaction was confirmed. By discharging the products from the reaction vessel, 840 g of urethane acrylate (SUA-04) expressed by the above-described formula was obtained. The viscosity at 40° C. was 42000 mPa·s.

Manufacturing Example 5A: Manufacturing of SUA-05

IPDI (isophoron diisocyanate) in an amount of 222 g (1.00 mol), DBTDL (dibutyltin dilaurate) in an amount of 0.87 g (0.1% by weight with respect to the total weight of IPDI, PTMG 1000 and 4HBA), and MEHQ (4-methoxyphenol) in amount of 0.43 g (0.05% by weight with respect to the total weight of IPDI, PTMG 1000 and 4HBA) were added into a 1-liter 4-necked flask equipped with stirring blades that were sufficiently dried and a thermometer, and, after stirring until uniform, the temperature was raised to 60° C.

Next, PTMG 1000 (molecular weight 1000, manufactured by Mitsubishi Chemical Corporation) in an amount of 500 g (0.50 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours. Next, the internal temperature of the flask was maintained at 60° C., and 144 g (1.00 mol) of 4HBA (4-hydroxybutyl-acrylate), which had been added to another dropping funnel, was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 5 hours.

At this time, the progression of the reaction was tracked by HPLC analysis, and the end point of the reaction was confirmed. By discharging the products from the reaction vessel, 840 g of urethane acrylate (SUA-05) expressed by the above-described formula was obtained. The viscosity at 40° C. was 38000 mPa·s.

Manufacturing Example 6A: Manufacturing of MMD-352

M-600A (phenylglycidyl ether acrylate, manufactured by Kyoeisha Chemical Co., Ltd.) in an amount of 444 g (2.00 mol), DBTDL (dibutyltin dilaurate) in an amount of 0.63 g, and MEHQ (4-methoxyphenol) in amount of 0.32 g were added into a 1-liter 4-necked flask equipped with stirring blades that were sufficiently dried and a thermometer, and, after stirring until uniform, the temperature was raised to 60° C. Next, XDI (m-xylylene diisocyanate) in an amount of 188 g (1.00 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 10 hours.

At this time, the progression of the reaction was tracked by HPLC analysis, and the end point of the reaction was confirmed. By discharging the products from the reaction vessel, 600 g of urethane diacrylate monomer (MMD-352) was obtained. The viscosity at 65° C. was 6210 mPa·s.

<Other (Meth)Acrylic Monomers>

((Meth)acrylic monomer having two (meth)acryloyloxy groups and not having a urethane bond)

4EG manufactured by Kyoeisha Chemical Co., Ltd., dimethacrylate monomer

[Chemical Fromula 9]

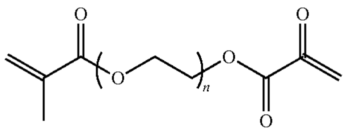

n ≈ 4

4EG

<(Meth)Acrylic Monomer (B) Having One Acryloyl Group>

The respective structures of the (meth)acrylic monomers (B) having one acryloyl group, which are listed in Table 1~Table 3, are as follows.

[Chemical Formula 10]

PO-A

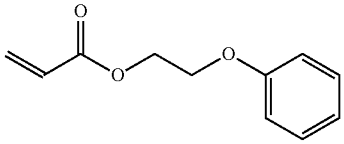

M113

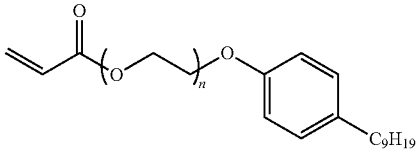

n ≈ 4

-continued

P2H-A

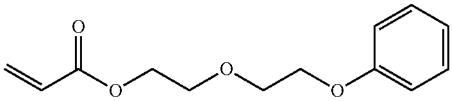

HRD01

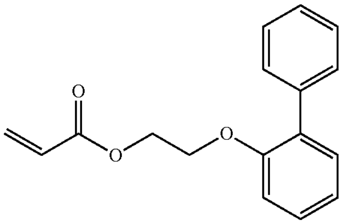

POBA

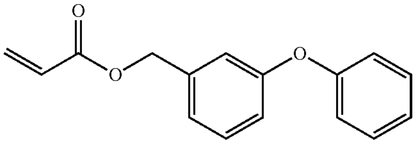

BZ

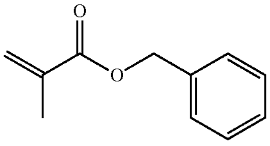

M-600A

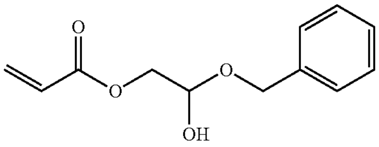

PO

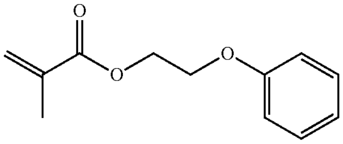

M110

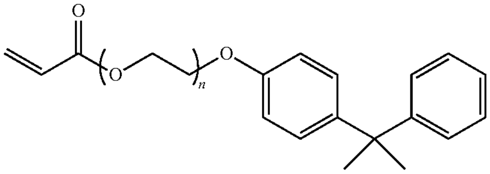

n ≈ 1.2

L-A

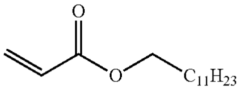

M111

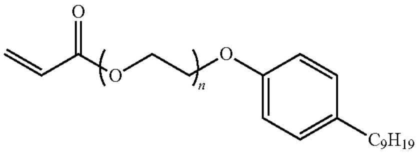

n ≈ 1

-continued

THF-A

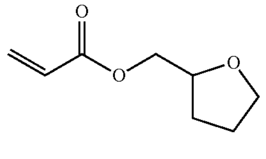

PO-A manufactured by Kyoeisha Chemical Co., Ltd.
P2H-A manufactured by Kyoeisha Chemical Co., Ltd.
POBA manufactured by Kyoeisha Chemical Co., Ltd.
M-600A manufactured by Kyoeisha Chemical Co., Ltd.
M110, M111, M113 manufactured by Toagosei Co., Ltd.
HRD01 manufactured by Nisshoku Techno Fine Chemical Co., Ltd.
BZ manufactured by Kyoeisha Chemical Co., Ltd.
PO manufactured by Kyoeisha Chemical Co., Ltd.
L-A manufactured by Kyoeisha Chemical Co., Ltd.
THF-A manufactured by Kyoeisha Chemical Co., Ltd.

<Photopolymerization Initiator>

The respective structures of the photopolymerization initiators that are listed in Table 1~Table 3 are as follows.

[Chemical Formula 11]

OmniradTPO

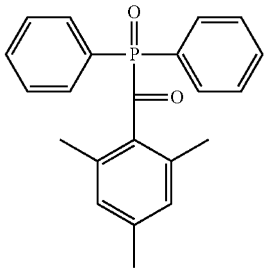

Omnirad819

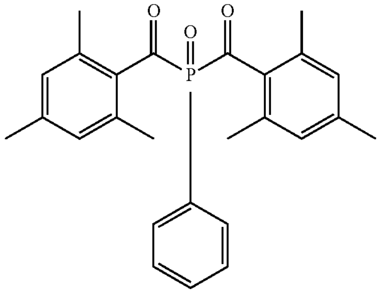

Omnirad TPO is manufactured by IGM Resins.
Omnirad 819 is manufactured by IGM Resins.

As shown in Table 1~Table 3, in Examples that contained a (meth)acrylic monomer component and a photopolymerization initiator, and in which the adhesive force of the cured product was less than or equal to 1.5 N, and in which the rupture elongation of the cured product was greater than or equal to 20%, a cured product that had excellent rupture elongation and in which the adhesive force was kept down could be obtained.

Further, in cured products of Examples that contained a (meth)acrylic monomer component and a photopolymerization initiator, and in which the adhesive force of the cured product was less than or equal to 1.5 N, and in which the rupture elongation of the cured product was greater than or equal to 20%, the shape restorability in the shape restoring test was high, and the occurrence of breaks and fissures was suppressed.

Further, in Examples that contained a (meth)acrylic monomer component and a photopolymerization initiator, and in which the adhesive force of the cured product was less than or equal to 1.5 N, and in which the shock absorbing ability of the cured product was greater than or equal to 20% and less than or equal to 80%, a cured product that had excellent rupture elongation and in which the adhesive force was kept down could be obtained.

Further, in cured products of Examples that contained a (meth)acrylic monomer component and a photopolymerization initiator, and in which the adhesive force of the cured product was less than or equal to 1.5 N, and in which the shock absorbing ability of the cured product was greater than or equal to 20% and less than or equal to 80%, the shape restorability in the shape restoring test was high, and the occurrence of breaks and fissures was suppressed. Further, in Examples in which the (meth)acrylic monomer component contained (meth)acrylic monomer (A) having two (meth) acryloyl groups and (meth)acrylic monomer (B) having one (meth)acryloyl group, a cured product that had excellent rupture elongation and in which the adhesive force was kept down could be obtained.

Further, in cured products of Examples that contained a (meth)acrylic monomer component and a photopolymerization initiator, and in which the adhesive force of the cured product was less than or equal to 1.5 N, and in which the shock absorbing ability of the cured product was greater than or equal to 20% and less than or equal to 80%, the shape restorability in the shape restoring test was high, and the occurrence of breaks and fissures was suppressed.

On the other hand, in the cured product that was obtained in Comparative Example 1A, the adhesive force was not kept down. The cured products obtained in Comparative Examples 2A and 3A had inferior rupture elongation. In the cured products of Comparative Examples 1A~3A, breaks and fissures arose in the shape restoring test.

Further, (a) it was understood that, in Examples 40A and 41A in which (meth)acrylic monomer (A) contained (meth) acrylic monomer (A-1) in which the molecular weight per one (meth)acryloyl group was greater than or equal to 300 g/mol and less than or equal to 600 g/mol, and (meth)acrylic monomer (A-2) in which the molecular weight per one (meth)acryloyl group was greater than 600 g/mol and was less than or equal to 15000 g/mol, after the stress was released, the cured product was restored to its original shape in greater than or equal to 0 seconds and less than 1 second, and had excellent shape restorability.

(b) It was understood that, in Examples 7A, 12A, 14A, 15A and 18A that contained (meth)acrylic monomer (B-1) having two aromatic rings, and (meth)acrylic monomer (B-2) having one aromatic ring, after the stress was released, the cured product was restored to its original shape in greater than or equal to 0 seconds and less than 1 second, and had excellent shape restorability.

It was understood that, in Examples 38A and 39A that satisfied both conditions (a) and (b), after the stress was released, the cured product was restored to its original shape in greater than or equal to 0 seconds and less than 1 second, and had excellent shape restorability.

Examples B

Examples B are Examples for more specifically describing the second embodiment of the present disclosure.

<Preparation of Photocurable Composition>

Examples 1B~35B, Comparative Example 2B

The respective components listed in following Table 4~Table 7 were mixed-together, and photocurable compositions were obtained. The viscosities of the respective photocurable compositions are shown in Table 4~Table 7.

Note that the aforementioned viscosity was measured by a method similar to the above-described method.

Comparative Example 1B

A Gingiva Mask (manufactured by NextDent B.V,) was used as the photocurable composition.

<Evaluation>

The following measurements and evaluations were carried out on the test pieces that were obtained. The results are shown in Table 4~Table 7.

(Rupture Elongation)

The obtained photocurable composition was shaped into the shape of a dumbbell-type test piece conforming to ISO 37-2 by using a 3D printer (Kulzer LLC, CaraPrint 4.0) under the conditions of the wavelength of the visible light being 405 nm and the illuminance of the visible light being 8.0 mJ/cm$^2$, and a shaped product (layered width 50 μm) was obtained. By illuminating ultraviolet light of a wavelength of 365 nm under the condition of 10 J/cm$^2$ onto the shaped product that was obtained, and definitively curing the shaped product, a photoshaped product (i.e., cured product) was obtained.

The rupture elongation of the photoshaped product that was obtained (hereinafter called "test piece") was measured in accordance with ISO 37: 2017. These measurements were carried out by using a tensile testing device (manufactured by Shimadzu Corporation) and under the condition of a pulling speed of 500±50 mm/minute.

(Shore A Hardness)

The obtained photocurable composition was shaped to length 25 mm×width 25 mm×thickness 6 mm, by using a 3D printer (Kulzer LLC, CaraPrint 4.0) and under the conditions of the wavelength of the visible light being 405 nm and the illuminance of the visible light being 8.0 mJ/cm$^2$, and a shaped product (layered width 50 μm) was obtained. By illuminating ultraviolet light of a wavelength of 365 nm under the condition of 10 J/cm$^2$ onto the shaped product that was obtained, and definitively curing the shaped product, a photoshaped product (i.e., cured product) was obtained.

The shore A hardness of the photoshaped product that was obtained (hereinafter called "test piece") was measured in accordance with ISO 7619-1: 2010. In measuring the hardness, a durometer-type hardness tester (manufactured by Mitutoyo Corporation) was used, and the numerical value after 15 seconds after needle insertion was used as the value of the shore A hardness.

(Adhesive Force)

The obtained photocurable composition was shaped to length 20 mm×width 20 mm×thickness 2 mm, by using a 3D printer (Kulzer LLC, CaraPrint 4.0) and under the conditions of the wavelength of the visible light being 405 nm and the illuminance of the visible light being 8.0 mJ/cm$^2$, and a shaped product (layered width 50 μm) was obtained. By illuminating ultraviolet light of a wavelength of 365 nm under the condition of 10 J/cm$^2$ onto the shaped product that was obtained, and definitively curing the shaped product, a photoshaped product was obtained.

The photoshaped product that was obtained (hereinafter called "test piece") was affixed to a sample stand such that there was no slack therein. Next, a probe, which was made of aluminum and whose contact surface area was length 10 mm×width 10 mm, and a 20 mm long×20 mm wide surface of the test piece, were made to contact one another, and were left for 1.0±0.1 seconds at a contact load of 0.98±0.01 N/cm$^2$.

Thereafter, by using a tensile testing device (manufactured by Shimadzu Corporation), the aforementioned probe was pulled-off from the contact surface in the vertical direction at a speed of 5±0.5 mm per second. Then, the maximum load needed at the time of pulling the aforementioned probe off from the contact surface was determined, and was used as the adhesive force (unit: N) of the cured product.

TABLE 4

| | component | name | Mw | molecular weight (g/mol) per (meth)-acrylic functional group | number of aromatic rings in monomer | CoEx 1B | CoEx 2B | Ex1B | Ex2B | Ex3B |
|---|---|---|---|---|---|---|---|---|---|---|
| composition | (meth)-acrylic monomer (A) | UA-160TM | 1600 | 800 | 0 | — | | 30 | 40 | 40 |
| | | UA-122P | 1100 | 550 | 0 | — | | | | |
| | | UN-6305 | 27000 | 13500 | 0 | — | | | | |
| | | UN-2700 | 2000 | 1000 | 0 | — | | | | |
| | | UN-2600 | 2500 | 1250 | 0 | — | | | | |
| | | UN-352 | 3000 | 1500 | 0 | — | | | | |
| | | AH-600 | 612.68 | 306.34 | 2 | — | | | | |
| | | MMD-352 | 632.67 | 316.335 | 3 | — | | | | |
| | | Ebecryl8402 | 1000 | 500 | 0 | — | | | | |
| | | Ebecryl230 | 5000 | 2500 | 0 | — | | | | |
| | | Ebecryl4859 | 500 | 250 | 0 | — | | | | |
| | | ABE-300 | 468.6 | 234.3 | 2 | | 35 | | | |

TABLE 4-continued

| | | | | | | | | | | |
|---|---|---|---|---|---|---|---|---|---|---|
| compo-sition | (meth)-acrylic monomer (B) | PO-A | 192.21 | 192.21 | 1 | — | | | | |
| | | P2H-A | 236.27 | 236.27 | 1 | — | | 70 | 60 | 60 |
| | | POBA | 254.29 | 254.29 | 2 | — | | | | |
| | | M-600A | 222.24 | 222.24 | 1 | — | | | | |
| | | M110 | 319.2 | 319.2 | 2 | — | | | | |
| | | M111 | 318.46 | 318.46 | 1 | — | | | | |
| | | M113 | 450.62 | 450.62 | 1 | — | | | | |
| | | HRD01 | 268.31 | 268.31 | 2 | — | 65 | | | |
| | | BZ | 176.22 | 176.22 | 1 | — | | | | |
| | | PO | 206.24 | 206.24 | 1 | — | | | | |
| | | L-A | 240.39 | 240.39 | 0 | — | | | | |
| compo-sition | plasti-cizer | D-1000 (PPG) | 1000 | — | 0 | — | | | | |
| | photo-polymeri-zation initiator | OmniradTPO | — | — | — | — | 2 | 2 | 2 | |
| | | OmniradIr819 | — | — | — | — | | | | 2 |
| total | | | | | — | — | 110 | 102 | 102 | 102 |
| viscosity (mPa · s) of composition | | | | | | 1450 | 310 | 357 | 470 | 481 |
| shore A hardness | | | | | — | 65 | 99 | 52 | 55 | 58 |
| rupture elongation (%) | | | | | — | 29.76 | 7.45 | 66.464 | 50.592 | 47.264 |
| adhesive force (N) | | | | | — | 1.72 | 0.02 | 0.64 | 0.52 | 0.27 |
| structural proportion (%) of (meth)acrylic monomer (A) | | | | | — | — | 35 | 30 | 40 | 40 |
| (meth)acryloyl group concen-tration (mol/g) of (meth)acrylic monomer (A) | | | | | — | — | 0.004268032 | 0.00125 | 0.00125 | 0.00125 |
| molecular weight (g/mol) per (meth)acryloyl group of (meth)acrylic monomer (A) | | | | | — | — | 234.3 | 800 | 800 | 800 |
| aromatic ring concentration (mol/g) in total monomers | | | | | — | — | 0.005762685 | 0.002905 | 0.00249 | 0.00249 |

| | compo-nent | name | Mw | molec-ular weight (g/mol) per (meth)-acrylic func-ional group | Ex4B | Ex5B | Ex6B | Ex7B | Ex8B |
|---|---|---|---|---|---|---|---|---|---|
| compo-sition | (meth)-acrylic monomer (A) | UA-160TM | 1600 | 800 | 50 | 60 | 70 | 40 | 40 |
| | | UA-122P | 1100 | 550 | | | | | |
| | | UN-6305 | 27000 | 13500 | | | | | |
| | | UN-2700 | 2000 | 1000 | | | | | |
| | | UN-2600 | 2500 | 1250 | | | | | |
| | | UN-352 | 3000 | 1500 | | | | | |
| | | AH-600 | 612.68 | 306.34 | | | | | |
| | | MMD-352 | 632.67 | 316.335 | | | | | |
| | | Ebecryl8402 | 1000 | 500 | | | | | |
| | | Ebecryl230 | 5000 | 2500 | | | | | |
| | | Ebecryl4859 | 500 | 250 | | | | | |
| | | ABE-300 | 468.6 | 234.3 | | | | | |
| compo-sition | (meth)-acrylic monomer (B) | PO-A | 192.21 | 192.21 | | | | | |
| | | P2H-A | 236.27 | 236.27 | 50 | | | 30 | |
| | | POBA | 254.29 | 254.29 | | 40 | | 30 | 60 |
| | | M-600A | 222.24 | 222.24 | | | | | |
| | | M110 | 319.2 | 319.2 | | | | | |
| | | M111 | 318.46 | 318.46 | | | | | |
| | | M113 | 450.62 | 450.62 | | | | | |
| | | HRD01 | 268.31 | 268.31 | | | 30 | | |
| | | BZ | 176.22 | 176.22 | | | | | |
| | | PO | 206.24 | 206.24 | | | | | |
| | | L-A | 240.39 | 240.39 | | | | | |

TABLE 4-continued

| | | | | | | | | | |
|---|---|---|---|---|---|---|---|---|---|
| compo-sition | plasti-cizer | D-1000 (PPG) | 1000 | — | | | | | |
| | photo-polymeri-zation | OmniradTPO | — | — | 2 | 2 | 2 | 2 | 2 |
| | initiator | OmniradIr819 | — | — | | | | | |
| total | | | | | 102 | 102 | 102 | 102 | 102 |
| viscosity (mPa · s) of composition | | | | | 1228 | 2350 | 3560 | 425 | 468 |
| shore A hardness | | | | | 58 | 63 | 65 | 60 | 83 |
| rupture elongation (%) | | | | | 52.576 | 54.56 | 47.616 | 64.976 | 88.3 |
| adhesive force (N) | | | | | 0.32 | 0.08 | 0.07 | 0.14 | 0.44 |
| structural proportion (%) of (meth)acrylic monomer (A) | | | | | 50 | 60 | 70 | 40 | 40 |
| (meth)acryloyl group concen-tration (mol/g) of (meth)acrylic monomer (A) | | | | | 0.00125 | 0.00125 | 0.00125 | 0.00125 | 0.00125 |
| molecular weight (g/mol) per (meth)acryloyl group of (meth)acrylic monomer (A) | | | | | 800 | 800 | 800 | 800 | 800 |
| aromatic ring concentration (mol/g) in total monomers | | | | | 0.002075 | 0.003084 | 0.002192 | 0.003558 | 0.004626 |

TABLE 5

| | compo-nent | name | Mw | molec-ular weight (g/mol) per (meth)-acrylic func-tional group | num-ber of aro-matic rings in mono-mer | Ex9 B | Ex10 B | Ex11 B | Ex12 B | Ex13 B |
|---|---|---|---|---|---|---|---|---|---|---|
| compo-sition | (meth)-acrylic monomer (A) | UA-160TM | 1600 | 800 | 0 | 30 | 40 | 40 | 40 | 40 |
| | | UA-122P | 1100 | 550 | 0 | | | | | |
| | | UN-6305 | 27000 | 13500 | 0 | | | | | |
| | | UN-2700 | 2000 | 1000 | 0 | | | | | |
| | | UN-2600 | 2500 | 1250 | 0 | | | | | |
| | | UN-352 | 3000 | 1500 | 0 | | | | | |
| | | AH-600 | 612.68 | 306.34 | 2 | | | | | |
| | | MMD-352 | 632.67 | 316.335 | 3 | | | | | |
| | | Ebecryl8402 | 1000 | 500 | 0 | | | | | |
| | | Ebecryl230 | 5000 | 2500 | 0 | | | | | |
| | | Ebecryl4859 | 500 | 250 | 0 | | | | | |
| | | ABE-300 | 468.6 | 234.3 | 2 | | | | | |
| compo-sition | (meth)-acrylic monomer (B) | PO-A | 192.21 | 192.21 | 1 | | | | | |
| | | P2H-A | 236.27 | 236.27 | 1 | | 30 | 30 | 30 | |
| | | POBA | 254.29 | 254.29 | 2 | 70 | | | | |
| | | M-600A | 222.24 | 222.24 | 1 | | 30 | | | |
| | | M110 | 319.2 | 319.2 | 2 | | | 30 | | 30 |
| | | M111 | 318.46 | 318.46 | 1 | | | | 30 | |
| | | M113 | 450.62 | 450.62 | 1 | | | | | |
| | | HRD01 | 268.31 | 268.31 | 2 | | | | | |
| | | BZ | 176.22 | 176.22 | 1 | | | | | |
| | | PO | 206.24 | 206.24 | 1 | | | | | |
| | | L-A | 240.39 | 240.39 | 0 | | | | | 30 |
| compo-sition | plasti-cizer | D-1000 (PPG) | 1000 | — | 0 | | | | | |
| | photo-polymeri-zation | OmniradTPO | — | — | — | 2 | 2 | 2 | 2 | 2 |
| | initiator | OmniradIr819 | — | — | — | | | | | |
| total | | | | | — | 102 | 102 | 102 | 102 | 102 |
| viscosity (mPa · s) of composition | | | | | | 326 | 721 | 632 | 354 | 311 |
| shore A hardness | | | | | — | 76 | 53 | 62 | 64 | 54 |
| rupture elongation (%) | | | | | — | 102.5 | 74.896 | 84.816 | 51.088 | 30.752 |
| adhesive force (N) | | | | | — | 0.77 | 0.45 | 0.62 | 0.39 | 0.55 |
| structural proportion (%) of (meth)acrylic monomer (A) | | | | | — | 30 | 40 | 40 | 40 | 40 |

TABLE 5-continued

| | | | | | | |
|---|---|---|---|---|---|---|
| (meth)acryloyl group concentration (mol/g) of (meth)acrylic monomer (A) | — | 0.00125 | 0.00125 | 0.00125 | 0.00125 | 0.00125 |
| molecular weight (g/mol) per (meth)acryloyl group of (meth)acrylic monomer (A) | — | 800 | 800 | 800 | 800 | 800 |
| aromatic ring concentration (mol/g) in total monomers | — | 0.005398 | 0.002568 | 0.003088 | 0.002168 | 0.001843 |

| | component | name | Mw | molecular weight (g/mol) per (meth)-acrylic functional group | Ex14 B | Ex15 B | Ex16 B | Ex17 B | Ex18 B |
|---|---|---|---|---|---|---|---|---|---|
| composition | (meth)-acrylic monomer (A) | UA-160TM | 1600 | 800 | 40 | 40 | 40 | 40 | 40 |
| | | UA-122P | 1100 | 550 | | | | | |
| | | UN-6305 | 27000 | 13500 | | | | | |
| | | UN-2700 | 2000 | 1000 | | | | | |
| | | UN-2600 | 2500 | 1250 | | | | | |
| | | UN-352 | 3000 | 1500 | | | | | |
| | | AH-600 | 612.68 | 306.34 | | | | | |
| | | MMD-352 | 632.67 | 316.335 | | | | | |
| | | Ebecryl8402 | 1000 | 500 | | | | | |
| | | Ebecryl230 | 5000 | 2500 | | | | | |
| | | Ebecryl4859 | 500 | 250 | | | | | |
| | | ABE-300 | 468.6 | 234.3 | | | | | |
| composition | (meth)-acrylic monomer (B) | PO-A | 192.21 | 192.21 | | | | | 30 |
| | | P2H-A | 236.27 | 236.27 | | 30 | 30 | 30 | |
| | | POBA | 254.29 | 254.29 | 30 | | | | |
| | | M-600A | 222.24 | 222.24 | | | | | |
| | | M110 | 319.2 | 319.2 | | | | | |
| | | M111 | 318.46 | 318.46 | | | | | |
| | | M113 | 450.62 | 450.62 | 30 | | | | |
| | | HRD01 | 268.31 | 268.31 | | 30 | | | 30 |
| | | BZ | 176.22 | 176.22 | | | 30 | | |
| | | PO | 206.24 | 206.24 | | | | 30 | |
| | | L-A | 240.39 | 240.39 | | | | | |
| composition | plasticizer | D-1000 (PPG) | 1000 | — | | | | | |
| | photopolymerization initiator | OmniradTPO | — | — | 2 | 2 | 2 | 2 | 2 |
| | | OmniradIr819 | — | — | | | | | |
| total | | | | | 102 | 102 | 102 | 102 | 102 |
| viscosity (mPa · s) of composition | | | | | 562 | 670 | 467 | 696 | 571 |
| shore A hardness | | | | | 76 | 65 | 89 | 87 | 73 |
| rupture elongation (%) | | | | | 34.224 | 74.896 | 36.944 | 35.376 | 50.6 |
| adhesive force (N) | | | | | 0.32 | 0.21 | 0.15 | 0.2 | 0.11 |
| structural proportion (%) of (meth)acrylic monomer (A) | | | | | 40 | 40 | 40 | 40 | 40 |
| (meth)acryloyl group concentration (mol/g) of (meth)acrylic monomer (A) | | | | | 0.00125 | 0.00125 | 0.00125 | 0.00125 | 0.00125 |
| molecular weight (g/mol) per (meth)acryloyl group of (meth)acrylic monomer (A) | | | | | 800 | 800 | 800 | 800 | 800 |
| aromatic ring concentration (mol/g) in total monomers | | | | | 0.002966 | 0.003437 | 0.002914 | 0.002671 | 0.003723 |

TABLE 6

| molecular weight (g/mol) per (meth)-acrylic func- | number of aromatic rings in |
|---|---|

TABLE 6-continued

| | compo-nent | name | Mw | ional group | mono-mer | Ex19 B | Ex20 B | Ex21 B | Ex22 B | Ex23 B |
|---|---|---|---|---|---|---|---|---|---|---|
| compo-sition | (meth)-acrylic monomer (A) | UA-160TM | 1600 | 800 | 0 | | | | | |
| | | UA-122P | 1100 | 550 | 0 | 40 | | | | |
| | | UN-6305 | 27000 | 13500 | 0 | | 40 | | | |
| | | UN-2700 | 2000 | 1000 | 0 | | | 40 | | |
| | | UN-2600 | 2500 | 1250 | 0 | | | | 40 | |
| | | UN-352 | 3000 | 1500 | 0 | | | | | |
| | | AH-600 | 612.68 | 306.34 | 2 | | | | | 30 |
| | | MMD-352 | 632.67 | 316.335 | 3 | | | | | |
| | | Ebecryl8402 | 1000 | 500 | 0 | | | | | |
| | | Ebecryl230 | 5000 | 2500 | 0 | | | | | |
| | | Ebecryl4859 | 500 | 250 | 0 | | | | | |
| | | ABE-300 | 468.6 | 234.3 | 2 | | | | | |
| compo-sition | (meth)-acrylic monomer (B) | PO-A | 192.21 | 192.21 | 1 | | | | | |
| | | P2H-A | 236.27 | 236.27 | 1 | 60 | | 60 | 60 | |
| | | POBA | 254.29 | 254.29 | 2 | | | | | |
| | | M-600A | 222.24 | 222.24 | 1 | | | | | 70 |
| | | M110 | 319.2 | 319.2 | 2 | | | | | |
| | | M111 | 318.46 | 318.46 | 1 | | | | | |
| | | M113 | 450.62 | 450.62 | 1 | | | | | |
| | | HRD01 | 268.31 | 268.31 | 2 | | 60 | | | |
| | | BZ | 176.22 | 176.22 | 1 | | | | | |
| | | PO | 206.24 | 206.24 | 1 | | | | | |
| | | L-A | 240.39 | 240.39 | 0 | | | | | |
| compo-sition | plasti-cizer | D-1000 (PPG) | 1000 | — | 0 | | | | | |
| | photo-polymeri-zation initiator | OmniradTPO | — | — | — | 2 | 2 | 2 | 2 | 2 |
| | | OmniradIr819 | — | — | — | | | | | |
| total | | | | | — | 102 | 102 | 102 | 102 | 102 |
| viscosity (mPa · s) of composition | | | | | | 241 | 2890 | 722 | 802 | 854 |
| shore A hardness | | | | | — | 76 | 57 | 78 | 65 | 93 |
| rupture elongation (%) | | | | | — | 44.1 | 82.2 | 47.616 | 62 | 24.2 |
| adhesive force (N) | | | | | — | 0.14 | 0.75 | 0.64 | 0.72 | 0.19 |
| structural proportion (%) of (meth)acrylic monomer (A) | | | | | — | 40 | 40 | 40 | 40 | 30 |
| (meth)acryloyl group concen-tration (mol/g) of (meth)acrylic monomer (A) | | | | | — | 0.001818 | 7.41E−05 | 0.001 | 0.0008 | 0.003264 |
| molecular weight (g/mol) per (meth)acryloyl group of (meth)acrylic monomer (A) | | | | | — | 550 | 13500 | 1000 | 1250 | 306.34 |
| aromatic ring concentration (mol/g) in total monomers | | | | | — | 0.00249 | 0.004385 | 0.00249 | 0.00249 | 0.004048 |

| | compo-nent | name | Mw | molec-ular weight (g/mol) per (meth)-acrylic func-ional group | Ex24 B | Ex25 B | Ex26 B | Ex27 B | Ex28 B |
|---|---|---|---|---|---|---|---|---|---|
| compo-sition | (meth)-acrylic monomer (A) | UA-160TM | 1600 | 800 | | | | 40 | |
| | | UA-122P | 1100 | 550 | | | | | |
| | | UN-6305 | 27000 | 13500 | | | | | |
| | | UN-2700 | 2000 | 1000 | | | | | |
| | | UN-2600 | 2500 | 1250 | | | | | |
| | | UN-352 | 3000 | 1500 | | | 40 | | |
| | | AH-600 | 612.68 | 306.34 | | | | 20 | |
| | | MMD-352 | 632.67 | 316.335 | 30 | 30 | | | |
| | | Ebecryl8402 | 1000 | 500 | | | | | 40 |
| | | Ebecryl230 | 5000 | 2500 | | | | | |
| | | Ebecryl4859 | 500 | 250 | | | | | |
| | | ABE-300 | 468.6 | 234.3 | | | | | |
| compo-sition | (meth)-acrylic monomer (B) | PO-A | 192.21 | 192.21 | | | | | |
| | | P2H-A | 236.27 | 236.27 | | | 60 | | 60 |
| | | POBA | 254.29 | 254.29 | | | | | |
| | | M-600A | 222.24 | 222.24 | 70 | | | | |
| | | M110 | 319.2 | 319.2 | | 70 | | | |
| | | M111 | 318.46 | 318.46 | | | | | |
| | | M113 | 450.62 | 450.62 | | | | | |

TABLE 6-continued

| | | | | | | | | | |
|---|---|---|---|---|---|---|---|---|---|
| | | HRD01 | 268.31 | 268.31 | | | | 40 | |
| | | BZ | 176.22 | 176.22 | | | | | |
| | | PO | 206.24 | 206.24 | | | | | |
| | | L-A | 240.39 | 240.39 | | | | | |
| compo-sition | plasti-cizer | D-1000 (PPG) | 1000 | — | | | | | |
| | photo-polymeri-zation initiator | OmniradTPO | — | — | 2 | 2 | 2 | 2 | 2 |
| | | OmniradIr819 | — | — | | | | | |
| total | | | | | 102 | 102 | 102 | 102 | 102 |
| viscosity (mPa · s) of composition | | | | | 1248 | 1336 | 886 | 1920 | 349 |
| shore A hardness | | | | | 95 | 93 | 89 | 93 | 91 |
| rupture elongation (%) | | | | | 24.6 | 30.4 | 42.32 | 61.008 | 35.2 |
| adhesive force (N) | | | | | 0.13 | 0.09 | 0.54 | 0.18 | 0.19 |
| structural proportion (%) of (meth)acrylic monomer (A) | | | | | 30 | 30 | 40 | 60 | 40 |
| (meth)acryloyl group concen-tration (mol/g) of (meth)acrylic monomer (A) | | | | | 0.003161 | 0.003161 | 0.000667 | 0.001921 | 0.002 |
| molecular weight (g/mol) per (meth)acryloyl group of (meth)acrylic monomer (A) | | | | | 316.335 | 316.335 | 1500 | 635.4467 | 500 |
| aromatic ring concentration (mol/g) in total monomers | | | | | 0.004483 | 0.005695 | 0.00249 | 0.003563 | 0.00249 |

TABLE 7

| | compo-nent | name | Mw | molec-ular weight (g/mol) per (meth)-acrylic func-ional group | num-ber of aro-matic rings in mono-mer | Ex29 B | Ex30 B | Ex31 B | Ex32 B |
|---|---|---|---|---|---|---|---|---|---|
| compo-sition | (meth)-acrylic monomer (A) | UA-160TM | 1600 | 800 | 0 | | 40 | 40 | 40 |
| | | UA-122P | 1100 | 550 | 0 | | | | |
| | | UN-6305 | 27000 | 13500 | 0 | | | | |
| | | UN-2700 | 2000 | 1000 | 0 | | | | |
| | | UN-2600 | 2500 | 1250 | 0 | | | | |
| | | UN-352 | 3000 | 1500 | 0 | | | | |
| | | AH-600 | 612.68 | 306.34 | 2 | | | | 20 |
| | | MMD-352 | 632.67 | 316.335 | 3 | | | | |
| | | Ebecryl8402 | 1000 | 500 | 0 | | | | |
| | | Ebecryl230 | 5000 | 2500 | 0 | 40 | 20 | | |
| | | Ebecryl4859 | 500 | 250 | 0 | | | 20 | |
| | | ABE-300 | 468.6 | 234.3 | 2 | | | | |
| compo-sition | (meth)-acrylic monomer (B) | PO-A | 192.21 | 192.21 | 1 | | | | |
| | | P2H-A | 236.27 | 236.27 | 1 | 60 | | | 20 |
| | | POBA | 254.29 | 254.29 | 2 | | | 40 | |
| | | M-600A | 222.24 | 222.24 | 1 | | | | |
| | | M110 | 319.2 | 319.2 | 2 | | 40 | | |
| | | M111 | 318.46 | 318.46 | 1 | | | | |
| | | M113 | 450.62 | 450.62 | 1 | | | | |
| | | HRD01 | 268.31 | 268.31 | 2 | | | | 20 |
| | | BZ | 176.22 | 176.22 | 1 | | | | |
| | | PO | 206.24 | 206.24 | 1 | | | | |
| | | L-A | 240.39 | 240.39 | 0 | | | | |
| compo-sition | plasti-cizer | D-1000 (PPG) | 1000 | — | 0 | | | | |
| | photo-polymeri-zation initiator | OmniradTPO | — | — | — | 2 | 2 | 2 | 2 |
| | | OmniradIr819 | — | — | — | | | | |
| total | | | | | — | 102 | 102 | 102 | 102 |
| viscosity (mPa · s) of composition | | | | | | 862 | 1543 | 912 | 1354 |
| shore A hardness | | | | | — | 71 | 91 | 93 | 94 |
| rupture elongation (%) | | | | | — | 42.16 | 47.12 | 77.376 | 51.584 |
| adhesive force (N) | | | | | — | 0.78 | 0.52 | 0.08 | 0.12 |

TABLE 7-continued

| | | | | | |
|---|---|---|---|---|---|
| structural proportion (%) of (meth)acrylic monomer (A) | — | 40 | 60 | 60 | 60 |
| (meth)acryloyl group concentration (mol/g) of (meth)acrylic monomer (A) | — | 0.0004 | 0.000967 | 0.002167 | 0.001921 |
| molecular weight (g/mol) per (meth)acryloyl group of (meth)acrylic monomer (A) | — | 2500 | 1366.667 | 616.6667 | 635.4467 |
| aromatic ring concentration (mol/g) in total monomers | — | 0.00249 | 0.002457 | 0.003084 | 0.002932 |

| | component | name | Mw | molecular weight (g/mol) per (meth)-acrylic functional group | Ex33 B | Ex34 B | Ex35 B |
|---|---|---|---|---|---|---|---|
| composition | (meth)-acrylic monomer (A) | UA-160TM | 1600 | 800 | 40 | 40 | 40 |
| | | UA-122P | 1100 | 550 | | | |
| | | UN-6305 | 27000 | 13500 | | | |
| | | UN-2700 | 2000 | 1000 | | | |
| | | UN-2600 | 2500 | 1250 | | | |
| | | UN-352 | 3000 | 1500 | | | |
| | | AH-600 | 612.68 | 306.34 | | | |
| | | MMD-352 | 632.67 | 316.335 | 20 | 20 | 15 |
| | | Ebecryl8402 | 1000 | 500 | | | |
| | | Ebecryl230 | 5000 | 2500 | | | |
| | | Ebecryl4859 | 500 | 250 | | | |
| | | ABE-300 | 468.6 | 234.3 | | | |
| composition | (meth)-acrylic monomer (B) | PO-A | 192.21 | 192.21 | | | |
| | | P2H-A | 236.27 | 236.27 | 20 | | |
| | | POBA | 254.29 | 254.29 | 20 | 40 | 45 |
| | | M-600A | 222.24 | 222.24 | | | |
| | | M110 | 319.2 | 319.2 | | | |
| | | M111 | 318.46 | 318.46 | | | |
| | | M113 | 450.62 | 450.62 | | | |
| | | HRD01 | 268.31 | 268.31 | | | |
| | | BZ | 176.22 | 176.22 | | | |
| | | PO | 206.24 | 206.24 | | | |
| | | L-A | 240.39 | 240.39 | | | |
| composition | plasticizer | D-1000 (PPG) | 1000 | — | | | |
| | photopolymerization initiator | OmniradTPO | — | — | 2 | 2 | 2 |
| | | OmniradIr819 | — | — | | | |
| total | | | | | 102 | 102 | 102 |
| viscosity (mPa · s) of composition | | | | | 2320 | 988 | 1670 |
| shore A hardness | | | | | 89 | 92 | 91 |
| rupture elongation (%) | | | | | 37.2 | 47.12 | 60.512 |
| adhesive force (N) | | | | | 0.17 | 0.07 | 0.1 |
| structural proportion (%) of (meth)acrylic monomer (A) | | | | | 60 | 60 | 55 |
| (meth)acryloyl group concentration (mol/g) of (meth)acrylic monomer (A) | | | | | 0.001887 | 0.001887 | 0.001771 |
| molecular weight (g/mol) per (meth)acryloyl group of (meth)acrylic monomer (A) | | | | | 638.7783 | 638.7783 | 668.0914 |
| aromatic ring concentration (mol/g) in total monomers | | | | | 0.003302 | 0.004014 | 0.004167 |

In Table 4~Table 7, the numbers in the "composition" rows in the respective Examples and the respective Comparative Examples are expressed in parts by mass.

The heading "AE+B (A and B are arbitrary numbers)" in Table 4~Table 7 means $A \times 10^B$.

Details of the respective components in Table 4~Table 7 are as follows.

<(Meth)Acrylic Monomer (A) Having 2 (Meth)Acryloyloxy Groups and 2 Urethane Bonds>

The respective structures of (meth)acrylic monomers (A) having 2 (meth)acryloyloxy groups and 2 urethane bonds in Table 4~Table 7 are as follows.

AH-600 manufactured by Kyoeisha Chemical Co., Ltd., a urethane diacrylate monomer MMD-352 a compound manufactured by the method put forth in following Manufacturing Example 1B, a urethane diacrylate monomer Ebecryl 8402 and Ebecryl 230 manufactured by Daicell Allnex Ltd., urethane diacrylate monomers Ebecryl 4859 manufactured by Daicell Allnex Ltd., a urethane diacrylate monomer ABE-300 manufactured by Shin Nakamura Chemical Co. Ltd., ethoxylated bisphenol A diacrylate

[Chemical Formula 12]

UA-160TM

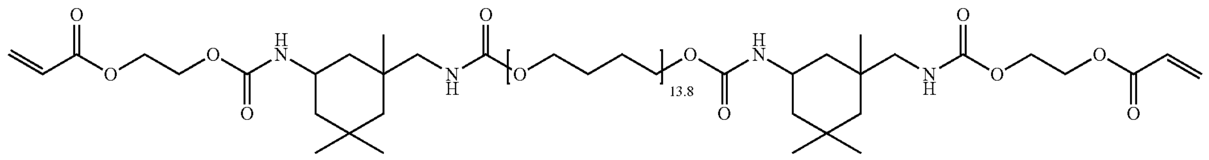

AH-600

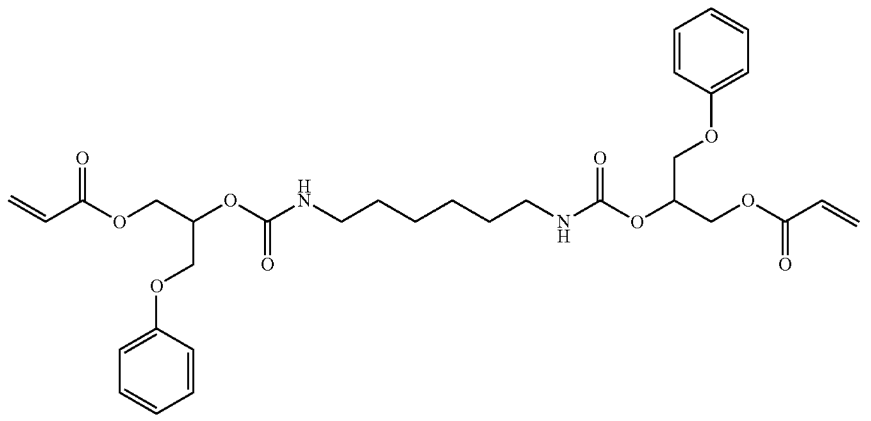

MMD-352

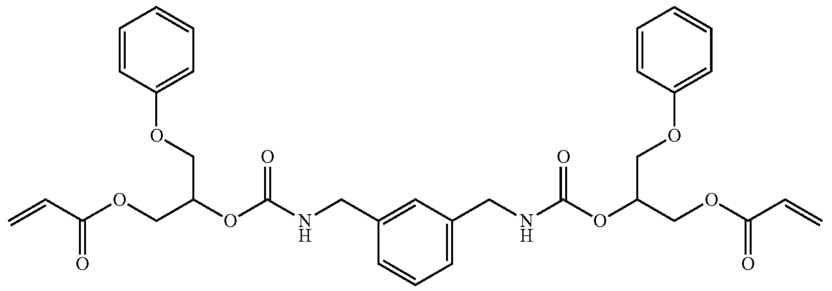

UA-160TM manufactured by Shin Nakamura Chemical Co. Ltd., a urethane diacrylate monomer having a polyether backbone UA-122P manufactured by Shin Nakamura Chemical Co. Ltd., a urethane diacrylate monomer having a polyether backbone UN-6305 manufactured by Negami Chemical Industrial Co., Ltd., a urethane diacrylate monomer having a polyether backbone UN-2700 manufactured by Negami Chemical Industrial Co., Ltd., a urethane diacrylate monomer UN-2600 manufactured by Negami Chemical Industrial Co., Ltd., a urethane diacrylate monomer UN-352 manufactured by Negami Chemical Industrial Co., Ltd., a urethane diacrylate monomer

Manufacturing Example 1B: Manufacturing of MMD-352

M-600A (phenylglycidyl ether acrylate), manufactured by Kyoeisha Chemical Co., Ltd.) in an amount of 444 g (2.00 mol), DBTDL (dibutyltin dilaurate) in an amount of 0.63 g, and MEHQ (4-methoxyphenol) in amount of 0.32 g were added into a 1-liter 4-necked flask equipped with stirring blades that were sufficiently dried and a thermometer, and, after stirring until uniform, the temperature was raised to 60° C. Next, XDI (m-xylylene diisocyanate) in an amount of 188 g (1.00 mol) was added dropwise over one hour. During the dropwise addition, the internal temperature rose due to the reaction heat, and therefore, the amount that was added dropwise was controlled such that the temperature was less than or equal to 80° C. The reaction temperature after the total amount was added dropwise was maintained at 80° C., and the reaction was carried out for 10 hours.

At this time, the progression of the reaction was tracked by HPLC analysis, and the end point of the reaction was confirmed. By discharging the products from the reaction vessel, 600 g of urethane diacrylate monomer (MMD-352) was obtained. The viscosity at 65° C. was 6210 mPa·s.

<(Meth)Acrylic Monomer (B) Having One Acryloyl Group>

The respective structures of the (meth)acrylic monomers (B) having one acryloyl group, which are listed in Table 4~Table 7, are as follows.

[Chemical Formula 13]

PO-A

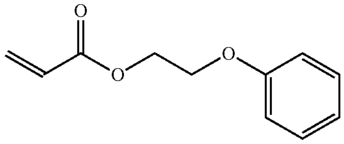

M113

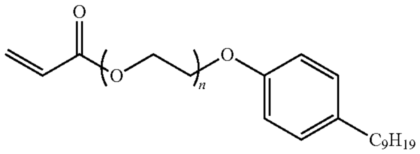

n ≈ 4

P2H-A

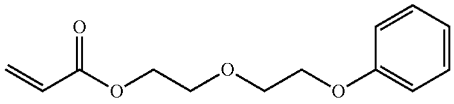

HRD01

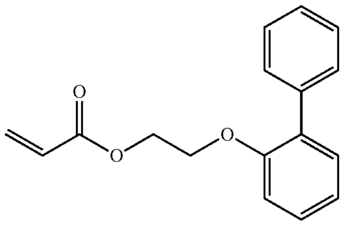

POBA

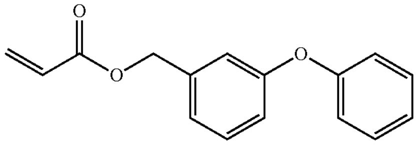

BZ

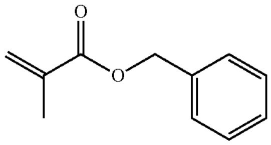

M-600A

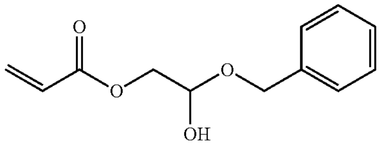

-continued

PO

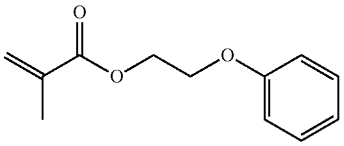

M110

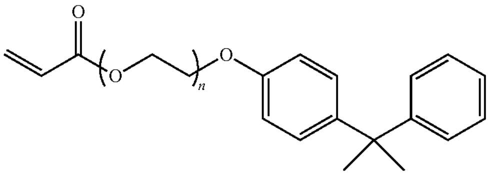

n ≈ 1.2

L-A

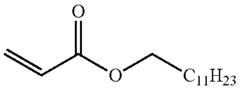

M111

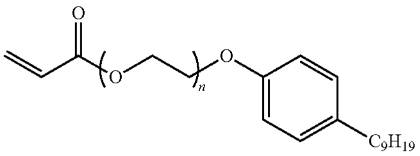

n ≈ 1

THF-A

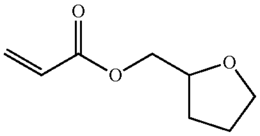

PO-A manufactured by Kyoeisha Chemical Co., Ltd.

P2H-A manufactured by Kyoeisha Chemical Co., Ltd.

POBA manufactured by Kyoeisha Chemical Co., Ltd.

M-600A manufactured by Kyoeisha Chemical Co., Ltd.

M110, M111, M113 manufactured by Toagosei Co., Ltd.

HRD01 manufactured by Nisshoku Techno Fine Chemical Co., Ltd.

BZ manufactured by Kyoeisha Chemical Co., Ltd.

PO manufactured by Kyoeisha Chemical Co., Ltd.

L-A manufactured by Kyoeisha Chemical Co., Ltd.

<Photopolymerization Initiator>

The respective structures of photopolymerization initiators that are listed in Table 4~Table 7 are as follows.

[Chemical Formula 14]

OmniradTPO

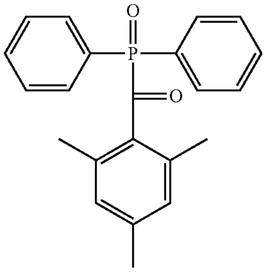

-continued

Omnirad819

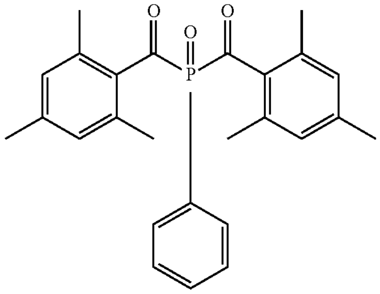

Omnirad TPO is manufactured by IGM Resins.

Omnirad 819 is manufactured by IGM Resins.

As shown in Table 4~Table 7, in the Examples, a cured product that had excellent rupture elongation and in which the adhesive force was kept down could be obtained.

On the other hand, in the cured product that was obtained in Comparative Example 1B, the adhesive force was not kept down.

<Manufacturing of Mouthguard>

Example 1C

Plaster casts of the upper and lower jaws and the occlusal state were respectively made into three-dimensional impression data by using a dental scanner for a laboratory (Kulzer LLC, CaraScan 4.0). The respective three-dimensional impression data were uploaded to a CAD design (DENTCA Co, DENTCAdesign.com). Designing of the external shape of the mouthguard was carried out by software. The thickness of the occlusal surface of the central incisor portions was set to 2.5 mm, and the thickness of the occlusal surface of the second molar portions was set to 1.0 mm (i.e., the thickness of the occlusal surface of the central incisor portions was 2.5 times the thickness of the occlusal surface of the second molar portions), and three-dimensional shaping data of the target mouthguard for the upper jaw was obtained by automatic computation by algorithms of the software.

By using a 3D printer (Kulzer LLC, CaraPrint 4.0) and under the conditions of the wavelength of the visible light being 405 nm and the illuminance of the visible light being 8.0 mJ/cm$^2$, the photocurable composition of Example 1A was shaped by using the three-dimensional shaping data for the mouthguard that was obtained as described above, and a shaped product of a mouthguard for the upper jaw was thereby obtained.

By illuminating ultraviolet light of a wavelength of 365 nm under the condition of 10 J/cm$^2$ onto the shaped product of the mouthguard that was obtained, and definitively curing the shaped product, a mouthguard was obtained.

Note that, when the obtained mouthguard was fit to plaster casts of the upper and lower jaws, the mouthguard fit with extremely good compatibility.

Comparative Example 1C

Procedures that were similar to those of Example 1C were carried out except for the point that the thickness of the occlusal surface of the central incisor portions was set to 2.0 mm, and the thickness of the occlusal surface of the second molar portions was set to 2.0 mm (i.e., the thickness of the occlusal surface of the central incisor portions was 1 times the thickness of the occlusal surface of the second molar portions), and three-dimensional shaping data of the target mouthguard for the upper jaw was obtained by automatic computation by algorithms of the software.

By using a 3D printer (Kulzer LLC, CaraPrint 4.0) and under the conditions of the wavelength of the visible light being 405 nm and the illuminance of the visible light being 8.0 mJ/cm$^2$, the photocurable composition of Example 1B was shaped by using the three-dimensional shaping data for the mouthguard that was obtained as described above, and a shaped product of a mouthguard was obtained.

By illuminating ultraviolet light of a wavelength of 365 nm under the condition of 10 J/cm$^2$ onto the shaped product of the mouthguard that was obtained, and definitively curing the shaped product, a mouthguard was obtained.

<Test when Attached to Articulator>

The mouthguards for the upper jaw that were manufactured by the methods of Example 1C and Comparative Example 1C were attached to an articulator in which plaster casts of the upper and lower jaws were mounted, and were evaluated on the basis of the following standards.

~Evaluation Standards~

A: When attached to the articulator, the mouthguard for the upper jaw, and the central incisor portions of the plaster cast of the lower jaw and the second molar portions of the plaster cast of the lower jaw, could contact respectively without carrying out occlusal adjustment.

B: When attached to the articulator, the mouthguard for the upper jaw and the second molar portions of the plaster cast of the lower jaw were in a state of contact, but a gap arose between the mouthguard for the upper jaw and the central incisor portions of the plaster cast of the lower jaw, and occlusal adjustment was needed in order to make them contact.

TABLE 8

| | Example 1C | Comparative Example 1C |
|---|---|---|
| evaluation of test when attached to articulator | A | B |

The disclosures of Japanese Patent Application No. 2019-195499 filed on Oct. 28, 2019, Japanese Patent Application No. 2019-195500 filed on Oct. 28, 2019, and Japanese Patent Application No. 2020-071833 filed on Apr. 13, 2020 are, in their entireties, incorporated by reference into the present specification.

All publications, patent applications, and technical standards mentioned in the present specification are incorporated by reference into the present specification to the same extent as if such individual publication, patent application, or technical standard was specifically and individually indicated to be incorporated by reference.

The invention claimed is:

1. A photocurable composition comprising a (meth) acrylic monomer component and a photopolymerization initiator, wherein an adhesive force of a cured product is less than or equal to 1.5 N, and a rupture elongation of the cured product is greater than or equal to 20%, wherein the (meth)acrylic monomer component contains a (meth)acrylic monomer (A) having two (meth)acryloyl groups, and a (meth)acrylic monomer (B) having one (meth)acryloyl group, and wherein at least one of the following (a) or the following (b) is satisfied:

(a) the (meth)acrylic monomer (A) includes a (meth) acrylic monomer (A-1), in which a molecular weight per one (meth)acryloyl group is greater than or equal to 300 g/mol and is less than or equal to 600 g/mol, and contains a (meth)acrylic monomer (A-2), in which a molecular weight per one (meth)acryloyl group is greater than 600 g/mol and is less than or equal to 15000 g/mol, or (b) the (meth)acrylic monomer (B) includes a (meth) acrylic monomer (B-1) having two aromatic rings and contains a (meth)acrylic monomer (B-2) having one aromatic ring.

2. The photocurable composition of claim 1, wherein the rupture elongation of the cured product is greater than or equal to 40%.

3. The photocurable composition of claim 1, wherein an aromatic ring concentration in the (meth)acrylic monomer component is greater than or equal to 0.00100 mol/g.

4. The photocurable composition of claim 1, wherein at least one of the (meth)acrylic monomer (A) or the (meth) acrylic monomer (B) has an aromatic group.

5. The photocurable composition of claim 1, wherein a content of the (meth)acrylic monomer (A), with respect to a total content of 1000 parts by mass of the (meth)acrylic monomer (A) and the (meth)acrylic monomer (B), is 250 parts by mass to 800 parts by mass.

6. The photocurable composition of claim 1, wherein the (meth)acrylic monomer (A) includes a compound expressed by the following Formula (1):

Formula (1)

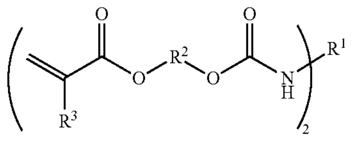

wherein, in Formula (1), each $R^1$ and $R^2$ each independently represents a divalent linking group, and each $R^3$ is independently a methyl group or a hydrogen atom.

7. The photocurable composition of claim 6, wherein:

$R^1$ is a divalent chain hydrocarbon group, or is a group formed from a divalent chain hydrocarbon group and at least one group selected from the group consisting of divalent hydrocarbon groups having an alicyclic structure, divalent hydrocarbon groups having an aromatic structure, and divalent groups containing a hetero atom, and the divalent hydrocarbon groups having an aromatic structure are divalent hydrocarbon groups expressed by the following Formula (1-a), (1-a)

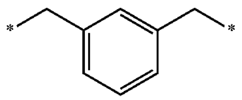

wherein, in Formula (1-a), * represents a bonding site.

8. The photocurable composition of claim 7, wherein the divalent groups containing a hetero atom in $R^1$ contain at least one bond selected from the group consisting of urethane bonds and ether bonds.

9. The photocurable composition of claim 6, wherein $R^1$ is a divalent chain hydrocarbon group, or is a group formed from a divalent chain hydrocarbon group and at least one group selected from the group consisting of divalent hydrocarbon groups having an alicyclic structure and divalent groups containing a hetero atom.

10. The photocurable composition of claim 1, wherein an aromatic ring concentration in the (meth)acrylic monomer (A) is less than or equal to 0.0016 mol/g.

11. The photocurable composition of claim 1, wherein a total content of the (meth)acrylic monomer (A) and the (meth)acrylic monomer (B) in the (meth)acrylic monomer component is greater than or equal to 90% by mass.

12. The photocurable composition of claim 1, wherein Z1 in the following Formula β is $1\times10^4$ to $100\times10^4$:

$$Z1=X1/Y1 \quad \text{Formula } \beta$$

wherein X1 (g/mol) is a molecular weight of the (meth) acrylic monomer (A) per one (meth)acryloyl group, and Y1 (mol/g) is an aromatic ring concentration in the (meth)acrylic monomer component.

13. The photocurable composition of claim 1, wherein a viscosity at 25° C. and 50 rpm measured by an E-type viscometer is 10 mPa·s to 5000 mPa·s.

14. The photocurable composition of claim 1, which is used in fabricating a mouthpiece, a gingiva mask, or a lining material by stereolithography.

15. A dental product comprising a cured product of the photocurable composition of claim 1.

16. The dental product of claim 15, which is used as a mouthpiece, a gingiva mask, or a lining material.

17. A photocurable composition comprising a (meth) acrylic monomer component and a photopolymerization initiator, wherein an adhesive force of a cured product is less than or equal to 1.5 N, and a shore A hardness of the cured product is less than or equal to 97, wherein the (meth)acrylic monomer component contains a (meth)acrylic monomer (A) having two (meth)acryloyl groups, and a (meth)acrylic monomer (B) having one (meth)acryloyl group, and (a) the (meth)acrylic monomer (A) includes a (meth) acrylic monomer (A-1), in which a molecular weight per one (meth)acryloyl group is greater than or equal to 300 g/mol and is less than or equal to 600 g/mol, and contains a (meth)acrylic monomer (A-2), in which a molecular weight per one (meth)acryloyl group is greater than 600 g/mol and is less than or equal to 15000 g/mol, or (b) the (meth)acrylic monomer (B) includes a (meth) acrylic monomer (B-1) having two aromatic rings and contains a (meth)acrylic monomer (B-2) having one aromatic ring.

18. The photocurable composition of claim 17, wherein a viscosity at 25° C. and 50 rpm measured by an E-type viscometer is 10 mPa·s to 5000 mPa·s.

* * * * *